United States Patent
Lumpkin

(10) Patent No.: US 12,054,761 B2
(45) Date of Patent: Aug. 6, 2024

(54) RAPID PRETREATMENT

(71) Applicant: Apalta Patents OÜ, Möisa (EE)

(72) Inventor: Robert E. Lumpkin, Willowbrook, IL (US)

(73) Assignee: Apalta Patents OÜ, Möisa (EE)

(*) Notice: Subject to any disclaimer, the term of this patent is extended or adjusted under 35 U.S.C. 154(b) by 0 days.

(21) Appl. No.: 18/149,811

(22) Filed: Jan. 4, 2023

(65) Prior Publication Data
US 2023/0295678 A1 Sep. 21, 2023

Related U.S. Application Data

(60) Continuation of application No. 17/076,269, filed on Oct. 21, 2020, now abandoned, which is a division of
(Continued)

(51) Int. Cl.
*C12P 19/02* (2006.01)
*B65G 53/48* (2006.01)
(Continued)

(52) U.S. Cl.
CPC .............. *C12P 19/14* (2013.01); *B65G 53/48* (2013.01); *C12M 21/04* (2013.01); *C12M 21/12* (2013.01); *C12M 33/12* (2013.01); *C12M 33/16* (2013.01); *C12M 41/40* (2013.01); *C12M 45/02* (2013.01); *C12M 45/04* (2013.01); *C12M 45/06* (2013.01); *C12M 45/09* (2013.01); *C12M 45/20* (2013.01); *C12P 7/10* (2013.01); *C12P 19/02* (2013.01);
(Continued)

(58) Field of Classification Search
None
See application file for complete search history.

(56) References Cited

U.S. PATENT DOCUMENTS

| | | |
|---|---|---|
| 1,447,461 A | 3/1923 | Brewster et al. |
| 1,867,750 A | 7/1932 | Naugle |

(Continued)

FOREIGN PATENT DOCUMENTS

| | | |
|---|---|---|
| CA | 1267407 B | 4/1990 |
| CN | 101696261 A | 4/2010 |

(Continued)

OTHER PUBLICATIONS

Agbor, et al. Biomass pretreatment: fundamentals toward application. Biotechnol Adv. Nov.-Dec. 2011 29(6):675-85. doi: 10.1016/j.biotechadv.2011.05.005. Epub May 23, 2011.
(Continued)

*Primary Examiner* — Neil N Turk
(74) *Attorney, Agent, or Firm* — Wilson Sonsini Goodrich & Rosati

(57) ABSTRACT

Disclosed herein are methods, systems, and compositions for the pretreatment of biomass within seconds with low inhibitor formation. The pretreatment process is used to convert biomass to a fuel or other useful chemicals by subjecting the feedstock to a rapid retention time under pressure and temperature and/or chemical reactant. The system includes a continuously-operating valve discharge apparatus to discharge pretreated feedstock while maintaining uniform pressure on the pretreatment system.

13 Claims, 13 Drawing Sheets

Related U.S. Application Data application No. 14/971,481, filed on Dec. 16, 2015, now Pat. No. 10,844,413, which is a continuation of application No. PCT/US2015/064850, filed on Dec. 9, 2015.

(60) Provisional application No. 62/089,704, filed on Dec. 9, 2014.

(51) Int. Cl.
| | |
|---|---|
| *C12M 1/00* | (2006.01) |
| *C12M 1/107* | (2006.01) |
| *C12M 1/26* | (2006.01) |
| *C12M 1/33* | (2006.01) |
| *C12M 1/34* | (2006.01) |
| *C12P 7/10* | (2006.01) |
| *C12P 19/14* | (2006.01) |
| *F16K 1/12* | (2006.01) |

(52) U.S. Cl.
CPC ............ *F16K 1/12* (2013.01); *C12P 2201/00* (2013.01); *Y02E 50/10* (2013.01)

(56) References Cited

U.S. PATENT DOCUMENTS

| | | |
|---|---|---|
| 2,362,357 A | 11/1944 | Cummins |
| 2,388,222 A | 10/1945 | Behrman |
| 2,594,544 A | 4/1952 | Elving et al. |
| 2,763,580 A | 9/1956 | Zabor |
| 3,563,799 A | 2/1971 | James et al. |
| 3,577,358 A | 5/1971 | Thomas et al. |
| 3,730,770 A | 5/1973 | Zievers et al. |
| 3,819,292 A | 6/1974 | Wentworth |
| 4,048,341 A | 9/1977 | Lagerstrom et al. |
| 4,052,988 A | 10/1977 | Doddi et al. |
| 4,070,232 A | 1/1978 | Funk |
| 4,182,780 A | 1/1980 | Lagerstrom et al. |
| 4,186,658 A | 2/1980 | Brown |
| 4,201,596 A | 5/1980 | Burroughs et al. |
| 4,214,947 A | 7/1980 | Berger |
| 4,237,226 A | 12/1980 | Grethlein |
| 4,242,226 A | 12/1980 | Siren et al. |
| 4,288,551 A | 9/1981 | Gudnason et al. |
| 4,326,032 A | 4/1982 | Grove |
| 4,350,766 A | 9/1982 | Mehlberg |
| 4,395,488 A | 7/1983 | Rowe |
| 4,414,330 A | 11/1983 | Zucker et al. |
| 4,427,584 A | 1/1984 | Legrand et al. |
| 4,447,534 A | 5/1984 | Moebus et al. |
| 4,452,973 A | 6/1984 | Casey et al. |
| 4,478,644 A | 10/1984 | Berger et al. |
| 4,478,854 A | 10/1984 | Adler-Nissen et al. |
| 4,502,890 A | 3/1985 | Urbanic |
| 4,520,105 A | 5/1985 | Sinner et al. |
| 4,600,590 A | 7/1986 | Dale |
| 4,612,286 A | 9/1986 | Sherman et al. |
| 4,615,742 A | 10/1986 | Wright |
| 4,632,795 A | 12/1986 | Huber et al. |
| 4,643,191 A | 2/1987 | Bezwada et al. |
| 4,644,060 A | 2/1987 | Chou |
| 4,650,689 A | 3/1987 | Hedrick |
| 4,716,203 A | 12/1987 | Casey et al. |
| 4,728,367 A | 3/1988 | Huber et al. |
| 4,806,475 A | 2/1989 | Gould |
| 4,862,168 A | 8/1989 | Beard et al. |
| 4,935,183 A | 6/1990 | Wenger et al. |
| 4,942,035 A | 7/1990 | Churchill et al. |
| 5,019,094 A | 5/1991 | Bezwada et al. |
| 5,037,663 A | 8/1991 | Dale |
| 5,080,665 A | 1/1992 | Jarrett et al. |
| 5,114,488 A | 5/1992 | Huber et al. |
| 5,144,008 A | 9/1992 | Ikeda et al. |
| 5,171,592 A | 12/1992 | Holtzapple et al. |
| 5,177,008 A | 1/1993 | Kampen |
| 5,177,009 A | 1/1993 | Kampen |
| 5,232,649 A | 8/1993 | Andersen et al. |
| 5,338,366 A | 8/1994 | Grace et al. |
| 5,340,403 A | 8/1994 | Fields et al. |
| 5,378,491 A | 1/1995 | Stanley et al. |
| 5,384,333 A | 1/1995 | Davis et al. |
| 5,449,513 A | 9/1995 | Yokoyama et al. |
| 5,454,911 A | 10/1995 | Rafferty |
| 5,473,061 A | 12/1995 | Bredereck et al. |
| 5,476,909 A | 12/1995 | Kim et al. |
| 5,510,103 A | 4/1996 | Yokoyama et al. |
| 5,543,158 A | 8/1996 | Gref et al. |
| 5,548,035 A | 8/1996 | Kim et al. |
| 5,612,052 A | 3/1997 | Shalaby et al. |
| 5,683,723 A | 11/1997 | Spenlehauer et al. |
| 5,693,296 A | 12/1997 | Holtzapple et al. |
| 5,702,717 A | 12/1997 | Cha et al. |
| 5,726,046 A | 3/1998 | Farone et al. |
| 5,846,787 A | 12/1998 | Ladisch et al. |
| 5,865,898 A | 2/1999 | Holtzapple et al. |
| 5,916,780 A | 6/1999 | Foody et al. |
| 5,939,544 A | 8/1999 | Karstens et al. |
| 5,969,189 A | 10/1999 | Holtzapple et al. |
| 5,986,133 A | 11/1999 | Holtzapple et al. |
| 6,043,392 A | 3/2000 | Holtzapple et al. |
| 6,106,888 A | 8/2000 | Dale et al. |
| 6,176,176 B1 | 1/2001 | Dale et al. |
| 6,258,175 B1 | 7/2001 | Lightner |
| 6,262,313 B1 | 7/2001 | Holtzapple et al. |
| 6,332,542 B2 | 12/2001 | Bilodeau et al. |
| 6,355,456 B1 | 3/2002 | Hallberg et al. |
| 6,365,732 B1 | 4/2002 | Van |
| 6,409,841 B1 | 6/2002 | Lombard |
| 6,416,621 B1 | 7/2002 | Karstens |
| 6,475,552 B1 | 11/2002 | Shah et al. |
| 6,478,965 B1 | 11/2002 | Holtzapple et al. |
| 6,509,180 B1 | 1/2003 | Verser et al. |
| 6,599,519 B1 | 7/2003 | Seo et al. |
| 6,616,941 B1 | 9/2003 | Seo et al. |
| 6,872,316 B2 | 3/2005 | Heikkila et al. |
| 6,916,788 B2 | 7/2005 | Seo et al. |
| 6,990,459 B2 | 1/2006 | Schneider |
| 7,109,005 B2 | 9/2006 | Eroma et al. |
| 7,198,925 B2 | 4/2007 | Foody |
| 7,217,770 B2 | 5/2007 | Seo et al. |
| 7,218,975 B2 | 5/2007 | Stevens et al. |
| 7,311,901 B2 | 12/2007 | Seo et al. |
| 7,503,981 B2 | 3/2009 | Wyman et al. |
| 7,550,157 B2 | 6/2009 | Seo et al. |
| 7,807,419 B2 | 10/2010 | Hennessey et al. |
| 7,819,976 B2 | 10/2010 | Friend et al. |
| 7,909,895 B2 | 3/2011 | Dickinson et al. |
| 7,910,338 B2 | 3/2011 | Hennessey et al. |
| 7,930,085 B2 | 4/2011 | Anderson et al. |
| 7,932,063 B2 | 4/2011 | Dunson et al. |
| 7,932,065 B2 | 4/2011 | Medoff |
| 7,935,840 B2 | 5/2011 | Leveson et al. |
| 7,976,259 B2 | 7/2011 | Craig et al. |
| 8,003,352 B2 | 8/2011 | Foody et al. |
| 8,024,074 B2 | 9/2011 | Stelford et al. |
| 8,086,354 B2 | 12/2011 | Bondar et al. |
| 8,103,385 B2 | 1/2012 | Macharia et al. |
| 8,110,383 B2 | 2/2012 | Joensson et al. |
| 8,123,864 B2 | 2/2012 | Christensen et al. |
| 8,168,840 B2 | 5/2012 | Brady et al. |
| 8,318,453 B2 | 11/2012 | Medoff |
| 8,323,923 B1 | 12/2012 | Horton |
| 8,328,947 B2 | 12/2012 | Anand et al. |
| 8,394,277 B2 | 3/2013 | Bonanni et al. |
| 8,426,161 B1 | 4/2013 | Horton |
| 8,445,236 B2 | 5/2013 | Hennessey et al. |
| 8,529,765 B2 | 9/2013 | Horton |
| 8,561,533 B2 | 10/2013 | Burke |
| 8,563,277 B1 | 10/2013 | Parekh et al. |
| 8,691,050 B2 | 4/2014 | Christensen |
| 8,722,924 B1 | 5/2014 | Overheul et al. |
| 8,765,430 B2 | 7/2014 | Parekh et al. |
| 8,926,932 B2 | 1/2015 | Pfeifer et al. |

(56) References Cited

U.S. PATENT DOCUMENTS

| | | |
|---|---|---|
| 9,004,742 B2 | 4/2015 | Burke et al. |
| 9,056,294 B2 | 6/2015 | Fink et al. |
| 9,115,214 B2 | 8/2015 | Nguyen et al. |
| 9,150,936 B2 | 10/2015 | Dottori et al. |
| 9,410,216 B2 | 8/2016 | Eyal et al. |
| 9,499,635 B2 | 11/2016 | Chesonis et al. |
| 9,809,867 B2 | 11/2017 | Parekh et al. |
| 2002/0038058 A1 | 3/2002 | Holtzapple et al. |
| 2002/0153317 A1 | 10/2002 | Heikkila et al. |
| 2002/0164730 A1* | 11/2002 | Ballesteros Perdices ............... C12M 21/16 435/163 |
| 2002/0164731 A1 | 11/2002 | Eroma et al. |
| 2002/0192774 A1 | 12/2002 | Ahring et al. |
| 2002/0197686 A1 | 12/2002 | Lightner |
| 2003/0109011 A1 | 6/2003 | Hood et al. |
| 2003/0143659 A1 | 7/2003 | Bijl et al. |
| 2003/0199049 A1 | 10/2003 | Nguyen et al. |
| 2003/0221361 A1 | 12/2003 | Russell et al. |
| 2003/0224088 A1 | 12/2003 | Burdick |
| 2004/0152881 A1 | 8/2004 | Holtzapple et al. |
| 2004/0168960 A1 | 9/2004 | Holtzapple et al. |
| 2004/0171136 A1 | 9/2004 | Holtzapple et al. |
| 2005/0054064 A1 | 3/2005 | Talluri et al. |
| 2005/0136520 A1* | 6/2005 | Kinley ............... C12M 45/20 435/155 |
| 2005/0203291 A1 | 9/2005 | Svenson et al. |
| 2005/0244934 A1 | 11/2005 | Foody et al. |
| 2005/0271770 A1 | 12/2005 | Hughes |
| 2005/0272134 A1 | 12/2005 | Hughes |
| 2006/0003064 A1 | 1/2006 | James |
| 2006/0024801 A1 | 2/2006 | Holtzapple et al. |
| 2006/0032113 A1 | 2/2006 | Whitney |
| 2006/0069244 A1 | 3/2006 | Holtzapple et al. |
| 2006/0090749 A1 | 5/2006 | Rein et al. |
| 2006/0188980 A1 | 8/2006 | Holtzapple et al. |
| 2006/0211101 A1 | 9/2006 | Chotani et al. |
| 2006/0251764 A1 | 11/2006 | Abbas et al. |
| 2006/0280663 A1 | 12/2006 | Osato et al. |
| 2006/0281157 A1 | 12/2006 | Chotani et al. |
| 2007/0016095 A1 | 1/2007 | Low et al. |
| 2007/0037259 A1 | 2/2007 | Hennessey et al. |
| 2007/0118916 A1 | 5/2007 | Puzio et al. |
| 2007/0148750 A1 | 6/2007 | Hoshino et al. |
| 2007/0148751 A1 | 6/2007 | Griffin et al. |
| 2007/0190626 A1 | 8/2007 | Wilkening et al. |
| 2007/0275447 A1 | 11/2007 | Lewis et al. |
| 2008/0014617 A1 | 1/2008 | Cerea |
| 2008/0057555 A1 | 3/2008 | Nguyen |
| 2008/0121359 A1 | 5/2008 | Holtzapple et al. |
| 2008/0145903 A1 | 6/2008 | Holmes et al. |
| 2008/0176301 A1 | 7/2008 | Granda et al. |
| 2008/0227162 A1 | 9/2008 | Varanasi et al. |
| 2008/0280338 A1 | 11/2008 | Hall et al. |
| 2008/0286193 A1 | 11/2008 | Bento et al. |
| 2009/0004698 A1 | 1/2009 | Vande et al. |
| 2009/0023187 A1 | 1/2009 | Foody et al. |
| 2009/0042259 A1 | 2/2009 | Dale et al. |
| 2009/0043686 A1 | 2/2009 | Matsumoto |
| 2009/0053800 A1 | 2/2009 | Friend et al. |
| 2009/0064566 A1 | 3/2009 | Brummerstedt et al. |
| 2009/0084801 A1 | 4/2009 | Coe |
| 2009/0098617 A1 | 4/2009 | Burke et al. |
| 2009/0117635 A1 | 5/2009 | Bradley et al. |
| 2009/0126276 A1 | 5/2009 | Johnson et al. |
| 2009/0181434 A1 | 7/2009 | Aikens et al. |
| 2009/0298149 A1 | 12/2009 | Wang et al. |
| 2010/0008998 A1 | 1/2010 | Kang et al. |
| 2010/0021980 A1 | 1/2010 | Mcdonald et al. |
| 2010/0041119 A1 | 2/2010 | Christensen et al. |
| 2010/0043246 A1 | 2/2010 | Smith et al. |
| 2010/0055741 A1 | 3/2010 | Galvez, III et al. |
| 2010/0056774 A1 | 3/2010 | Anand et al. |
| 2010/0082139 A1 | 4/2010 | Macharia et al. |
| 2010/0082140 A1 | 4/2010 | Macharia et al. |
| 2010/0082166 A1 | 4/2010 | Macharia et al. |
| 2010/0143974 A1 | 6/2010 | Chung et al. |
| 2010/0144001 A1 | 6/2010 | Horton |
| 2010/0216201 A1 | 8/2010 | Soong et al. |
| 2010/0221805 A1 | 9/2010 | Kelly |
| 2010/0221819 A1 | 9/2010 | Foody et al. |
| 2010/0227369 A1 | 9/2010 | Narendranath et al. |
| 2010/0317053 A1 | 12/2010 | Stromberg et al. |
| 2011/0020874 A1 | 1/2011 | Hata |
| 2011/0033268 A1 | 2/2011 | Craig et al. |
| 2011/0039317 A1 | 2/2011 | Medoff |
| 2011/0079219 A1 | 4/2011 | Mcdonald et al. |
| 2011/0081689 A1 | 4/2011 | Flanegan et al. |
| 2011/0114765 A1 | 5/2011 | Brady et al. |
| 2011/0129886 A1 | 6/2011 | Howard et al. |
| 2011/0171709 A1 | 7/2011 | Bardsley et al. |
| 2011/0175358 A1 | 7/2011 | Langson |
| 2011/0197496 A1 | 8/2011 | O'Connor et al. |
| 2011/0201084 A1 | 8/2011 | Wyman et al. |
| 2011/0212487 A1 | 9/2011 | Emme et al. |
| 2011/0223641 A1 | 9/2011 | Stephanopoulos et al. |
| 2011/0244499 A1 | 10/2011 | Realff et al. |
| 2011/0258911 A1 | 10/2011 | Hanson et al. |
| 2011/0258913 A1 | 10/2011 | Stamires et al. |
| 2011/0275860 A1 | 11/2011 | Beldring et al. |
| 2011/0300586 A1 | 12/2011 | Liu et al. |
| 2012/0006320 A1 | 1/2012 | Nguyen |
| 2012/0037325 A1 | 2/2012 | Beldring et al. |
| 2012/0041186 A1 | 2/2012 | Pschorn et al. |
| 2012/0100045 A1 | 4/2012 | Beldring et al. |
| 2012/0100577 A1 | 4/2012 | Medoff et al. |
| 2012/0107888 A1 | 5/2012 | Schmalisch et al. |
| 2012/0108798 A1 | 5/2012 | Wenger et al. |
| 2012/0111714 A1* | 5/2012 | Court ............... C10G 1/083 202/84 |
| 2012/0116063 A1 | 5/2012 | Jansen et al. |
| 2012/0122162 A1 | 5/2012 | Romero et al. |
| 2012/0125324 A1 | 5/2012 | Fisk |
| 2012/0190092 A1 | 7/2012 | Jaquess et al. |
| 2012/0196233 A1 | 8/2012 | Ni et al. |
| 2012/0211427 A1 | 8/2012 | Bonanni et al. |
| 2012/0214205 A1* | 8/2012 | Iida et al. ............... C12P 7/10 435/72 |
| 2012/0214216 A1 | 8/2012 | Brady et al. |
| 2012/0269715 A1 | 10/2012 | Kamegawa et al. |
| 2012/0282655 A1 | 11/2012 | Gibbs |
| 2013/0014749 A1 | 1/2013 | Dottori et al. |
| 2013/0071903 A1 | 3/2013 | Rowland et al. |
| 2013/0118483 A1 | 5/2013 | Gao et al. |
| 2013/0210101 A1 | 8/2013 | Parekh et al. |
| 2013/0225854 A1 | 8/2013 | Ryba et al. |
| 2013/0274455 A1 | 10/2013 | Parekh et al. |
| 2013/0274456 A1 | 10/2013 | Parekh et al. |
| 2013/0323830 A1 | 12/2013 | Horton |
| 2014/0034047 A1 | 2/2014 | Retsina et al. |
| 2014/0106418 A1 | 4/2014 | Parekh et al. |
| 2014/0178944 A1 | 6/2014 | Parekh et al. |
| 2014/0188543 A1 | 7/2014 | Pearlmutter et al. |
| 2014/0200334 A1 | 7/2014 | Lake et al. |
| 2014/0242867 A1 | 8/2014 | Jansen et al. |
| 2014/0248676 A1 | 9/2014 | Griffin et al. |
| 2014/0262727 A1 | 9/2014 | Felix et al. |
| 2014/0275500 A1 | 9/2014 | Mikhnevich et al. |
| 2014/0342423 A1 | 11/2014 | Parekh et al. |
| 2015/0018584 A1 | 1/2015 | Parekh et al. |
| 2015/0183948 A1 | 7/2015 | Chuang et al. |
| 2015/0196893 A1 | 7/2015 | Mennell et al. |
| 2015/0197424 A1 | 7/2015 | Mennell et al. |
| 2015/0224428 A1 | 8/2015 | Lehoux et al. |
| 2015/0232902 A1* | 8/2015 | Romero ............... C12P 7/10 435/277 |
| 2015/0329927 A1 | 11/2015 | Parekh |
| 2016/0031713 A1 | 2/2016 | Fish et al. |
| 2016/0032414 A1 | 2/2016 | Parekh et al. |
| 2016/0194433 A1 | 7/2016 | Langlois et al. |
| 2016/0333146 A1 | 11/2016 | Miettinen et al. |
| 2017/0226535 A1 | 8/2017 | Tudman |
| 2017/0247255 A1 | 8/2017 | Wittmann et al. |

(56) References Cited

U.S. PATENT DOCUMENTS

| | | |
|---|---|---|
| 2018/0002451 A1 | 1/2018 | Ge et al. |
| 2018/0079871 A1 | 3/2018 | Tudman |
| 2019/0040478 A1 | 2/2019 | Tudman et al. |

FOREIGN PATENT DOCUMENTS

| | | | |
|---|---|---|---|
| CN | 102216435 A | 10/2011 | |
| CN | 102585248 A | 7/2012 | |
| EP | 0037912 A2 | 10/1981 | |
| EP | 0105937 B1 | 11/1987 | |
| EP | 0150933 B2 | 8/1997 | |
| EP | 1259466 B1 | 10/2008 | |
| EP | 1307735 B1 | 11/2008 | |
| EP | 1299170 B1 | 8/2010 | |
| EP | 2812437 A1 | 12/2014 | |
| EP | 2836602 A1 | 2/2015 | |
| JP | 2006149343 A | 6/2006 | |
| KR | 20100123093 A | 11/2010 | |
| KR | 20110046090 | 5/2011 | |
| KR | 20110046090 A | 5/2011 | |
| KR | 20130115577 | 10/2013 | |
| KR | 20130115577 A | 10/2013 | |
| KR | 101391435 B1 | 5/2014 | |
| KR | 20140072866 A | 6/2014 | |
| WO | WO-0132715 A1 | 5/2001 | |
| WO | WO-0160752 A1 | 8/2001 | |
| WO | WO-0200324 A1 | 1/2002 | |
| WO | WO-0201220 A2 | 1/2002 | |
| WO | WO-0201220 A3 | 9/2002 | |
| WO | WO-2004081193 A2 | 9/2004 | |
| WO | WO-2004108969 A1 | 12/2004 | |
| WO | WO-2004113551 A1 | 12/2004 | |
| WO | WO-2005052195 A1 | 6/2005 | |
| WO | WO-2005087937 A2 | 9/2005 | |
| WO | WO-2005118828 A1 | 12/2005 | |
| WO | WO-2006024242 A1 | 3/2006 | |
| WO | WO-2006101832 A2 | 9/2006 | |
| WO | WO-2007009463 A2 | 1/2007 | |
| WO | WO-2007009463 A3 | 7/2007 | |
| WO | WO-2008020901 A2 | 2/2008 | |
| WO | WO-2008073186 A2 | 6/2008 | |
| WO | WO-2006101832 A3 | 4/2009 | |
| WO | WO-2009063138 A2 | 5/2009 | |
| WO | WO-2009087680 A2 | 7/2009 | |
| WO | WO-2010011328 A1 | 1/2010 | |
| WO | WO-2010034055 A1 | 4/2010 | |
| WO | WO-2010037780 A1 | 4/2010 | |
| WO | WO-2010056940 A2 | 5/2010 | |
| WO | WO-2010068637 A1 | 6/2010 | |
| WO | WO-2010115488 A1 | 10/2010 | |
| WO | WO-2010123932 A1 | 10/2010 | |
| WO | WO-2011003962 A2 | 1/2011 | |
| WO | WO-2011022811 A1 | 3/2011 | |
| WO | WO-2011028554 A1 | 3/2011 | |
| WO | WO-2011028853 A1 | 3/2011 | |
| WO | WO-2011103033 A1 | 8/2011 | |
| WO | WO-2012051523 A1 | 4/2012 | |
| WO | WO-2012099967 A1 | 7/2012 | |
| WO | WO-2012155239 A1 | 11/2012 | |
| WO | WO-2013120035 A1 | 8/2013 | |
| WO | WO-2013148415 A1 | 10/2013 | |
| WO | WO-2013155496 A1 | 10/2013 | |
| WO | WO-2013186184 A1 | 12/2013 | |
| WO | WO-2014026154 A1 | 2/2014 | |
| WO | WO-2014039984 A1 * | 3/2014 | ............ C12M 21/18 |
| WO | WO-2014143753 A1 | 9/2014 | |
| WO | WO-2014169079 A2 | 10/2014 | |
| WO | WO-2014190294 A1 | 11/2014 | |
| WO | WO-2015179243 A1 | 11/2015 | |
| WO | WO-2016001484 A1 | 1/2016 | |
| WO | WO-2016094594 A1 | 6/2016 | |
| WO | WO-2016128224 A1 | 8/2016 | |
| WO | WO-2017049090 A1 | 3/2017 | |
| WO | WO-2018151833 A1 | 8/2018 | |

OTHER PUBLICATIONS

Alcohol and Tobacco Tax and Trade Bureau, treasury. 27 C.F.R. § 19.134 Bonded warehouse not on premises qualified for production of spirits, p. 381, Apr. 1, 1997 revision.

Aldrich. 2003-2004. Particle size conversion Table, 2 Pages or p. T848 of the Aldrich 2003-2004 Catalog/ Handbook of Fine Chemicals.

Arshanitsa, et al., Two Approaches for Introduction of Wheat Straw Lignin into Rigid Polyurethane Foams. AIP Conf. Proc. 1593, 388-391 (2014); doi: 10.1063/1.4873806.

Ballesteros, et al. Ethanol from lignocellulose materials by a simultaneous saccharification and fermentation process (SFS) with Kluyveromyces marxianus CECT 10875. Process Biochemistry, vol. 39, pp. 1843-1848, 2004.

Boggan. 2003. Alcohol, Chemistry and You Sources and Uses of Ethyl Alcohol. Kennesaw State University, pp. 1-5, Printed May 17, 2010. http://www.chemcases.com/alcohol/alc-03.htm/.

Bolsen, et al. Silage Fermentation and Silage Additives: Review. AJAS 1996 vol. 9 (No. 5). pp. 483-493.

Borregaard, Potential applications for different lignin sources based on experience from Borregaard and what about the future? Oct. 21, 2015; 26 Pages.

Brigham, et al. Bacterial Carbon Storage to Value Added Products. J Microbial Biochem Technol 2011, S3-002.

Co-pending U.S. Appl. No. 13/793,860, inventor Jerry; W. Horton, filed Mar. 11, 2013.

Co-pending U.S. Appl. No. 15/267,617, inventor Tudman; Scott, filed Sep. 16, 2016.

Co-pending U.S. Appl. No. 15/293,478, inventors Chesonis; Arunas et al., filed Oct. 14, 2016.

Co-pending U.S. Appl. No. 15/418,204, inventors Parekh; Sarad et al., filed Jan. 27, 2017.

Co-pending U.S. Appl. No. 15/430,370, inventors Gu; Changfeng et al., filed Feb. 10, 2017.

Dale, et al. Hydrolysis of lignocellulosics at low enzyme levels: Application of the AFEX process. Bioresource Technology. Apr. 1996; 56(1):111-116.

Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.

Dionex CarboPac PA10. Column Product Manual. Thermo Scientific. P/N: 065495-01. Dec. 2012.

Dowe, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Dowe, et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages) 2008.

EP15866602.4 European Search Report dated Jul. 4, 2018.

"European search report and search opinion dated Sep. 25, 2015 for EP Application No. 13747149.6.".

"European search report and search opinion dated Sep. 28, 2015 for EP Application No. 13775895.9.".

Felix et al. In vitro and in vivo digestibility of soya-bean straw treated with various alkalis. Anim Prod. 1990; 51:47-61.

Gibreel, et al. Fermentation of barley by using *Saccharomyces cerevisiae*: examination of barley as a feedstock for bioethanol production and value-added products. Appl Environ Microbiol. Mar. 2009;75(5):1363-72. doi: 10.1128/AEM.01512-08. Epub Dec. 29, 2008.

Gregorova, et al., Lignin-Containing Polyethylene Films With Antibacterial Activity.Brno, Czech Republic, EU, 2011; 21-23, 9.

Gum, et al. Structural characterization of a glycoprotein cellulase, 1,4-beta-D-glucan cellubiohydrolase C from trichodermaviride. Biochem. Biophys. Acta. 1976; 446:370-86.

Huang, et al., Characterization of Biobased Polyurethane Foams Employing Lignin Fractionated from Microwave Liquefied Switchgrass.

(56) References Cited

OTHER PUBLICATIONS

Hindawi International Journal of Polymer Science vol. 2017, Article ID 4207367, 8 pages https://doi.org/10.1155/2017/4207367.
International search report and written opinion dated Jan 26, 2010for PCT/US2009/67221.
International search report and written opinion dated Mar. 8, 2016 for PCT Application No. US2014/033567.
International search report and written opinion dated Apr. 1, 2016 for PCT Application No. US2015/064850.
International search report and written opinion dated May 30, 2013 for PCT/US2013/025457.
International search report and written opinion dated Jun. 20, 2013 for PCT/US2013/036497.
International search report and written opinion dated Jul. 26, 2013 for PCT Application No. US2013/032955.
International search report and written opinion dated Jul. 29, 2015 for PCT Application No. US2015/031146.
"International search report and written opinion dated Nov. 16, 2017 for PCT Application No. US-2017052315".
International search report and written opinion dated Nov. 19, 2013 for PCT/US2013/054411.
International search report and written opinion dated Nov. 30, 2016 for PCT Application No. US-2016052143.
International search report dated Aug. 25, 2014 for PCT Application No. US2014/027850.
International search report dated Sep. 8, 2014 for PCT Application No. US2014/039399.
Jin, et al., Liquefaction of lignin by polyethyleneglycol and glycerol. Bioresource Technology 102 (2011) 3581-3583.
Jones, et al. (1994, Ethanolic Fermentation of Blackstrap Molasses and Sugarcane Juice Using Very High Gravity Technology. J. Agric. Food Chem, vol. 42, pp. 1242-1246).
Kamal, et al., Detoxification of sago trunk hydrolysate using activated charcoal for xylitol production, Procedia Food Science 1, (2011) 908-913.
Kim, et al. Lime pretreatment and enzymatic hydrolysis of corn stover. Bioresour Technol. Dec. 2005;96(18):1994-2006.
Kim, et al. Pretreatment and fractionation of corn stover by ammonia recycle percolation process. Bioresour Technol. Dec. 2005;96(18):2007-13.
Larsson, et al. Comparison of different methods for the detoxification of lignocellulose hydrolyzates of spruce. Applied Biochemistry and Biotechnology. 1999; 77-79:91-103.
Lignimatch. Future use of lignin in value added products: A roadmap for possible Nordic/Baltic innovation. The roadmap compiles inputs from the detailed technical reports delivered in the LigniMatch project during 2007-2009. For more information, see the project website at http://www.chalmers.se/gmv/EN/projects/lignimatch.
Lloyd, et al. Combined sugar yields for dilute sulfuric acid pretreatment of corn stover followed by enzymatic hydrolysis of the remaining solids. Bioresour Technol. Dec. 2005;96(18):1967-77.
Malherbe, et al. Lignocellulose biodegradation: Fundamentals and applications. Re/Views in Environmental Science & Bio/Technology. 2001; 1:105-114.
Mosier, et al. Features of promising technologies for pretreatment of lignocellulosic biomass. Bioresour Technol. Apr. 2005;96(6):673-86.
Mosier, et al. Optimization of pH controlled liquid hot water pretreatment of corn stover. Bioresour Technol. Dec. 2005;96(18):1986-93.
Nevoigt, et al. Osmoregulation and glycerol metabolism in the yeast *Saccharomyces cerevisiae*. FEMS Microbiol Rev. Nov. 1997;21(3):231-41.
Notice of allowance dated Jan. 9, 2013 for U.S. Appl. No. 13/646,425.
Notice of allowance dated Feb. 20, 2014 for U.S. Appl. No. 13/731,633.
Notice of allowance dated Jun. 7, 2013 for U.S. Appl. No. 12/633,555.
"Notice of allowance dated Jun. 27, 2017 for U.S. Appl. No. 14/776,411".
Notice of allowance dated Jul. 8, 2013 for U.S. Appl. No. 13/686,477.
Notice of allowance dated Jul. 14, 2016 for U.S. Appl. No. 14/050,244.
Notice of allowance dated Aug. 8, 2013 for U.S. Appl. No. 12/633,555.
Notice of allowance dated Oct. 15, 2012 for U.S. Appl. No. 11/974,129.
Office action dated Jan. 5, 2016 for U.S. Appl. No. 14/050,244.
"Office action dated Feb. 5, 2016 for U.S. Appl. No. 13/947,368."
Office action dated Feb. 20, 2013 for U.S. Appl. No. 13/686,477.
Office action dated Mar. 10, 2015 for U.S. Appl. No. 13/931,303.
Office action dated Mar. 12, 2015 for U.S. Appl. No. 14/050,244.
Office action dated Mar. 20, 2013 for U.S. Appl. No. 12/633,555.
Office action dated Mar. 24, 2014 for U.S. Appl. No. 13/724,763.
Office action dated Apr. 7, 2016 for U.S. Appl. No. 14/050,244.
Office action dated May 24, 2010 for U.S. Appl. No. 11/974,129.
Office action dated Jun. 25, 2013 for U.S. Appl. No. 13/731,633.
Office action dated Jul. 5, 2022 for U.S. Appl. No. 17/076,269.
Office action dated Jul. 6, 2012 for U.S. Appl. No. 11/974,129.
"Office action dated Jul. 9, 2015 for U.S. Appl. No. 13/793,860."
"Office action dated Jul. 12, 2017 for U.S. Appl. No. 14/713,906"
Office action dated Jul. 28, 2016 for U.S. Appl. No. 14/254,441.
Office action dated Sep. 11, 2015 for U.S. Appl. No. 14/254,441.
Office action dated Sep. 16, 2016 for U.S. Appl. No. 13/947,368.
Office action dated Sep. 21, 2015 for U.S. Appl. No. 13/842,941.
Office action dated Oct. 3, 2012 for U.S. Appl. No. 12/633,555.
Office action dated Oct. 8, 2014 for U.S. Appl. No. 13/793,860.
Office action dated Oct. 18, 2013 for U.S. Appl. No. 13/724,763.
Office action dated Nov. 8, 2010 for U.S. Appl. No. 11/974,129.
"Office Action dated Nov. 8, 2017 for U.S. Appl. No. 14/340,179"
Office action dated Jan. 19, 2017 for U.S. Appl. No. 14/340,179.
Office action dated Dec. 5, 2016 for U.S. Appl. No. 13/842,941.
Office action dated Dec. 15, 2016 for U.S. Appl. No. 14/776,411.
Office action dated Dec. 29, 2014 for U.S. Appl. No. 13/842,941.
Office action dated Jan. 23, 2017 for U.S. Appl. No. 14/140,880.
Palmqvist, et al. Fermentation of lignocellulosic hydrolysates. I: inhibition and detoxification. Bioresource Technology. 2000; 74(1):17-24.
Parekh, et al. Production of glycerol by hansenula anomala. Biotechnol Bioeng. Jul. 1985;27(7):1089-91.
PCT/US2018/000047 International Search Report and Written Opinion dated Jun. 7, 2018.
Quantitative Instrument Analysis, https://www.gmu.edu/depts/SRIF/tutorial/gcd/quant.htm, p. s1-s3; Updated May 8, 1998, Printed Jun. 23, 2015.
Santoro, et al. A High-throughput Platform for Screening Milligram Quantities of Plant Biomass for Lignocellulose Digestibility. Bioenerg. Res. Jan. 2010; 3:93-102.
Shapouri, et al. 2006. The Economic Feasibility of Ethanol Production From Sugar in the United States, USDA, 78 Pages, Jul. 2006.
Silva, et al. Downstream processing for xylitol recovery from fermented sugar cane bagasse hydrolysate using aluminium polychloride. Z Naturforsch C. Jan.-Feb. 2000;55(1-2):10-5.
Sluiter, et al. Determination of structural carbohydrates and lignin in biomass. National Renewable Energy Laboratory. Technical report NREL/TP-510-42618. Revised Jun. 2010.
Sun, et al. Dilute acid pretreatment of rye straw and bermudagrass for ethanol production. Bioresour Technol. Sep. 2005;96(14):1599-606. Epub Feb. 24, 2005.
Taherzadeh, et al. Pretreatment of Lignocellulosic Wastes to Improve Ethanol and Biogas Production: A Review. International Journal of Molecular Sciences. 2008(9). pp. 1621-1651.
Taylor. From Raw Sugar to Raw materials. Chemical innovation. 2000; 30:45-48.
U.S. Appl. No. 14/340,179 Office Action dated Sep. 4, 2018.
U.S. Appl. No. 13/793,860 Office Action dated Apr. 7, 2016.
U.S. Appl. No. 15/267,617 Office Action dated Apr. 27, 2018.
USDA, "The Economic Feasibility of Ethanol Production From Sugar in the United States"; Jul. 2006, 69 pages.
Varhegyi, et al. (1989. Kinetics of the thermal decomposition of cellulose, hemicellulose, and sugarcane bagasse. Energy Fuels, vol. 3, No. 3, pp. 329-335).

(56) References Cited

OTHER PUBLICATIONS

Waiss, et al. Improving Digestibility of Straws for Ruminant Feed by Aqueous Ammonia. Journal of Animal Science. 1972; 35(1):109-112.

Wallace.,Feasibility Study of Co-Locating and Integrating Ethanol Production Plants from Corn Starch and Lignocellulosic Feedstocks. United States Department of Agriculture, United States Department of Energy, 2005, NREL, Golden Colorado, Wyndmoor, PA.

Waltermann, et al. Rhodococcus opacus strain PD630 as a new source of high-value single-cell oil? Isolation and characterization of triacylglycerols and other storage lipids. Microbiology. 2000; 146:1143-1149.

Wojciechowski, et al. Acid and Enzymatic Hydrolysis to Recover Reducing Sugars from Cassava Bagasse: an Economic Study. Brazilian Archives of Biology and Technology, vol. 45, No. 3, pp. 393-400, 2002.

Xue, et al., Producing Lignin-Based Polyols through Microwave-Assisted Liquefaction for Rigid Polyurethane Foam Production. Materials 2015, 8, 586-599; doi: 10.3390/ma8020586.

Zheng, et al. Extrusion Pretreatment of Lignocellulosic Biomass: A Review. Int. J. Mol. Sci. Oct. 2014, 15, 18967-18984.

Zou, et al. Preparation of Activated Carbons from Chinese Coal and Hydrolysis Lignin. Adsorption Science & Technology. 2001; 19(1): 59-72.

Barakat, A. et al., Mechanical pretreatments of lignocellulosic biomass: towards facile and environmentally sound technologies for biofuels production, RCS Adv., vol. 4, (2014):48109-48127.

Lamsal, B. et al., Extrusion as a thermo-mechanical pre-treatment for lignocellulosic ethanol, Biomass and Bioenergy, col. 34, 12 (2010):1703-1710.

European Patent Application No. 15866602.4 Office Action dated Nov. 7, 2023.

\* cited by examiner

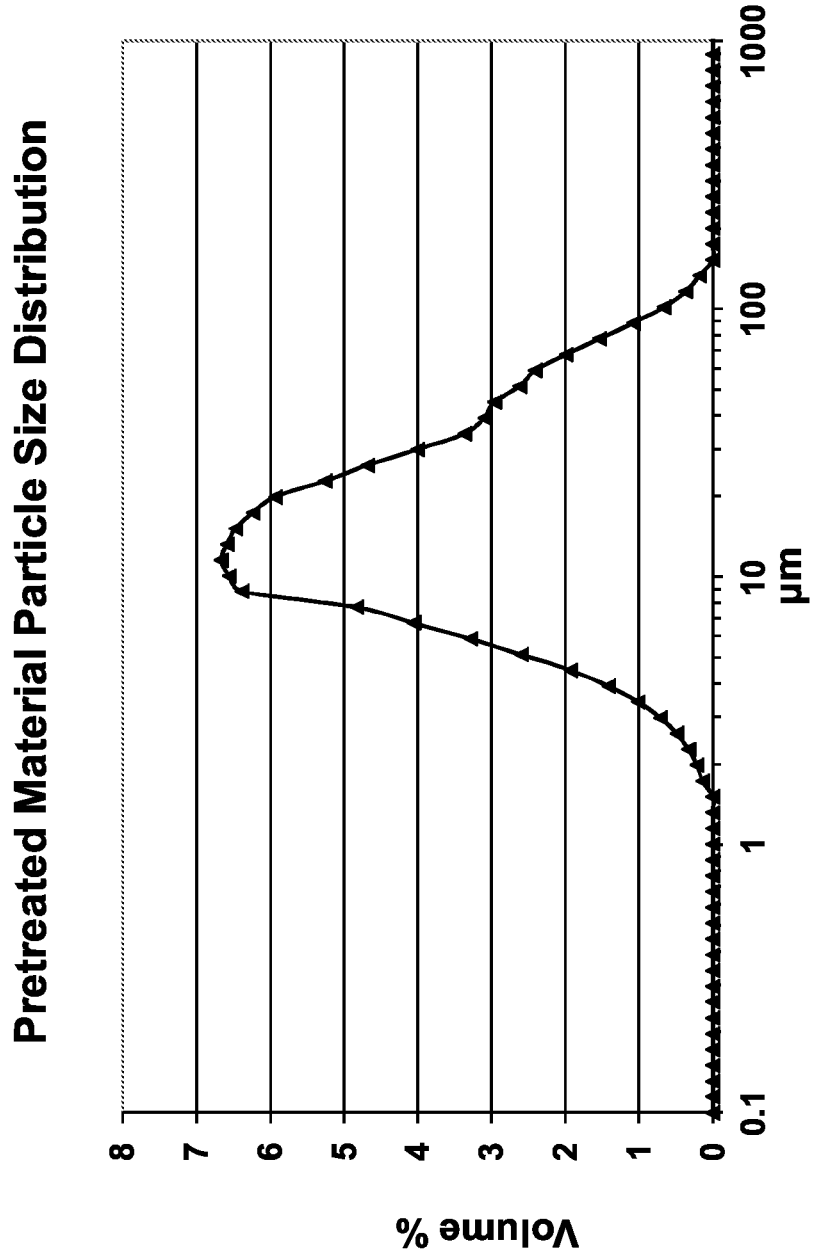

RAPID PRETREATMENT

CROSS-REFERENCE

This application is a continuation application of U.S. patent application Ser. No. 17/076,269, filed Oct. 21, 2020, which is a divisional application of U.S. patent application Ser. No. 14/971,481, filed Dec. 16, 2015, now U.S. Pat. No. 10,844,413, which is continuation application of International Application PCT/US15/64850, with an international filing date of Dec. 9, 2015, which claims the benefit of U.S. Provisional Application No. 62/089,704, filed Dec. 9, 2014, each of which is incorporated herein by reference in its entirety.

BACKGROUND

In the production of pretreatment end-products from biomass, it is useful to carry out the pretreatment hydrolysis reactions as quickly and efficiently as possible. A major problem with hydrolysis of carbohydrate polymers and separation from lignin can be the potential to produce various byproducts that inhibit the later enzymatic attack on the cellulose or the fermentation of the resulting sugars. The risk of inhibitor formation and loss of desirable carbohydrates can increase as the pretreatment period lengthens. Furthermore, the energy requirements of a longer pretreatment time can increase the cost of the process.

Increased inhibitors can also raise costs due to prolonged enzymatic hydrolysis and fermentation times, and can affect yields of fermentation end-products. However, decreased pretreatment hydrolysis periods can mean incomplete separation of carbohydrates from lignins and proteinaceous materials. Further, the resulting incomplete hydrolysis of crystalline cellulose can reduce the carbohydrate available for enzymatic hydrolysis and further fermentation into desirable end-products. Such decreased yields of carbohydrate and subsequent products of fermentation can make the whole process of biomass utilization more expensive.

Methods and systems for pretreatment have typically involved treating the biomass under pressure and heat, with or without acid or alkali over long periods that can be an hour or more. Thus, a more rapid procedure that can process biomass efficiently is needed to reduce the costs of not only the pretreatment process, but also that of enzymatic hydrolysis and subsequent fermentation.

SUMMARY

In a first aspect, disclosed herein are industrial scale methods for pretreating at least one dry ton of biomass per day, the methods comprising: (a) feeding the biomass at a rate of at least one dry metric ton (MT) of biomass per day into an extrusion system comprising a barrel defining an inner chamber comprising a feeder zone and a reaction zone; and (b) treating the biomass at an elevated temperature and pressure within the reaction zone for less than about 20 seconds to produce a pretreated biomass composition comprising a liquid fraction comprising monosaccharides and solid particles comprising cellulose.

In some embodiments, the extrusion system further comprises one or more rotatable screws configured to move the biomass through the extrusion system from the feeder zone and through the reaction zone. In some embodiments, the one or more rotatable screws comprise one or more sections that are configured to form one or more plugs from the biomass to separate the inner chamber into two or more zones, including the feeder zone and the reaction zone. Some embodiments comprise one, two, or three rotatable screws. Some embodiments comprise two rotatable screws.

In some embodiments, the rate of biomass feeding is at least about 2 dry MT/day, 3 dry MT/day, 4 dry MT/day, 5 dry MT/day, 7.5 dry MT/day, 10 dry MT/day, 15 dry MT/day, 20 dry MT/day, 25 dry MT/day, 50 dry MT/day, 75 dry MT/day, dry 100 MT/day, 150 dry MT/day, or 200 dry MT/day.

Some embodiments further comprise adding a liquid to the biomass prior to the reaction zone. In some embodiments, the liquid is water. In some embodiments, the liquid is added in the feeder zone through one or more sealable ports on the barrel. In some embodiments, the liquid is added to increase the moisture content of the biomass to from about: 10-90%, 15-85%, 20-80%, 30-70%, or about 40-60% w/v.

In some embodiments, the biomass is treated for less than 19, 18, 17, 16, 15, 14, 13, 12, 10, 9, 8, 7, 6, 5, 4, 3, 2, or 1 seconds in the reaction zone. In some embodiments, the biomass is treated for about 5 to 15 seconds in the reaction zone.

In some embodiments, the elevated temperature is about: 50-500° C., 75-400° C., 100-350° C., 150-300° C., or 200-250° C. In some embodiments, the elevated temperature is about 150-300° C.

In some embodiments, the elevated pressure is about: 50-1000 PSI, 100-750 PSI, 200-600 PSI, 300-500 PSI or 350-450 PSI. In some embodiments, the elevated pressure is about 300-500 PSI.

Some embodiments further comprise injecting steam into the biomass to increase temperature and pressure. In some embodiments, the steam is injected in the reaction zone. In some embodiments, the steam is injected through one or more sealable ports in the barrel.

Some embodiments further comprise adding a chemical agent to the biomass in the reaction zone. In some embodiments, the chemical agent comprises an acid, a base, or a combination thereof. In some embodiments, the chemical agent comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. In some embodiments, the chemical agent comprises the acid that is sulfuric acid. In some embodiments, the chemical agent is added to a level of about: 0.1-20% w/v, 1-15% w/v, 1.5-10% w/v, 1-10% w/v, 1-5% w/v, or 2-4% w/v. In some embodiments, the chemical agent is added to a level of about 2-4% w/v.

In some embodiments, the liquid fraction comprises C5 monosaccharides in at least a 50%, 55%, 60%, 65%, 70%, 75%, 80%, 85%, 90%, 95%, 96%, 97%, 98%, or 99% yield compared to the theoretical maximum based on the biomass. In some embodiments, the liquid fraction comprises C5 monosaccharides in at least a 70% yield compared to the theoretical maximum based on the biomass.

In some embodiments, the liquid fraction comprises C6 monosaccharides less than a 50%, 45%, 40%, 35%, 30%, 25%, 20%, 15%, 10%, or 5% yield compared to the theoretical maximum based on the biomass. In some embodiments, the liquid fraction comprises C6 monosaccharides less than a 35% yield compared to the theoretical maximum based on the biomass.

In some embodiments, the solid particles have a size range of about: 1-500 μm, 1-250 μm, 1-200 μm, or 1-150 μm. In some embodiments, the solid particles have an average size of about 15-25 μm.

In some embodiments, the method produces low levels of one or more inhibitor compounds. In some embodiments, the one or more inhibitor compounds comprise formic acid, acetic acid, hydroxymethyl furfural (HMF), furfural, or a combination thereof. In some embodiments, less than 30, 25, 20, 15, 10, or 5 kg of formic acid is produced per MT of dry biomass. In some embodiments, less than 100, 80, 60, 50, 40, 30, 25, 20, 15, 10, or 5 kg of acetic acid is produced per MT of dry biomass. In some embodiments, less than 20, 15, 10, 7.5, 5, 4, 3, 2, or 1 kg of hydroxymethyl furfural (HMF) is produced per MT of dry biomass. In some embodiments, less than 20, 15, 10, 7.5, 5, 4, 3, 2, or 1 kg of furfural is produced per MT of dry biomass.

In some embodiments, the biomass comprises algae, corn, grass, straw, grain hulls, wood, bark, sawdust, paper, poplars, willows, switchgrass, alfalfa, prairie bluestem, sugar palms, nypa palm, cassava, milo, sorghum, sweet potatoes, molasses, tubers, roots, stems, sago, cassaya, tapioca, rice peas, beans, potatoes, beets, fruits, pits, sorghum, sugar cane, rice, wheat, whole grains, rye, barley, bamboo, seeds, oats, or a combination thereof, or a derivative or byproduct thereof. In some embodiments, the derivative or byproduct thereof comprises corn stover, corn cobs, corn mash, corn fiber, silage, bagasse, distiller's grains, distiller's dried solubles, distiller's dried grains, condensed distiller's solubles, distiller's wet grains, distiller's dried grains with solubles, fiber, fruit peels, rice straw, rice hulls, wheat straw, barley straw, seed hulls, oat hulls, food waste, municipal sewage waste, or a combination thereof. In some embodiments, the biomass comprises a woody biomass.

Some embodiments further comprise hydrolyzing the solid particles comprising cellulose with one or more enzymes to produce monosaccharides.

Also provided herein are pretreated biomass compositions produced by any of the methods disclosed herein.

Also provided are sugar streams comprising C6 monosaccharides produced the enzymatic hydrolysis of the solid particles produced by any of the methods disclosed herein.

In a second aspect, disclosed herein are systems for industrial scale pretreatment of at least one dry ton of biomass per day, the systems comprising: (a) a barrel defining an inner chamber and comprising an inlet port near of first end of the barrel and an end flange plate at a second end of the barrel; (b) one or more rotatable screws configured to move the biomass through the inner chamber of the barrel and containing one or more sections configured to form one or more plugs from the biomass to separate the inner chamber of the barrel into two or more zones, including a feeder zone and a reaction zone; and (c) a pressure actuated discharge valve connected to the end flange plate and configured to open and close in response to pressure within the barrel, thereby allowing for continuous production of a pretreated biomass composition comprising a liquid fraction comprising monosaccharides and solid particles comprising cellulose.

Some embodiments comprise one, two, or three rotatable screws. Some embodiments comprise two rotatable screws.

Some embodiments further comprise a motor configured to rotate the one or more rotatable screws. In some embodiments, the motor is configured to rotate the one or more rotatable screws at about: 100, 250, 400, 500, 750, 1000, 1100, 1250, 1500, or 2000 RPMs.

In some embodiments, the system is capable of processing biomass at a rate at least about 2 dry MT/day, 3 dry MT/day, 4 dry MT/day, 5 dry MT/day, 7.5 dry MT/day, 10 dry MT/day, 15 dry MT/day, 20 dry MT/day, 25 dry MT/day, 50 dry MT/day, 75 dry MT/day, 100 dry MT/day, 150 dry MT/day, or 200 dry MT/day.

In some embodiments, the system further comprises a hopper connected to the inlet port for feeding the biomass into the feeder zone. In some embodiments, the hopper further comprises a feeder configured to move the biomass from the hopper through the inlet port. In some embodiments, the feeder is a delivery auger configured to distribute the biomass evenly into the feeder zone. In some embodiments, the hopper comprises one or more sealable ports configured to add a liquid to biomass in the hopper.

In some embodiments, the barrel further comprises one or more sealable ports configured to add liquid to biomass in the feeder zone.

In some embodiments, the rotatable screws are capable of conveying biomass through the reaction zone in less than about: 20, 19, 18, 17, 16, 15, 14, 13, 12, 10, 9, 8, 7, 6, 5, 4, 3, 2, or 1 seconds. In some embodiments, the rotatable screws are capable of conveying biomass through the reaction zone in about 5 to 15 seconds.

In some embodiments, the barrel further comprises one or more sealable ports configured to add steam to the reaction zone. In some embodiments, the barrel further comprises a heat jacket.

In some embodiments, the system is configured to maintain an elevated temperature in the reaction zone. In some embodiments, the elevated temperature is provided by steam, a heat jacket, or a combination thereof. In some embodiments, the elevated temperature is about: 50-500° C., 75-400° C., 100-350° C., 150-300° C., or 200-250° C.

In some embodiments, the system is configured to maintain an elevated pressure in the reaction zone. In some embodiments, the elevated pressure is maintained by addition of steam, liquid, biomass, or a combination thereof. In some embodiments, the elevated pressure is about: 50-1000 PSI, 100-750 PSI, 200-600 PSI, 300-500 PSI or 350-450 PSI.

In some embodiments, the barrel further comprises one or more sealable ports configured to add one or more chemical agents to the reaction zone. In some embodiments, the chemical agent comprises an acid, a base, or a combination thereof.

In some embodiments, the pressure actuated discharge valve comprises a poppet valve, a ball valve, a check valve, or a rotating knife-gate valve. In some embodiments, the pressure actuated discharge valve comprises a poppet valve.

In some embodiments, the pressure actuated discharge valve is connected to an actuator. In some embodiments, the actuator is a pneumatic actuator, a hydraulic actuator, an electro-mechanical actuator, or a combination thereof.

In some embodiments, the actuator is operably coupled to a back pressure control unit. In some embodiments, the back pressure control unit is operably coupled to one or more pressure gauges. In some embodiments, the one or more pressure gauges monitor pressure in the barrel via one or more sealable ports in the barrel. In some embodiments, at least one of the one or more pressure gauges is configured to monitor pressure within the reaction zone.

In some embodiments, the barrel further comprises one or more ports comprising a temperature gauge, a pressure gauge, or a combination thereof.

In some embodiments, the system further comprises a flash tank. In some embodiments, the flash tank collects the pretreated biomass composition as it exits the pressure actuated discharge valve.

In some embodiments, the system is configured to produce the liquid fraction comprising C5 monosaccharides in at least a 70% yield compared to the theoretical maximum based on the biomass.

In some embodiments, the system is configured to produce the liquid fraction comprising C6 monosaccharides in less than a 35% yield compared to the theoretical maximum based on the biomass.

In some embodiments, the system is configured to produce the solid particles in a size range of about: 1-500 µm, 1-250 µm, 1-200 µm, or 1-150 µm.

In some embodiments, the system is configured to produce the solid particles in an average size of about 15-25 µm.

In some embodiments, the biomass comprises a woody biomass.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent that a term incorporated by reference conflicts with a term defined herein, this specification shall control.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13 is a graph showing the particle size distribution of Cherry sawdust biomass following pretreatment according to an embodiment of the methods disclosed herein.

DETAILED DESCRIPTION

Figure 1:
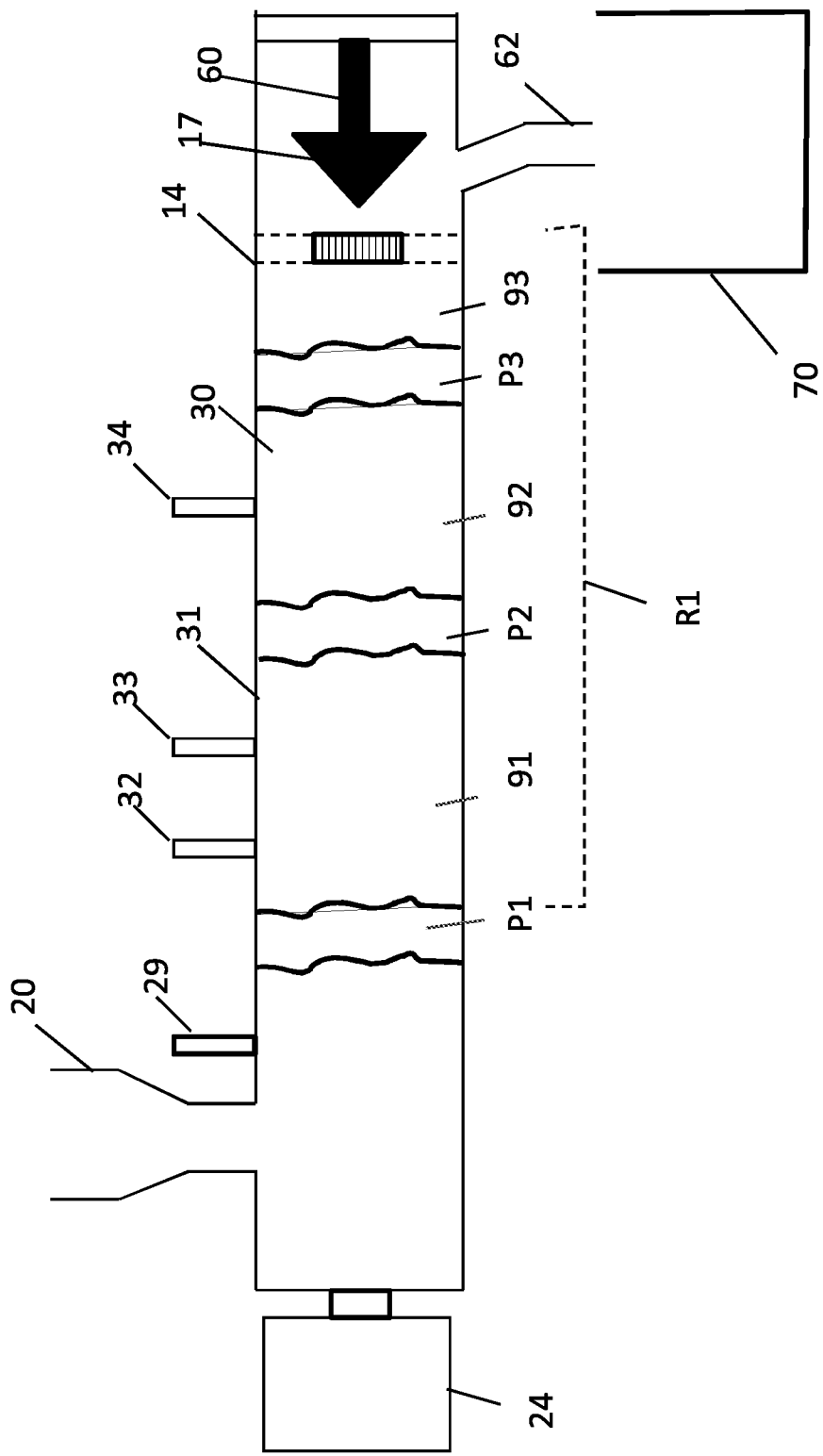
FIG. 1 is a schematic diagram of one embodiment of an apparatus for use in the present invention.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

In this specification and in the claims that follow, reference will be made to a number of terms which shall be defined to have the following meanings. Unless characterized otherwise, technical and scientific terms used herein have the same meaning as commonly understood by one of ordinary skill in the art.

Definitions

Unless characterized otherwise, technical and scientific terms used herein have the same meaning as commonly understood by one of ordinary skill in the art.

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

"About" means a referenced numeric indication plus or minus 10% of that referenced numeric indication. For example, the term about 4 would include a range of 3.6 to 4.4.

Fermentation is an anaerobic chemical process by which molecules such as glucose and xylose are broken down to release energy and fermentation end products are synthesized. Industrial fermentation processes begin with suitable microorganisms, such as yeasts and bacteria, and specified conditions, such as careful adjustment of nutrient concentration. The products are of many types: alcohols, glycerol, and carbon dioxide from yeast fermentation of various sugars; butyl alcohol, acetone, lactic acid, monosodium glutamate, and acetic acid from various bacteria; and citric acid, gluconic acid, and small amounts of antibiotics, vitamin B12, and riboflavin (vitamin B2) from mold fermentation. Ethyl alcohol and/or butanol are produced via the fermentation of starch or sugar and are important sources of liquid biofuel.

"Fermentive end-product" and "fermentation end-product" are used interchangeably herein to include biofuels, chemicals, compounds suitable as liquid fuels, gaseous fuels, triacylglycerols (TAGs), reagents, chemical feedstocks, chemical additives, processing aids, food additives, bioplastics and precursors to bioplastics, and other products. Examples of fermentive end-products include but are not limited to 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl) butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-) ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl) pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl) pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hex ene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl) hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4- hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanol, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal. undecanoate, n-dodecane, 1-dodecene, 1-dodecanol, dodecanal, dodecanoate, n-dodecane, 1-decadecene, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, glycerol, fucoidan, iodine, chlorophyll, carotenoid, calcium, magnesium, iron, sodium, potassium, phosphate, lactic acid, acetic acid, formic acid, isoprenoids, and polyisoprenes, including rubber. Further, such products can include succinic acid, pyruvic acid, enzymes such as cellulases, polysaccharases, lipases, proteases, ligninases, and hemicellulases and may be present as a pure compound, a mixture, or an impure or diluted form.

Fermentation end-products can also include polyols or sugar alcohols; for example, methanol, glycol, glycerol, erythritol, threitol, arabitol, xylitol, ribitol, mannitol, sorbitol, dulcitol, fucitol, iditol, inositol, volemitol, isomalt, maltitol, lactitol, and/or polyglycitol.

The term "pH modifier" as used herein has its ordinary meaning as known to those skilled in the art and can include any material that will tend to increase, decrease or hold steady the pH of the broth or medium. A pH modifier can be an acid, a base, a buffer, or a material that reacts with other materials present to serve to raise, lower, or hold steady the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. In one embodiment, a buffer can be produced in the broth or medium or separately and used as an ingredient by at least partially reacting in acid or base with a base or an acid, respectively. When more than one pH modifiers are utilized, they can be added at the same time or at different times. In one embodiment, one or more acids and one or more bases are combined, resulting in a buffer. In one embodiment, media components, such as a carbon source or a nitrogen source serve as a pH modifier; suitable media components include those with high or low pH or those with buffering capacity. Exemplary media components include acid- or base-hydrolyzed plant polysaccharides having residual acid or base, ammonia fiber explosion (AFEX) treated plant material with residual ammonia, lactic acid, corn steep solids or liquor.

The term "plant polysaccharide" as used herein has its ordinary meaning as known to those skilled in the art and can comprise one or more polymers of sugars and sugar derivatives as well as derivatives of sugar polymers and/or other polymeric materials that occur in plant matter. Exemplary plant polysaccharides include cellulose, starch, pectin, and hemicellulose. Others are chitin, sulfonated polysaccharides such as alginic acid, agarose, carrageenan, porphyran, furcellaran and funoran. Generally, the polysaccharide can have two or more sugar units or derivatives of sugar units. The sugar units and/or derivatives of sugar units can repeat in a regular pattern, or otherwise. The sugar units can be hexose units or pentose units, or combinations of these. The derivatives of sugar units can be sugar alcohols, sugar acids, amino sugars, etc. The polysaccharides can be linear, branched, cross-linked, or a mixture thereof. One type or class of polysaccharide can be cross-linked to another type or class of polysaccharide. The concentration of saccharides in a biomass containing plant polysaccharides such as cellulose, hemicellulose, starch, or pectin can be given in terms of monosaccharide equivalents. A monosaccharide equivalent concentration is the concentration of saccharides assuming complete hydrolysis of polysaccharides to monosaccharides.

The term "saccharification" as used herein has its ordinary meaning as known to those skilled in the art and can include conversion of plant polysaccharides to lower molecular weight species that can be utilized by the organism at hand. For some organisms, this would include conversion to monosaccharides, disaccharides, trisaccharides, and oligosaccharides of up to about seven monomer units, as well as similar sized chains of sugar derivatives and combinations of sugars and sugar derivatives.

The term "biomass" as used herein has its ordinary meaning as known to those skilled in the art and can include one or more biological materials that can be converted into a biofuel, chemical or other product. Biomass as used herein is synonymous with the term "feedstock" and includes corn syrup, molasses, silage, agricultural residues (corn stalks, grass, straw, grain hulls, fibers, bagasse, etc.), animal waste (manure from cattle, poultry, and hogs), Distillers Dried Solubles (DDS), Distillers Dried Grains (DDG), Condensed Distillers Solubles (CDS), Distillers Wet Grains (DWG), Distillers Dried Grains with Solubles (DDGS), woody materials (wood or bark, sawdust, timber slash, and mill scrap), municipal waste (waste paper, recycled toilet papers, yard clippings, etc.), and energy crops (poplars, willows, switchgrass, *Miscanthus* sp., alfalfa, prairie bluestem, algae, including macroalgae, etc.). One exemplary source of biomass is plant matter. Plant matter can be, for example, woody plant matter, including softwoods or hardwoods, non-woody plant matter, cellulosic material, lignocellulosic material, hemicellulosic material, carbohydrates, pectin, starch, inulin, fructans, glucans, corn, sugar cane, grasses such as rice, corn, barley, wheat, switchgrass, sorghum, high biomass sorghum, bamboo or the like, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can also include plant cell culture or plant cell tissue culture. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, meat, fat, animal processing waste, and animal waste. "Feedstock" is frequently used to refer to biomass being used for a process, such as those described herein.

Biomass can be derived from agricultural crops, crop residues, trees, woodchips, sawdust, paper, cardboard, grasses, algae, municipal waste and other sources as described supra. In one embodiment, the biomass contains cellulosic, hemicellulosic, and/or lignocellulosic material. In one embodiment the biomass is woody (poplar, Eucalyptus, willow, pine, etc.). In another embodiment, the biomass is non-woody plant material, such as grasses, dicots, monocots, etc. Other biomasses include algal biomass, nonvascular plant biomass, and processed materials derived from plants; e.g., hulls, distiller's grains, municipal sewage waste, and the like.

In one embodiment, a biomass composition comprising cellulose, hemicellulose, and/or lignocellulose comprises alfalfa, algae, bagasse, bamboo, corn stover, corn cobs, corn fiber, corn kernels, corn mash, corn steep liquor, corn steep solids, distiller's grains, distiller's dried solubles, distiller's dried grains, condensed distiller's solubles, distiller's wet grains, distiller's dried grains with solubles, eucalyptus, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof.

The term "dry weight" of biomass is meant the weight of the biomass having all or essentially all water removed. Dry weight is typically measured according to American Society for Testing and Materials (ASTM) Standard E1 756-01 (Standard Test method for Determination of Total Solids in Biomass) or Technical Association of the Pulp and Paper Industry, Inc. (TAPPI) Standard T-412 om-02 (Moisture in Pulp, Paper and Paperboard).

The term "productivity" as used herein has its ordinary meaning as known to those skilled in the art and can include the mass of a material of interest produced in a given time in a given volume. Units can be, for example, grams per liter-hour, or some other combination of mass, volume, and time. In fermentation, productivity is frequently used to characterize how fast a product can be made within a given fermentation volume. The volume can be referenced to the total volume of the fermentation vessel, the working volume of the fermentation vessel, or the actual volume of broth being fermented. The context of the phrase will indicate the meaning intended to one of skill in the art. Productivity is different from "titer" in that productivity includes a time term, and titer is analogous to concentration. Titer and Productivity can generally be measured at any time during the fermentation, such as at the beginning, the end, or at some intermediate time, with titer relating the amount of a particular material present or produced at the point in time of interest and the productivity relating the amount of a particular material produced per liter in a given amount of time. The amount of time used in the productivity determination can be from the beginning of the fermentation or from some other time, and go to the end of the fermentation, such as when no additional material is produced or when harvest occurs, or some other time as indicated by the context of the use of the term. "Overall productivity" refers to the productivity determined by utilizing the final titer and the overall fermentation time.

The term "biocatalyst" as used herein has its ordinary meaning as known to those skilled in the art and can include one or more enzymes and/or microorganisms, including solutions, suspensions, and mixtures of enzymes and microorganisms. In some contexts this word will refer to the possible use of either enzymes or microorganisms to serve a particular function, in other contexts the word will refer to the combined use of the two, and in other contexts the word will refer to only one of the two. The context of the phrase will indicate the meaning intended to one of skill in the art. For example, a biocatalyst can be a fermenting microorganism. The term biocatalyst includes fermenting microorganisms such as yeast, bacteria, or algae.

The terms "conversion efficiency" or "yield" as used herein have their ordinary meaning as known to those skilled in the art and can include the mass of product made from a mass of substrate. The term can be expressed as a percentage yield of the product from a starting mass of substrate. For the production of ethanol from glucose, the net reaction is generally accepted as:

$$C_6H_{12}O_6 \rightarrow C_2H_5OH + 2CO_2$$

and the theoretical maximum conversion efficiency, or yield, is 51% (wt.). Frequently, the conversion efficiency will be referenced to the theoretical maximum, for example, "80% of the theoretical maximum." In the case of conversion of glucose to ethanol, this statement would indicate a conversion efficiency of 41% (wt.). The context of the phrase will indicate the substrate and product intended to one of skill in the art.

"Pretreatment" or "pretreated" is used herein to refer to any mechanical, chemical, thermal, biochemical process or combination of these processes whether in a combined step or performed sequentially, that achieves disruption or expansion of the biomass so as to render the biomass more susceptible to attack by enzymes and/or microbes. In one embodiment, pretreatment includes removal or disruption of lignin so as to make the cellulose and hemicellulose polymers in the plant biomass more available to cellulolytic enzymes and/or microbes, for example, by treatment with acid or base. In one embodiment, pretreatment includes disruption or expansion of cellulosic and/or hemicellulosic material. Chemical pretreatment processes include, but are not limited to, bleaching, oxidation, reduction, acid treatment, base treatment, sulfite treatment, acid sulfite treatment, basic sulfite treatment, ammonia treatment, and hydrolysis. Thermal pretreatment processes include, but are not limited to, sterilization, ammonia fiber expansion or explosion ("AFEX"), steam explosion, holding at elevated temperatures, pressurized or unpressurized, in the presence or absence of water, and freezing. Biochemical processes include, but are not limited to, treatment with enzymes, including enzymes produced by genetically-modified plants, and treatment with microorganisms. Various enzymes that can be utilized include cellulase, amylase, β-glucosidase, xylanase, gluconase, and other polysaccharases; lysozyme; laccase, and other lignin-modifying enzymes; lipoxygenase, peroxidase, and other oxidative enzymes; proteases; and lipases. One or more of the mechanical, chemical, thermal, thermochemical, and biochemical processes can be combined or used separately. Such combined processes can also include those used in the production of paper, cellulose products, microcrystalline cellulose, and cellulosics and can include pulping, Kraft pulping, acidic sulfite processing. The feedstock can be a side stream or waste stream from a facility that utilizes one or more of these processes on a biomass material, such as cellulosic, hemicellulosic or lignocellulosic material. Examples include paper plants, cellulosics plants, distillation plants, cotton processing plants, and microcrystalline cellulose plants. The feedstock can also include cellulose-containing or cellulosic containing waste materials. The feedstock can also be biomass materials, such as wood, grasses, corn, starch, or saccharide, produced or harvested as an intended feedstock for production of ethanol or other products such as by biocatalysts.

Pretreatment of the biomass composition can be performed such that any solids are reduced in size. Reducing the size of solids in the biomass composition can be advantageous because smaller particles have larger surface area to volume ratios. Increasing the ratio of surface area to volume can be advantageous because it can, for example, increase the rate of particle wetting (e.g., with water or a chemical agent such as an acid or a base), increase the accessibility of enzymes to the polysaccharides in the biomass, enable the use of a smaller dose of enzymes during a hydrolysis of the biomass, enable the use of fewer or lower amounts of chemicals (e.g., acids or bases) during a pretreatment and/or hydrolysis step, enable the use of weaker acids or bases in a pretreatment or hydrolysis step, enable the use of higher concentrations of solids in any further processing step (e.g., during a hydrolysis step), and/or increase the yield of saccharides from the hydrolysis of the biomass.

Biomass compositions can be reduced in size to a mixture of particles having a uniform, or substantially uniform, size. Such mixtures can be referred to as homogeneous mixtures. Homogeneous mixtures of particles can have many advantages over mixtures of particles having heterogeneous sizes with respect to further pretreatment processes and/or during hydrolysis to produce saccharide streams. For example, heterogeneous mixtures of particles can experience uneven heating during thermal and thermochemical processing steps. Uneven heating can lead to overcooking (e.g., charring/burning) of particles and/or undercooking of particles. Charring or burning of particles can reduce the yield of saccharide from the hydrolysis of the particles; this can be due to degradation or denaturation of saccharide polymers such as starch, hemicellulose, and/or cellulose. Undercooking of particles can lead to unhydrolyzed saccharide polymers (e.g., starch, hemicellulose, cellulose) during enzymatic or chemical hydrolysis, which can also reduce the yield of saccharide. In contrast, uniform heating, wetting, chemical treatment (e.g., acid or base treatment), and/or enzyme hydrolysis can be achieved with mixtures of particles having uniform sizes (e.g., homogeneous mixtures).

"Sugar compounds", "sugar streams", "saccharide compounds", or "saccharide streams" is used herein to indicate mostly monosaccharide sugars, dissolved, crystallized, evaporated, or partially dissolved, including but not limited to hexoses and pentoses; sugar alcohols; sugar acids; sugar amines; compounds containing two or more of these linked together directly or indirectly through covalent or ionic bonds; and mixtures thereof. Included within this description are disaccharides; trisaccharides; oligosaccharides; polysaccharides; and sugar chains, branched and/or linear, of any length. A sugar stream can consist of primarily or substantially C6 sugars, C5 sugars, or mixtures of both C6 and C5 sugars in varying ratios of said sugars. C6 sugars have a six-carbon molecular backbone and C5 sugars have a five-carbon molecular backbone. The terms "sugar" and "saccharide" are used interchangeably herein.

A "liquid" or "aqueous" composition may contain solids and a "solids" composition may contain liquids. A liquid composition refers to a composition in which the material is primarily liquid, and a solids composition is one in which the material is primarily solid.

The term "kPa" refers to kilopascal, a unit of pressure. Standard atmospheric pressure, the pressure exerted by a 10 g mass resting on a 1 cm$^2$ area, is defined as 101.325 kPa. The term "psi" or "PSI" refers to pound-force per square inch. It is the pressure resulting from a force of one pound-force applied to an area of one square inch.

Description

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

Disclosed herein are methods for efficient, rapid treatment of biomass using high biomass concentration conditions. Unlike present methods, which can retain biomass materials in a chamber for a long period of time, it has been discovered that processing of these materials can avoid long retention times under thermal and chemical treatment, thereby avoiding the degradation of C5 sugars, proteins and lignins into undesirable products such as HMF and furfurals, while allowing the separation of carbohydrate materials, both monomeric and polymeric sugars, from other biomass components. The inhibitors usually formed during pretreatment are acetic acid (formed during the release of C5 sugars) and also formic acid, furfural and HMF. Formation of the latter three compounds is largely dependent on the temperature, pressure and biomass residence time during pretreatment.

Further, it has been discovered that the solubilization of crystalline cellulose is not impeded by the short exposure time. These methods can also allow biomass to be heated and pressurized uniformly for improved access of treatment reactants to the biomass. During this process, plugs can be produced that shear the biomass into smaller particles and further increase access of reactants to hydrolyze and release the C5 polymers while also releasing and solubilizing the C6 polymers. In one embodiment, the biomass is moved through a reaction zone wherein steam and pressure are applied, followed by the addition of acid, and finally release of the material to atmospheric pressure by a rapidly opening and closing an end valve. The whole process happens within seconds, resulting in a thermo-mechanical and chemically-hydrolyzed biomass with lower or reduced levels of inhibitors as compared to pretreatment methods known in the art.

In some cases, the pretreatment methods provided herein permit the release and depolymerization of sugars in a rapid time frame. The sugars can be released and depolymerized a within a very short period of time. The period of time can be less than 20 second. Generally, the time in the reaction zone can range from a second to less than 20 seconds. This provides continuously moving biomass through the tube resulting in a rapidly-pretreated biomass containing few, no, or substantially no inhibitors.

Described herein are improved, low cost, energy-efficient pretreatment devices and methods for the rapid processing of lignocellulose, cellulose, hemicellulose, and the like biomass materials prior to enzymatic hydrolysis, which includes a thermo-mechanical treatment with or without chemicals and a reaction extrusion controlled by a pressure-driven variable end valve. The methods disclosed herein can include the use of a device that comprises a cylindrical chamber divided into tubular zones, wherein biomass can be moved either continuously or in batches through the cylindrical chamber; reduced in size; and treated with pressure, heat, chemicals, or a combination thereof in the different tubular zones prior to being subjected to a rapid difference in temperature and pressure (e.g., explosive decompression). The biomass can be moved by screw-type mechanism, such as a single, twin, or even triple screw as found in an extruder. Alternatively, the biomass can be moved by a mechanism such as a block or other mechanical pressure, differential hydrostatic pressure managed by air, oil, piston, vacuum, or gravity. These mechanisms can also have a function for pushing or driving forward or separating the biomass into chambers or zones for particular treatment or addition of materials.

In general, an extruder for use in this system includes an elongated barrel presenting a material inlet and a material outlet adjacent opposed ends thereof, with one or more elongated, axially rotatable screw(s) within the barrel which serves to advance the material from the inlet end to the outlet end thereof. The screw is designed to smooth the flow of material while reducing it in size and various screw elements are arranged to increase or decrease the flow, or to form plugs of the biomass within the barrel. The screw(s) coupled with an end valve under pressure at the outlet, control the speed, pressure, and partly the temperature applied to the biomass as it moves through and out of the barrel.

It will be understood by those skilled in the art that various methods of processing biomass can be employed that are modified to include the herein described rapid treatment and hydrolysis to produce high levels of carbohydrates with low levels of inhibitors. For example the tube method of Andritz (US2014/0034260 A1) can be fitted with a separable inner chamber and the end valve process of this invention. The methods can be performed using a twin-screw extruder. Similarly, single or multiple screw extruders are adaptable to this method. Further, acid, alkali, or other chemicals can be used during pretreatment, or steam alone can be employed.

The systems and methods disclosed herein can be used for industrial scale pretreatment of biomass at a high rate of throughput. For example, it is estimated that biomass can move through and be processed in accordance with the following Table 1 by continuous operation of a twin screw extruder in accordance with some of the methods disclosed herein.

TABLE 1

| Screw Diameter | Dry Matter Throughput Dry Tons/Day |
|---|---|
| 30 mm | 3.3 |
| 52 mm | 17.0 |
| 92 mm | 94.4 |
| 124 mm | 231.1 |

In a general overview, the apparatus and its use in an extruder are described as follows. The barrel screw reactor can comprise a metal cylindrical barrel (which can be lined with specialty materials such as ceramic, glass, aluminum, hasteloy, titanium and the like) having a size that can range from, e.g., 30 mm to 220 mm diameter or larger equipped with one or more screws, oriented horizontally or vertically. The barrel can be divided into separate sections and can be equipped with multiple use ports along the top, side, and/or bottom surfaces. Such multiple use ports can be sealable ports. The multiple use ports can allow the injection of water, steam, acid or other chemicals. The multiple use ports can allow the insertion of thermocouples and/or pressure gauges for measurement of temperature and pressure inside the barrel. Additional ports can be added as required. The reactor barrel can be equipped with electric heating elements or a steam jacket for even heating of the barrel. Heating can alternatively or additionally be supplied by the injection of steam. The reactor barrel can be attached to a pipe that discharges into a flash tank or other container. The flash tank can be constructed using stainless steel. The barrel can be isolated from the flash tank by a pipe with a seat end having a pressure actuated discharge valve arrangement capable of continuously adjusting position depending upon the back pressure on the valve and the pressure within the system. The discharge valve arrangement can comprise a metal or ceramic sealing seat in between to allow for an explosive discharge of biomass. The pressure actuated valve arrangement can comprise a conical nozzle connected to a shaft (see in FIGS. 1 and 2). The diameter of the end valve can vary with the size of the machine, and typically ranges from 30 mm to 220 mm or larger. The conical nozzle can be connected to a shaft that is attached to an actuator in a backpressure generator. The actuator can provide the pneumatic pressure that is regulated by the backpressure generator, which monitors the pressure. The pressure can be a high pressure such that no backflow occurs and there is a restricted flow of material out of the tube. The backpressure on the conical nozzle and seat can be adjustable. For example, operations can be performed using 50 psi to 600 psi (gauge pressure) of backpressure onto the shaft connected to the conical nozzle of the end shear valve. The cone of the end shearing valve can travel between a fully closed and a fully open position, and any intermediate position. A pipe at the outlet of the end shear valve can direct the treated solids down into the bottom of the flash tank, where the solids and vapor can be separated and easily removed.

FIG. 1 shows an embodiment of one type of a design of a reactor as provided herein. The reactor can be a commercial scale reactor. It comprises a horizontal cylindrical barrel 31 fitted with twin screws (not shown) and a discharge valve 17 attached at a special end flange 14 at the second end of the barrel. The barrel can be insulated and can have impermeable walls. A motor 24 for moving the screws can be attached near the first end. The motor can be, e.g., an electrically-driven motor and gearbox combination, with or without pulleys and V-belts or any other mechanism to turn the screws. The motor can also be, for example and without being limiting, a synchronous torque motor. A hopper 20 can be attached to the inlet of the sealed end of the barrel 31. Biomass can be added through the opening of the hopper 20. The biomass can be any biomass as provided herein. There can be a feeder for non-compacting or compacting flow generation (not shown) such as a crammer to control biomass addition from the hopper 20 to the barrel 31. The compacting and/or non-compacting feeder can be any compacting and/or non-compacting loader known in the art. For example, a non-compacting flow inducing feeder can be a non-compacting feeder or various types of live-bottom bin flow inducers followed by flow metering conveyors such as various types of drag chains, bucket elevators, or rotating helixes. In its simplest form a non-compacting feeder can refer to loading biomass by hand into an open first end of the cylindrical barrel. Compacting feeders can comprise mechanical compaction. Mechanical compaction can be achieved by provision of a mechanical compaction device such as a reciprocating plunger or screw feeder. The barrel 31 can have a first sealable port 29 for adding water to hydrate the biomass in the tube as it moves away from the hopper end. The screws can be designed with sections to form a high-shear plug P1, which can occur after the addition of water but prior to the addition of steam through the ports 32 and 33. The high shear plug P1 can break the biomass into smaller-sized particles (e.g., of about 10 to 200 microns). The plugs that are formed can separate the biomass into sections or zones that can be treated differently from one another. Movement of the screws through the impermeable barrel chamber 30 pushes the biomass and water mixture from the feeder zone into a first zone 91. Ports 32, 33 add pressurized steam (e.g., to about 300 psi to 600 psi) to the barrel after the first plug is formed, increasing the barrel pressure to a desired temperature and pressure (for example, 600 psi and a temperature of 253° C.). A second plug P2 can be formed prior to the addition of aqueous acid (or other chemical, e.g., a base) and can separate the material into a second zone 92. In this second zone, C6 polymers can be solubilized and/or C5 polymers can be hydrolyzed into monosaccharides. The thermo-mechanical conditions can be maintained in this zone. Following the acid (or alkali solution) addition through 34, a third plug P3 can be formed as the biomass moves through the cylindrical barrel chamber 30. The acid (or alkali solution) can also be added after the third plug is formed. Further solubilization of sugars can occur in this third zone 93 and, if needed, more water can be added through another port (not shown) in the third zone 93.

The end valve 17 at the far end of the third zone 93, when seated, comprises a part of the reaction zone R1. The end valve can be under constant pressure. A back pressure regulator (e.g., see FIGS. 11 and 12) can be added to the barrel cylinder 31 such that the back-pressure regulator monitors the pressure at the end of the zone 93. The monitoring can be continuous. The back pressure regulator acts to maintain a set pressure by opening and closing the end valve (e.g., on a continuous basis) 17 through a shaft 60 connected to an actuator (e.g., see FIGS. 12 and 13). The actuator can be any actuator as provided herein. For example, the actuator can be a pneumatic actuator. The valve activity can occur rapidly to open the end valve 17 and release pressurized material into a pipe 62 that leads to the open flash tank 70, thus blowing out the treated biomass and rapidly dropping the temperature and pressure from several hundred psi to atmospheric pressure. As the pressure drops, the back pressure regulator causes the actuator to close the end valve 17 via movement of the shaft 60. The pressure differential can be varied depending on the amount needed to further solubilize the C6 sugars. When operating at ideal conditions, the end valve 17 may never be completely closed and never be completely open, the shaft 60 moving back and forth under the control of the actuator.

In some cases, any device as provided herein comprises an actuator. The actuator can be controlled by a regulator. The actuator on a device as provided herein can be any type of mechanical, electro-mechanical, linear, piezoelectric, ultrasonic, hydraulic, electrohydraulic, pneumatic, segmented spindle, moving coil, or moving iron controllable actuator or motor known in the art. In some cases, the actuator in a device as provided herein comprises a pneumatic actuator. The pneumatic actuator can be a piston actuator. In some cases, the actuator in a device as provided herein comprises a hydraulic actuator. Examples of mechanical actuators can include, screw type actuators (e.g., leadscrew, screw jack, ball screw, or roller screw), wheel and axle (e.g., hoist, winch, rack and pinion, chain drive, belt drive, rigid chain, or rigid belt), piston actuators, diaphragm actuators, or cam actuators. A regulator for controlling an actuator in any device as provided herein can be a pressure regulator. The pressure regulator can be a back-pressure regulator. The pressure regulator (e.g., back-pressure regulator) can be a single stage regulator or double stage regulator. The pressure regulator can comprise a restricting element, a loading element, and a measuring element. The restricting element can be a valve such as a globe, butterfly or poppet valve. For precise control, a valve such as a linear globe can work well. Others types of valves can be a fast-opening globe, a ball, a butterfly, or an equal percentage globe valve.

The loading element can be a weight, a spring, or an actuator (e.g., piston or diaphragm actuator) in combination with a spring. In some cases, the pressure regulator in any device provided herein is a pneumatic pressure regulator. The pneumatic pressure regulator works with a modified poppet valve. For example, an E/P pressure regulator, series ED05 (Bosch Rexroth AG) can be used. In some cases, the pressure regulator in any device provided herein is a hydraulic pressure regulator. The pressure regulator can also be in communication and/or comprise a flow meter for measuring flow rates within a device as provided herein. The flow meter can be a flow meter, rotometer or mass flow controller known in the art.

The three cylindrical chambers (zones) 91, 92, and 93 within the barrel cylinder 31 and discharge pipe 62 through the valve to atmospheric pressure comprise the reaction zone R1 where pretreatment of the biomass occurs. Pretreatment of the biomass inputted into the barrel cylinder 31 occurs within the barrel chamber 30 as long as the material is at elevated temperatures and pressures, so the reaction zone R1 ends when the material is flashed to atmosphere. The thermochemical and mechanical pressure in this zone, as well as the residence time, can be varied in accordance with the type of biomass being pretreated. Those of skill in the art will recognize that biomass material with a high concentration of easily solubilized and hydrolyzed carbohydrate polymers could require less time and/or less pressure and temperature.

The residence time in the reaction zone can be very short as compared to other pretreatment systems known in the art. The residence time in a reaction zone (e.g., FIG. 1, R1) of a device as provided herein can be less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, 55, or 60 seconds. The residence time in a reaction zone (e.g., FIG. 1, R1) of a device as provided herein can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, 55, or 60 seconds. The residence time in a reaction zone (e.g., FIG. 1, R1) of a device as provided herein can be between about 1 second to about 2, about 1 second to about 3 seconds, about 1 second to about 4 seconds, about 1 second to about 5 seconds, about 1 second to about 6 seconds, about 1 second to about 7 seconds, about 1 second to about 8 seconds, about 1 second to about 9 seconds, about 1 second to about 10 seconds, about 1 second to about 15 seconds, about 1 to about 20 seconds, about 2 second to about 4 seconds, about 2 second, to about 6 second, about 2 seconds to about 8 second, about 2 second, to about 10 seconds, about 2 seconds to about 15 second, about 2 seconds to about 20 seconds, about 5 seconds to about 10 seconds, about 5 seconds to about 10 seconds, about 5 seconds to about 15 seconds, about 5 seconds to about 20 seconds, about 10 second to about 12 second seconds, about 10 seconds to about 14 seconds, about 10 seconds, to about 16 seconds, about 10 seconds to about 18 seconds, about 10 seconds to about 20 seconds, about 15 seconds to about 20 seconds, about 20 seconds to about 30 seconds, about 30 seconds to about 45 seconds, or about 45 seconds to about 60 seconds. The pressure can vary from 0 to 800 psi, preferably from 300-700 psi. The temperature range is wide, from 100 to 260° C. or more, preferably from 160-230° C. The temperature used often depends on the crystallinity of the cellulose fiber in the biomass; for example, softwood has a higher percent of crystalline cellulose and requires a temperature of 210-240° C. Acid may or may not be added to assist with the reaction and can range from 0 wt % of pure chemical per dry tonne of biomass to 8 wt % of pure chemical per dry tonne of biomass, preferably from 1 wt % to 5 wt %.

In another embodiment, biomass as provided herein can be pre-treated at an elevated temperature and/or pressure in a device as provided herein. In one embodiment, biomass is pre-treated at a temperature range of 20° C. to 400° C. In another embodiment biomass is pretreated at a temperature of about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., 400° C. or higher. In another embodiment, elevated temperatures are provided by the use of steam, hot water, or hot gases. In one embodiment steam can be injected into a biomass containing vessel or barrel chamber. In another embodiment the steam, hot water, or hot gas can be injected into a vessel jacket such that it heats, but does not directly contact the biomass. In an additional embodiment heat can be externally applied using electric barrel heaters.

In another embodiment, biomass as provided herein can be pre-treated at an elevated temperature and/or pressure in a device as provided herein. In one embodiment, biomass is pre-treated at a pressure range of from 0 to 800 PSI. In some embodiments, heating the biomass pretreated in a device as provided herein is performed at a pressure higher than atmospheric. The pressure can be from about 25 PSI to about 800 PSI. The pressure can be from about 300 PSI and 500 PSI. The pressure can be about 400 PSI. For example, the pressure can be about 25-800, 25-700, 25-600, 25-500, 25-250 PSI, 25-225 PSI, 25-200 PSI, 25-175 PSI, 25-150 PSI, 25-125 PSI, 25-100 PSI, 25-75 PSI, 25-50 PSI, 50-225 PSI, 50-200 PSI, 50-175 PSI, 50-150 PSI, 50-125 PSI, 50-100 PSI, 50-75 PSI, 75-200 PSI, 75-175 PSI, 75-150 PSI, 75-125 PSI, 75-100 PSI, 100-175 PSI, 100-150 PSI, 100-125 PSI, 125-150 PSI, 25 PSI, 30 PSI, 35 PSI, 40 PSI, 45 PSI, 50 PSI, 55 PSI, 60 PSI, 65 PSI, 70 PSI, 75 PSI, 80 PSI, 85 PSI, 90 PSI, 95 PSI, 100 PSI, 105 PSI, 110 PSI, 115 PSI, 120 PSI, 125 PSI, 130 PSI, 135 PSI, 140 PSI, 145 PSI, 150 PSI, 155 PSI, 160 PSI, 165 PSI, 170 PSI, 175 PSI, 180 PSI, 185 PSI, 190 PSI, 195 PSI, 200 PSI, 205 PSI, 210 PSI, 215 PSI, 220 PSI, 225 PSI, 230 PSI, 235 PSI, 240 PSI, 245 PSI, 250 PSI, 300 PSI, 350 PSI, 400 PSI, 450 PSI, 500 PSI, 550 PSI, 600 PS, 650 PSI, 700 PSI, 750 PSI, 800 PSI, 850 PSI, 900 PSI, 950 PSI, or 1000 PSI. In one embodiment, the pressure is from about 25 PSI to about 250 PSI. In another embodiment, the pressure is from about 75 PSI to about 200 PSI. In another embodiment, the pressure is from about 100 PSI to about 400 PSI.

In one embodiment, one or more acids can be combined, resulting in a buffer that can be used for conducting pretreatment of biomass as provided herein in a device as provided herein. In some instances, the pH can be lowered to neutral pH or acidic pH, for example a pH of 7.0, 6.5, 6.0, 5.5, 5.0, 4.5, 4.0, or lower. For example, the non-neutral aqueous medium used to pretreat biomass as provided herein in a device as provided herein can have a pH that is less than 7, 6.5, 6, 5.5, 5, 4.5, 4, 3.5, 3, 2.5, 2, 1.5, or 1. For example, the non-neutral aqueous medium can have a pH that is about 6.5, 6.4, 6.3, 6.2, 6.1, 6, 5.9, 5.8, 5.7, 5.6, 5.5, 5.4, 5.3, 5.2, 5.1, 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, or lower. In some embodiments, the pH is lowered and/or maintained within a range of about pH 4.5 to about 7.1, or about 4.5 to about 6.9, or about pH 5.0 to about 6.3, or about pH 5.5 to about 6.3, or about pH 6.0 to about 6.5, or about pH 5.5 to about 6.9 or about pH 6.2 to about 6.7.

In some embodiments, pretreatment of a biomass as provided herein in a device as provided herein comprises hydration of the biomass composition in a non-neutral aqueous medium having a pH that is greater than 7. For example, the non-neutral aqueous medium can have a pH that is greater than 7, 7.5, 8, 8.5, 9, 9.5, 10, 10.5, 11, 11.5, 12, 12.5, 13, 13.5 or higher. For example, the non-neutral aqueous medium can have a pH that is about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, or higher. The non-neutral aqueous medium having a pH greater than 7 can comprise one or more bases such as sodium hydroxide, calcium hydroxide, potassium hydroxide, ammonia, ammonia hydroxide, hydrogen peroxide or a combination thereof. The one or more bases can be at any suitable concentration, such as any of the concentrations disclosed herein.

In some embodiments, pretreatment of a biomass composition comprises hydration of the biomass composition in a non-neutral aqueous medium comprises from about 0.1% to about 50% w/w or v/v by dry biomass weight of one or more acids or one or more bases. For example, the non-neutral aqueous medium can comprise about 25-50%, 10-50%, 10-25%, 5-50%, 5-25%, 5-10%, 4-50%, 4-25%, 4-10%, 4-5%, 3-50%, 3-25%, 3-10%, 3-5%, 3-4%, 2-50%, 2-25%, 2-10%, 2-5%, 2-4%, 2-3%, 1-50%, 1-25%, 1-10%, 1-5%, 1-4%, 1-3%, 1-2%, 0.5-50%, 0.5-25%, 0.5-10%, 0.5-5%, 0.5-4%, 0.5-3%, 0.5-2%, 0.5-1%, 0.5-%, 0.1-50%, 0.1-25%, 0.1-10%, 0.1-5%, 0.1-4%, 0.1-3%, 0.1-2%, 0.1-1%, 0.1-0.5%, 50%, 45%, 40%, 35%, 30%, 25%, 24%, 23%, 22%, 21%, 20%, 19%, 18%, 17%, 16%, 15%, 14%, 13%, 12%, 11%, 10%, 9.5%, 9%, 8.5%, 8%, 7.5%, 7%, 6.5%, 6%, 5.5%, 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of the one or more acids or the one or more bases. The one or more acids can be sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. The one or more bases can be sodium hydroxide, calcium hydroxide, potassium hydroxide, ammonia, ammonia hydroxide, hydrogen peroxide or a combination thereof. In some embodiments, the non-neutral aqueous medium comprises the one or more acids or the one or more bases at from about 1% to about 5% v/w by dry biomass weight. In some embodiments, the non-neutral aqueous medium comprises sulfuric acid at from about 1% to about 5% v/w by dry biomass weight. In some embodiments, the non-neutral aqueous medium comprises sulfuric acid at about 1.8% v/w by dry biomass weight. In some embodiments, the non-neutral aqueous medium comprises sulfuric acid at about 1% v/w by dry biomass weight.

In the flash tank 70, the biomass can move through a downward directed pipe. The pretreated biomass can be accessible from the flash tank 70. In some cases, a device for pretreating biomass as provided herein can be designed to move the biomass to a separation step or to an enzyme hydrolysis tank. Vapors can be discharged through the open top of the flash tank 70 or, in the alternative, the flash tank 70 can be closed and vapors discharged through a pipe to another area or chamber. Alternatively, the pipe can be connected through a tubing to a condenser.

The apparatus (e.g., barrel cylinder) can be constructed using carbon steel, stainless steel or any other material that is impervious to acid and alkali and that can withstand the pressures generated. It is also possible to have a chemically-inert coating on the inside of the chamber (e.g., barrel cylinder inner chamber) that does not react with acid or alkali or any chemical that is used in the methods provided herein. The cylindrical barrel may be horizontal or vertical with modifications for loading biomass or providing the proper discharge pressure. One skilled in the art could readily configure the apparatus with a vertical barrel for proper operation.

Figure 2:
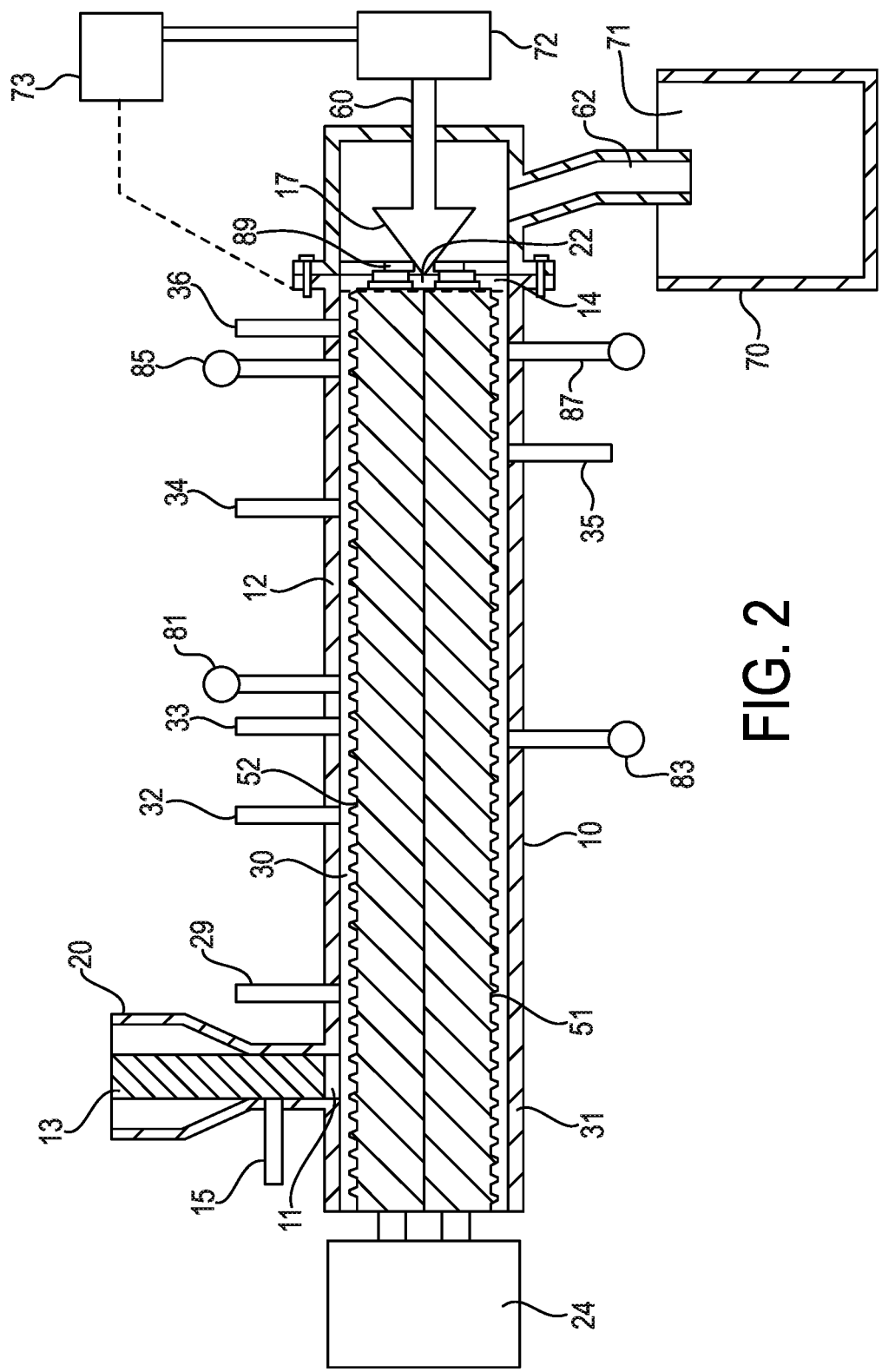
FIG. 2 is a horizontal fragmentary sectional view of an embodiment of an apparatus for use in the invention illustrating the barrel, screws, and end valve attached to a twin screw extruder of the invention.

In some cases, a device for pretreating biomass as provided herein comprises a twin-screw extruder. An example of a co-rotating, twin-screw extruder used for the methods provided herein is shown in FIG. 2. The twin-screw extruder in FIG. 2 comprises barrel 31, a horizontal cylindrical chamber 30, which includes two screw-type feeder mechanisms 51 and 52. The barrel comprises an open first end 11 for adding biomass. The biomass can be any biomass as provided herein. The overall extrusion apparatus 10 includes a primary feed hopper 20 to contain the biomass being added. Inside the hopper 20 is a delivery auger 13 to evenly distribute the material into the open first end 11. There is a port 15 into which water can be added as the biomass enters the extruder chamber 30. The cylindrical chamber 30 has another port 29 for water, sealable ports 32, 33 for the addition of pressurized steam and sealable ports 34, 35 for the addition of chemical reactant (e.g., acid). A third port 36 can be added if additional steam is needed downstream of ports 34 and 35. As in FIG. 1, the barrel chamber 30 is divided into 3 zones (not shown), produced by screw configurations, akin to 91, 92, and 93 in FIG. 1. Pressurized steam is injected to raise the temperature and pressure of the biomass, and chemical for the chemical reaction, if necessary. Insulation 12 can be provided outside or as part of the barrel 31 that can encompass the barrel chamber 30 and maintain the desired temperature inside the chamber. Temperature gauges 83, 87 and pressure gauges 81, 85 are used to monitor temperature and pressure inside the chamber, respectively.

As biomass is loaded through the hopper 20 into the chamber 30, thermo-mechanical pressure builds through the addition of steam and the configuration of plugs (due to the shape and movement of various sections of the screw mechanisms). The twin screw mechanism 51, 52 moves the biomass through the tube to the opening 22 between the end plate 14 of the barrel chamber 30 and the discharge valve 89.

As in FIG. 1, the device of FIG. 2 produces three plugs P1, P2, P3 during the process of moving biomass through the tube from one end to the other (see FIG. 1). While not shown in FIG. 2, P1 is formed after the addition of water through port 29 prior to the addition of steam through the ports 32 and 33. Ports 32, 33 add pressurized steam at about 300 psi to 600 psi to the barrel after the first plug is formed increasing the barrel pressure to a desired temperature and pressure; for example, 600 psi and a temperature of 253° C. P2 is formed prior to the addition of aqueous acid through ports 32 and 33, while P3 is usually formed after the addition of aqueous acid. Also like FIG. 1, in FIG. 2 the zone within the barrel chamber 30 between P1 and P2 is zone 91, while zone 92 is between P2 and P3 and zone 93 is between P3 and the area of discharge. The zone 91 between the first two plugs, zone 92 between plug P2 and plug P3, the zone between plug P3 and the area of discharge through the special end flange 14 collectively constitute the reaction zone R1 (as shown in FIG. 1). In some cases, chemicals used to assist in the pretreatment of the biomass (e.g., acid or alkali or another chemical) are added between the second plug P2 and third plug P3 formed in the reaction zone R1.

In some cases, pretreatment of biomass using a device as depicted in FIG. 2 entails sealing the ports in the device of FIG. 2 following movement of biomass through each section and addition of aqueous solution comprising acid and steam and subsequently maintaining a desired temperature. As shown in FIG. 2, the discharge valve 17 can be partially seated in a metal or ceramic seal 89 such that the discharge valve is mostly closed. In operation, (FIG. 2 and FIG. 12) as pressure in the barrel chamber 30 builds to a certain point, the discharge valve 17 is pushed open (away from the barrel chamber). The valve shaft 60 extends through a tube to an actuator 72 within or attached to a back pressure generator (control unit) 73. The mixture of biomass, sugars, and aqueous chemical is pushed through the discharge valve opening 22 by the movement of the twin screws 50, 51 in the chamber 30 from the first end towards the second (outlet) end and from the pressure buildup. The biomass passes through the discharge valve opening 22 and through a pipe 62 where it is collected in a flash tank 70 through an opening 71 in the top of the flash tank which allows access to pretreated biomass and the exit of vapors. There can also be a separate opening to allow discharge of vapors (not shown).

Figure 3:
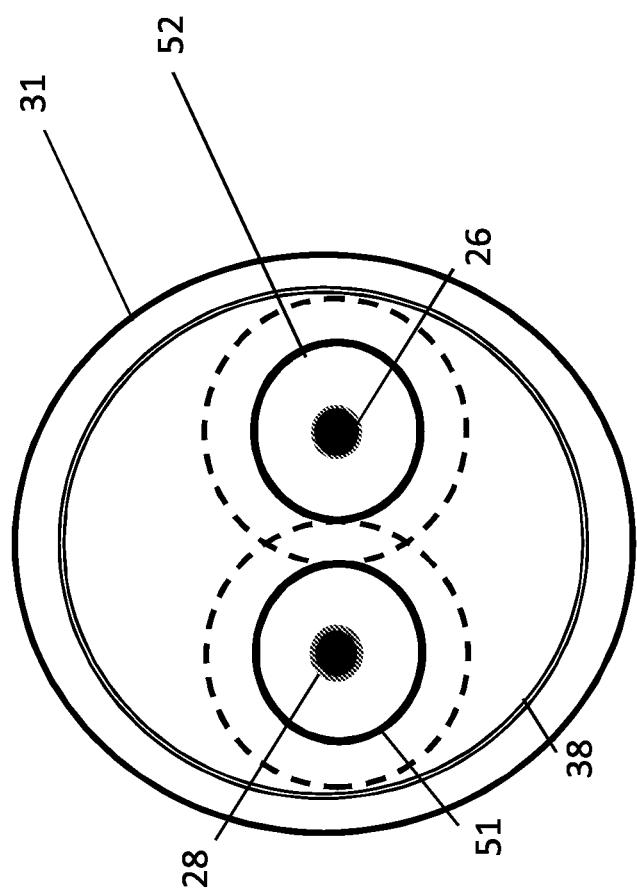
FIG. 3 is a cross-sectional view similar to that of FIG. 2 that depicts the extruder with the twin screws.
Figure 4:
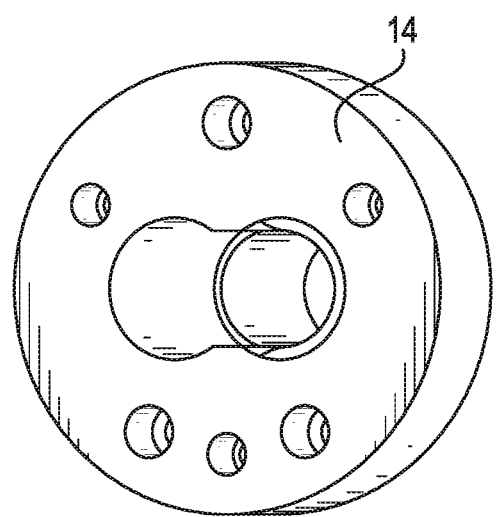
FIG. 4 is a cross-sectional view of the end plate of the extruder that abuts the end of the discharge valve.
Figure 5:
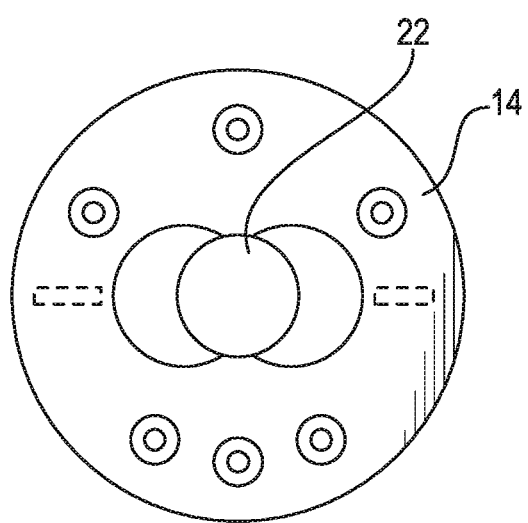
FIG. 5 is a schematic cross-sectional view of the end plate of the extruder and the opening of the valve plate that abuts the end of the extruder.
Figure 6:
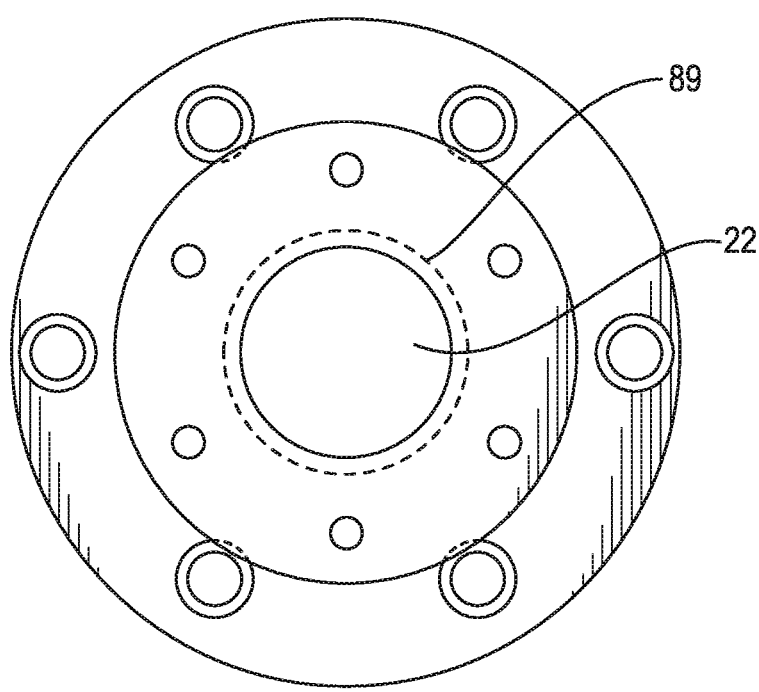
FIG. 6 is a cross-sectional view of the end of the discharge valve plate that abuts the end of the extruder showing the seal facing.

A cross section of the discharge end of the twin screw extruder shown in FIG. 2 is depicted in FIG. 3. As shown in FIG. 3, the barrel 31 houses the twin screws 51, 52 which are turned by the shafts 26, 28. In one embodiment, a replaceable solid barrel insert 38 of corrosion and wear-resistant specialty metal or other compound can surround the screws. The extent of the blade edges of the twin screws 51, 52 and the boundaries of the bored holes through the barrel insert 38 are represented by dotted lines. There is 1 mm or so between the tips of the screw elements and the barrel insert 38. In some instances, the dotted lines can be the actual barrel openings (instead of barrel 31) and can be comprised of specialty metal inserts added for wear resistance and bored out to match the diameter of the screws. In one embodiment, a heating apparatus (not shown) is fitted around a whole cylindrical barrel. FIG. 4 shows a cross section of the discharge end special face flange 14 that is attached to the end of the extruder. The flange 14 is connected to the extruder and the twin screws convey material onward to the discharge valve. FIG. 5 depicts the transition from the two-screw opening in the extruder discharge end flange 14 to the single outlet of the valve opening 22 when looking from the end of the valve opening from the narrow end that connects with valve 17. The opening expands to encompass the two-screw opening of flange 14. FIG. 6 further depicts the discharge valve end housing 19 with a single cylindrical opening 22 that connects adjacent to the extruder flange 14. Pretreated biomass is discharged through the opening 22 surrounded by the metal or ceramic seal 89 which is secured in position to interact with the discharge valve mechanism. The ceramic or metal seal can also extend into the valve opening 22 and provide a coating or insert between the valve opening 22 and the valve housing 19.

Figure 7:
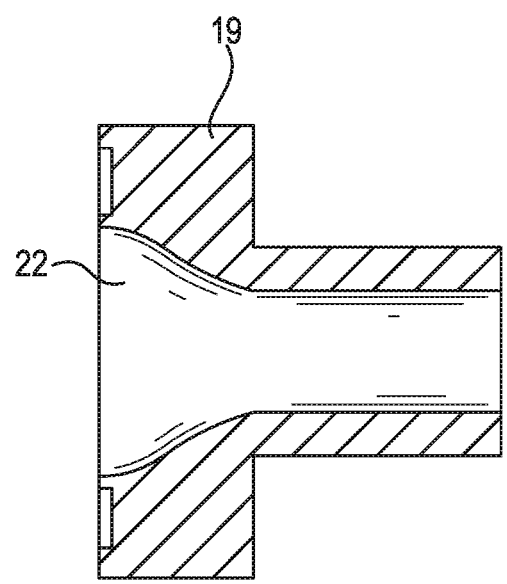
FIG. 7 is a horizontal fragmentary sectional view of the transition from the discharge of the twin screws to the outlet orifice.

The valve at the discharge end ("end valve") of an extruder as provided herein can be one of many different designs. The end valve used in this process can be one of several types that can be precisely monitored and controlled by a back pressure generator. The end valve can be unidirectional or bidirectional. In some cases, an end valve in an extruder as provided herein is unidirectional while the flow through the extruder is unidirectional. In some cases, an end valve in an extruder as provided herein is bidirectional while the flow through the extruder is unidirectional. FIG. 7 is a horizontal view of the valve opening 22 in its housing 19 where it narrows from the two-screw openings of the extruder to the valve discharge end.

Figure 8:
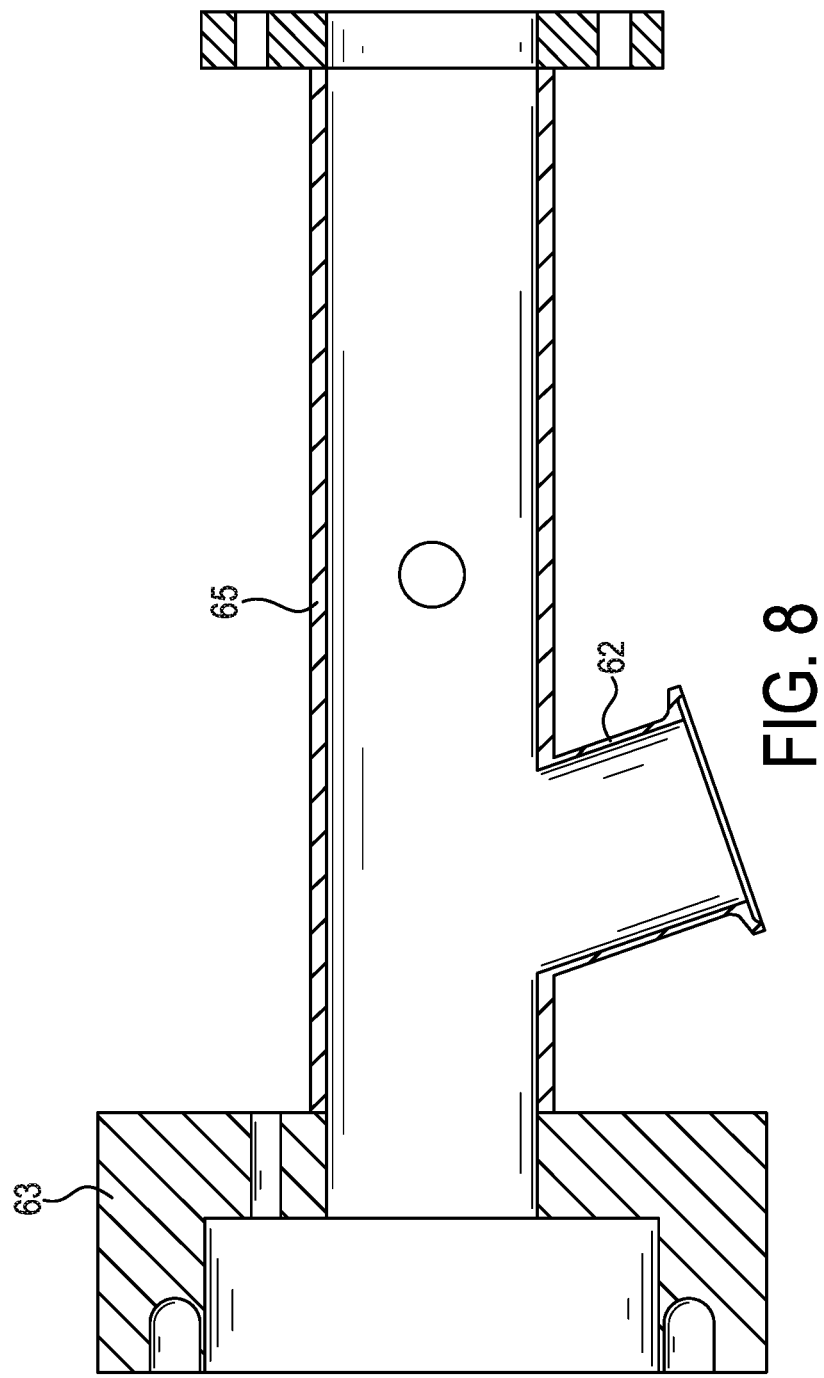
FIG. 8 is a horizontal sectional view of the housing for a valve assembly.
Figure 9:
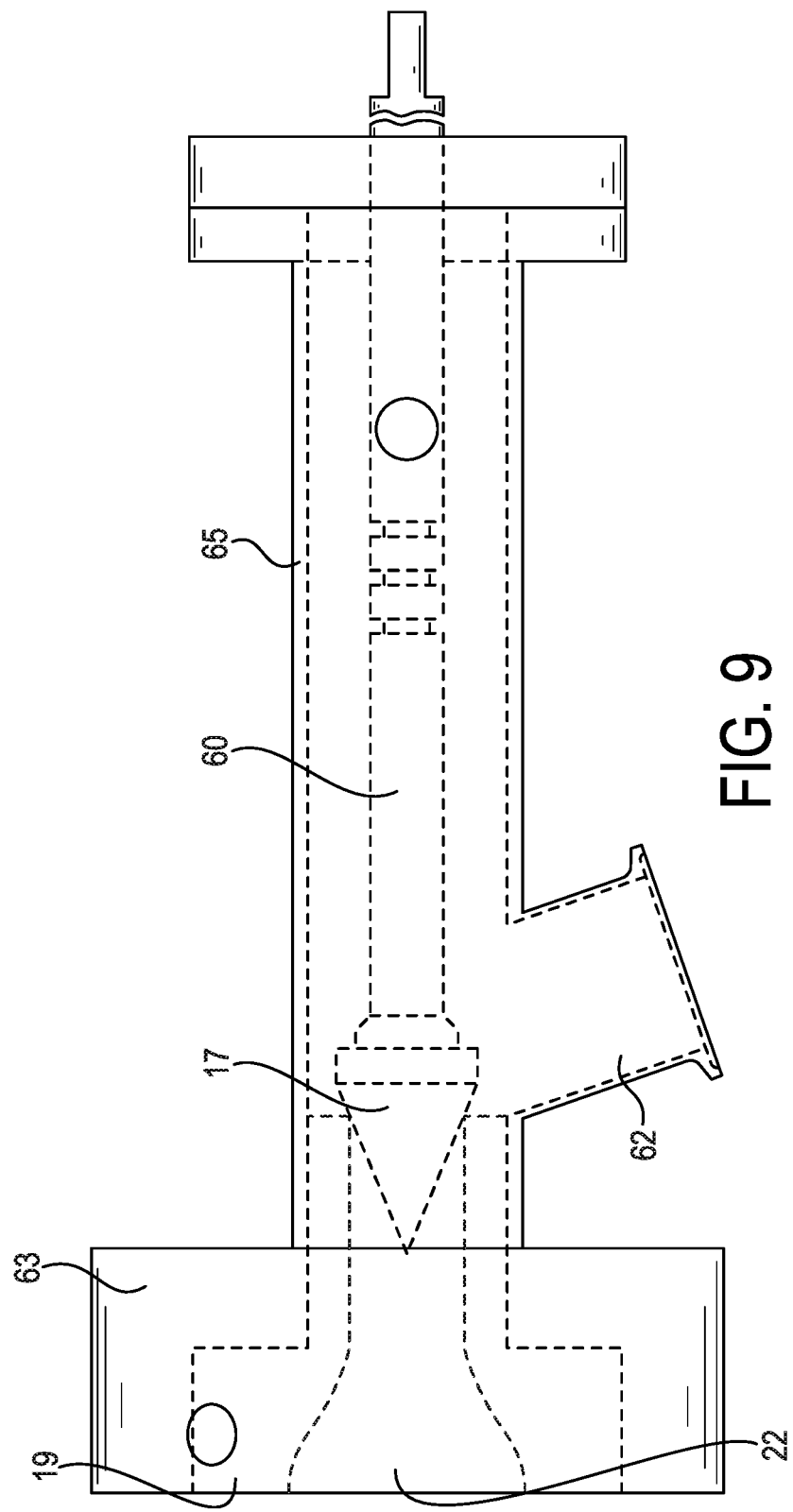
FIG. 9 is a schematic drawing of FIG. 9 showing how the valve assembly fits into the housing.
Figure 10:
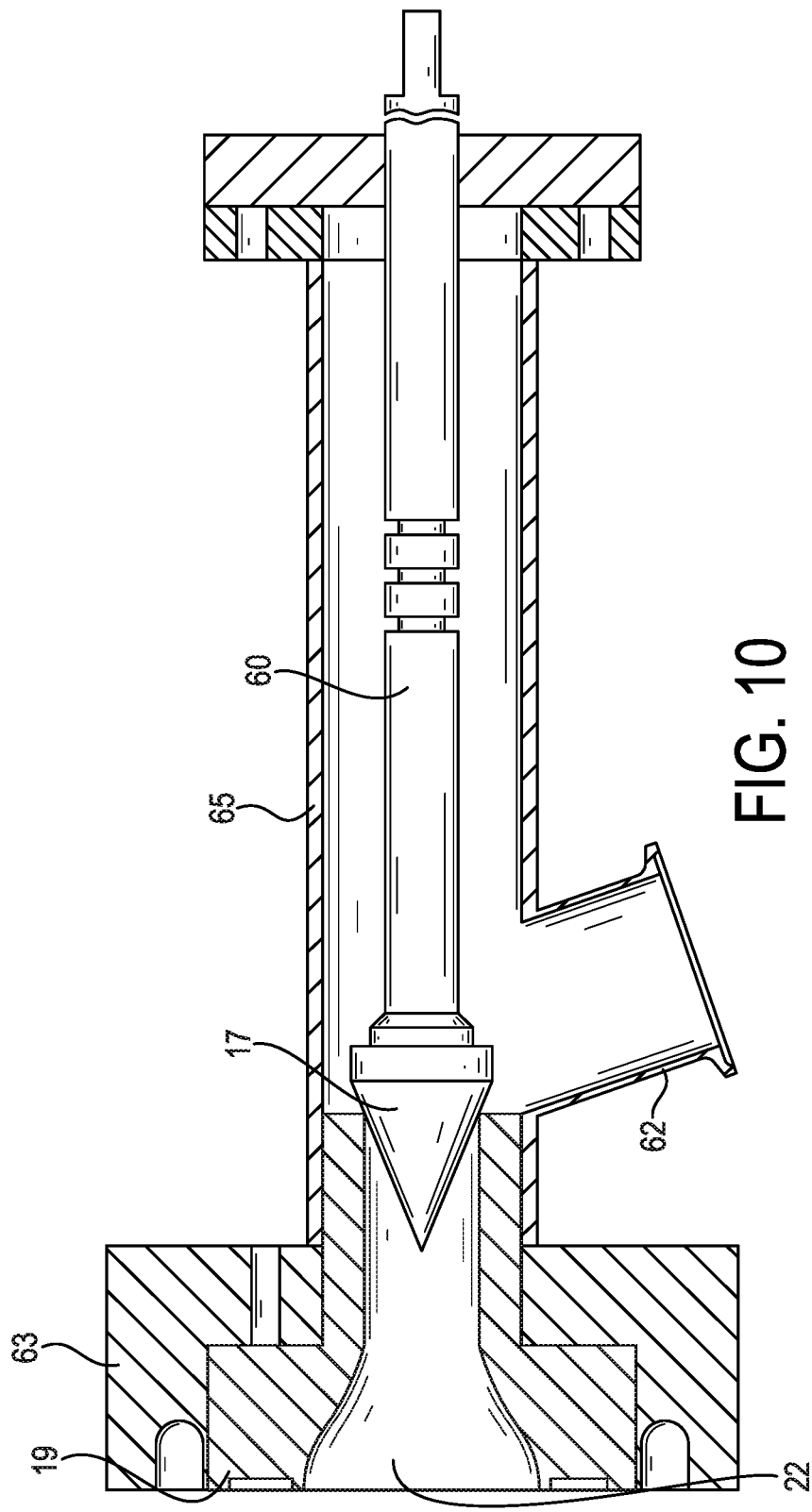
FIG. 10 is a horizontal sectional view of the valve assembly in the housing.

FIG. 8 is a horizontal view of the valve housing assembly 65 with the discharge pipe 62, including the housing 63 that holds the valve opening and housing 19 as shown in FIG. 7. FIG. 9 depicts the housing of FIG. 8, showing how the valve assembly is integrated with the housing. FIG. 10 is a horizontal sectional view with the valve 17 and valve shaft 60 seated in the valve opening housing 19 within the housings 65 and 63.

FIGS. 1 and 2 are embodiments that show the movement of the biomass through reactors using plugs to chamber different reactions and to reduce particle size. These embodiments can be varied to accommodate different types and sizes of biomass for optimal processing and the recovery of monosaccharides or even oligomers. For example, the size of the second chamber can be reduced if the biomass contains a small percentage of hemicellulose compared to the cellulosic portion. Residence time in any chamber can be varied and those of skill in the art will understand that the types of screw elements in sections that produce the plugs, and cut and move the processing materials forward and their placement can have an infinite number of permutations. The combinations used will depend on the type of biomass and the size of the particles desired for optimum pretreatment. Thus residence time, temperature, time, and chemical treatment can be unlimited using this method.

Screw sections incorporated into this system can include, for example, conveying elements for moving materials through the extruder and kneading block elements for forming plugs. One suitable system can be comprised of a single flight screw element with mixing grooves in the screw profile. The element can have a left hand (reversed conveying) or right hand (forward conveying pitched screw profile). These elements can comprise less mixing grooves and reduced groove depth to reduce the product cross flow between the screw profile channels, thus assisting to maintain a uniform pressure and movement of the biomass and reduce backflow. The screw elements can be comprised of various materials, including, for example, Stellite, Hasteloy, Inconell, PM steel, Chromium steel, and nitride steel, and/or can be manufactured with various surface coatings to reduce wear and abrasion. Examples of such elements can be found at Extricom GmbH (www.extricom.de). Those of skill in the art will understand the types of elements and their arrangement are unlimited and can be organized in many different patterns for specific biomass materials.

The initial dry weight of biomass used in the methods of this invention is at least about 10% of the total weight of the biomass and aqueous acid mixture. More typically, the dry weight of biomass is at least about 20%, and can be at least about 30%, 45%, 50%, or more. Feedstock biomass will typically range between 30 wt % and 90 wt % solids, and the biomass exiting the pretreater will typically range between 25 wt % and 40 wt % solids. The percent dry weight of biomass may vary and the optimal percent may be different for different types of biomass. For example, biomass of at least about 40% is desired when using sawdust (sawdust will get diluted with a small amount of steam condensate), to provide pretreated biomass that is saccharified to produce fermentable sugars concentrated sufficiently for cost-effective fermentation to ethanol. More suitable is sawdust biomass that is at least about 30%. The preferred percent dry weight of a particular type of biomass for use in the present methods for producing a high sugars hydrolysate can be readily determined by one skilled in the art.

The biomass can be loaded into a feeder apparatus such as the hopper diagrammed in FIG. 1, which, in turn, feeds it to the reactor. The loading can be facilitated by use of a flow conveyor such as a screw conveyor, crammer, drag chain, bucket elevator, conveyor belt, or the like. The feeding of the biomass into the reactor can be made more uniform by the addition of a conical screw or the like, that allows the biomass to enter the reactor at a uniform rate and density that is helpful to keep the feeder apparatus from clogging.

Using this method, an aqueous solution comprising acid or base can comprise any concentration that is necessary to hydrolyze the carbohydrate polymers. Thus, for example, acid at a concentration of 0.01% to over 7 or 8%, or concentrations of 1%, 2%, 3%, 4%, 5%, 6% or anything in between can be used. In pretreatment devices as provided herein, ports, excluding the one or more through which steam is being added, can be sealed. Valves for use in the devices as provided herein can be any type of valve known in the art that can be opened or closed. The valves can be ball valves, poppet valves, check valves, or rotating knife-gate valves, or combinations thereof.

Steam can be added through one or more ports in the cylindrical barrel at the beginning of the reaction zone, after the first plug is formed, in an amount that is needed to raise the temperature of the biomass and aqueous acid mixture to the desired point. More than one port can be used, with ports being spaced so that steam contact is distributed over the biomass or to raise the temperature and pressure more quickly. Pressurized steam can be added to raise the temperature of the biomass and aqueous acid mixture to between about 80° C. and about 300° C., preferably between 160° C. and 230° C. The temperature of the biomass and aqueous acid can be about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., or 400° C. The temperature of the biomass and aqueous acid can be from about 20° C. to about 400° C., about 50° C. to about 350° C., about 80° C. to about 300° C., about 100° C. to about 250° C., or about 160° C. to about 210° C. Additional steam can be added through a port between the second and third plug formation of cylindrical chamber, if needed, to maintain the desired temperature and pressure. The apparatus can include a heating jacket, steam jacket, band heaters, barrel heaters, or insulation jacket to contribute to raising and/or maintaining the temperature and pressure. Heating or steam jackets are particularly suited to small scale reactors while insulation jackets are suited to large scale reactors. Heating can occur at different stages, including preheating the barrel prior to treating or pretreating. The type of biomass being pretreated also can affect the optimum time and temperature for treatment in the present method, as can readily be assessed by one skilled in the art.

Bringing the biomass to the described temperatures using pressurized steam in these methods results in pressures within the reactor chamber that are between about 300 psi and about 1000 psi. More typically, pressure is between about 300 psi to 800 psi. The pressurized steam is added through the ports at about 300 to 600 psi. The pressures within the reactor chamber can be 25-250 PSI, 25-225 PSI, 25-200 PSI, 25-175 PSI, 25-150 PSI, 25-125 PSI, 25-100 PSI, 25-75 PSI, 25-50 PSI, 50-225 PSI, 50-200 PSI, 50-175 PSI, 50-150 PSI, 50-125 PSI, 50-100 PSI, 50-75 PSI, 75-200 PSI, 75-175 PSI, 75-150 PSI, 75-125 PSI, 75-100 PSI, 100-175 PSI, 100-150 PSI, 100-125 PSI, 125-150 PSI, 25 PSI, 30 PSI, 35 PSI, 40 PSI, 45 PSI, 50 PSI, 55 PSI, 60 PSI, 65 PSI, 70 PSI, 75 PSI, 80 PSI, 85 PSI, 90 PSI, 95 PSI, 100 PSI, 105 PSI, 110 PSI, 115 PSI, 120 PSI, 125 PSI, 130 PSI, 135 PSI, 140 PSI, 145 PSI, 150 PSI, 155 PSI, 160 PSI, 165 PSI, 170 PSI, 175 PSI, 180 PSI, 185 PSI, 190 PSI, 195 PSI, 200 PSI, 205 PSI, 210 PSI, 215 PSI, 220 PSI, 225 PSI, 230 PSI, 235 PSI, 240 PSI, 245 PSI, 250 PSI, 300 PSI, 350 PSI, 400 PSI, 450 PSI, 500 PSI, 550 PSI, 600 PS, 650 PSI, 700 PSI, 750 PSI, 800 PSI, 850 PSI, 900 PSI, 950 PSI, or 1000 PSI. However, under certain circumstances a lower pressure could be desirable. For example, it takes little or no pressure to release C5 polymers from a C5-rich and/or lignin-free biomass.

In the embodiments of this invention (e.g., FIGS. 1 and 2), following pre-treatment of a biomass as provided herein for the desired time at the proper pressure and temperature, the biomass and aqueous chemical or other mixture is moved through a discharge valve 17 at the end of the cylindrical barrel 30 into a flash tank 70. The discharge valve 17 can be closed during biomass reaction with aqueous acid or other chemical at the desired temperature, then opened for passage of the biomass. In a twin screw chamber reactor, as exemplified in FIG. 2, the discharge valve 17 opens under pressure of the extruder with the opening of the valve between the end of the extruder and the valve chamber, after the steam and biomass has built up pressure in the reaction chamber, and discharges pretreated biomass to relieve the pressure to the point that the pressure delivered to the end valve through the shaft is greater. The use of the external valve is a great advantage over attempting to maintain homogeneous pressure in the barrel when using plug formation to maintain various zones. The zones can be maintained more easily when a release of pressurized material is controlled by a separately-responsive pressurized valve.

Figure 11:
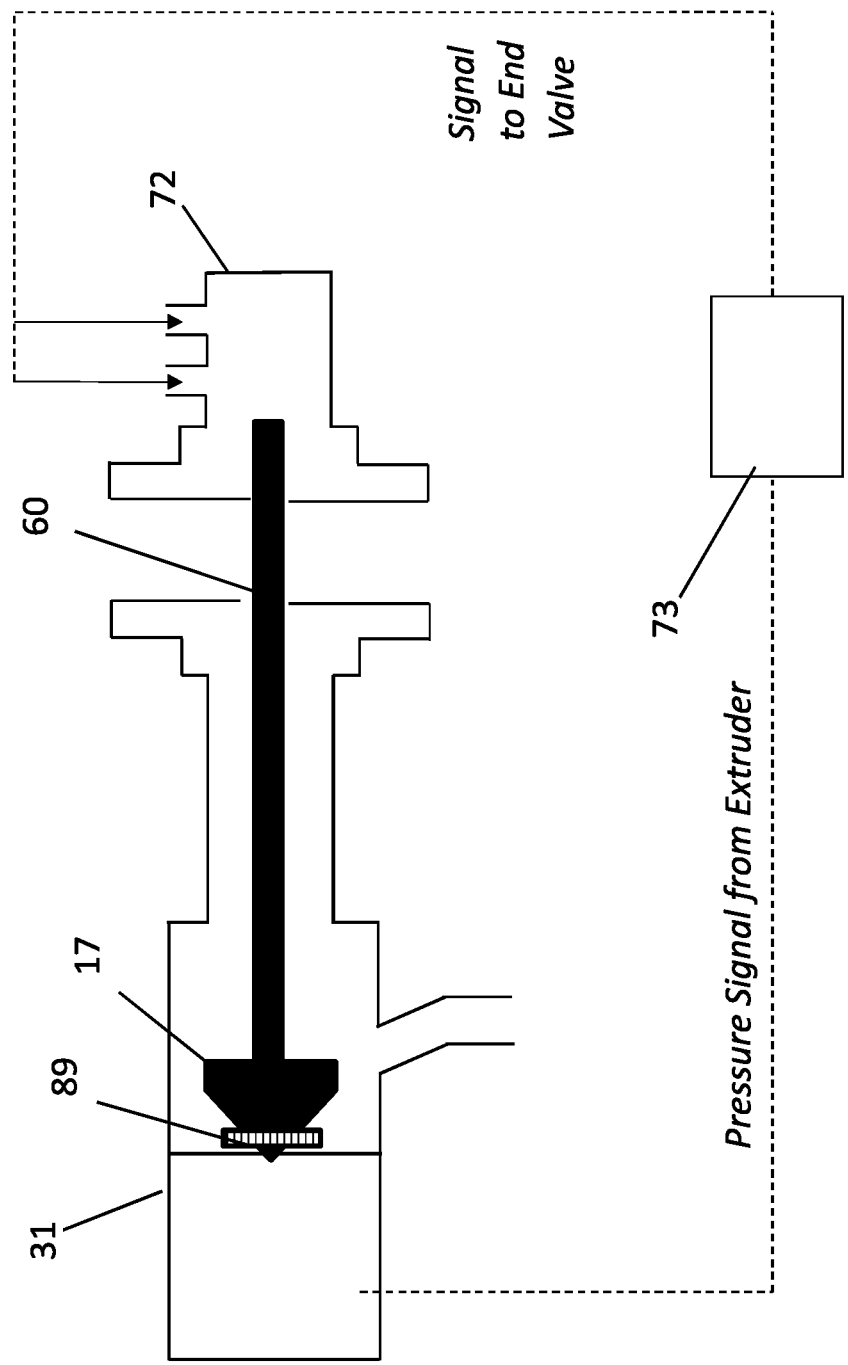
FIG. 11 is a schematic drawing of one embodiment of a gradual expansion venturi used as a discharge valve with the valve mostly closed.
Figure 12:
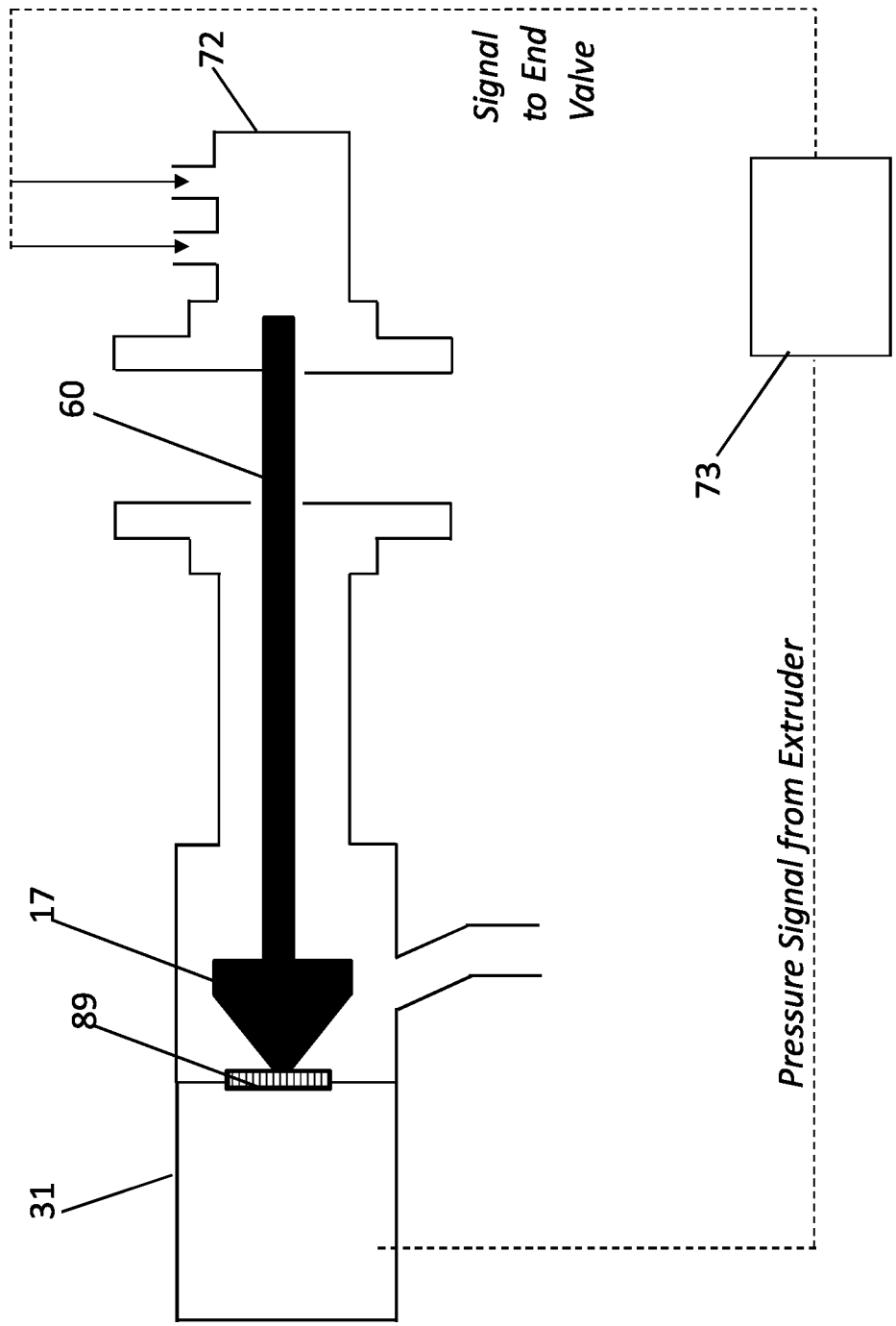
FIG. 12 is a schematic drawing of the gradual expansion venturi embodiment of FIG. 11, with the valve mostly open.

For example FIG. 12, illustrates an open valve 17 in a device as depicted in FIG. 2, which occurs when the pressure of the steam and biomass in the barrel chamber 30 (in FIG. 2) in the cylindrical barrel 31 is greater than the pressure delivered to the end valve 17. As the pressure in the chamber is reduced, the shaft pressure on the end valve 17 pushes the valve towards closure against the end of the extruder, thus reducing the release of biomass into the flash tank 70 in FIG. 2 and allowing pressure to build in the extruder again. In contrast, FIG. 11 illustrates the position of the valve 17 when it is seated in the metal or ceramic seal 89 and the shaft pressure is greater than the pressure in the extruder. In combination, FIGS. 11 and 12 depict a constant movement of the end valve forward and back as biomass is treated in the cylindrical barrel 31. In some cases, the end valve 17 is never completely closed and never completely open. Thus, the end valve remains substantially open throughout operation while a consistent pressure is maintained in the extruder while biomass is treated and released.

The application described herein can be continuous, and the key to the outlet valve is the constant monitoring of the system pressure. There is a feedback loop that continuously adjusts the valve opening in order to maintain a specific system pressure. See FIGS. 11 and 12. This can allows for a continuous flash process and the extruder can be continuously adjusted to maintain a desired pressure in the continuous process. Overall, this can be a more complex mechanism than normal pretreatment discharge systems, and can offers very tight, precise control of a continuous process.

Examples of discharge valves that can be used include poppet discharge valves, knife gate valves, seat valves, butterfly valves, rotary V-port valves, and the like. Particularly useful in a smaller scale reactor, can be a piston-operated linear globe or a poppet-type discharge valve, where a hard-faced upstream side of the valve seat is a ceramic discharge orifice, and a softer downstream side of the valve seat seals against a hard-faced valve plunger, with the flow area increasing continually beyond the valve seat when the valve plunger is retracted to open.

Most suitably, the poppet-type discharge valve would incorporate a gradual expansion venturi. One embodiment of a gradual expansion venturi poppet valve that is suitable for a biomass pretreatment reactor is diagrammed in FIG. 10. This valve incorporates a conical nozzle and a metal or ceramic seat end valve arrangement. To avoid plugging, the gradual expansion venturi as exemplified in FIG. 11 (closed position) and FIG. 12 (open position) can be designed to accelerate solids through a steadily enlarging gap between the stationary cylinder 89 of the venturi and the moveable inside cone 17 of the venturi that is mounted on the end of a valve shaft 60. The discharge cylinder that the cone fits into can be generally seated into the discharge valve housing 19 at the reactor chamber exit. The venturi inside cone 89 can be the nose on the end of the valve shaft 60. The valve shaft 60 can be attached to an actuator 72 for control of movement. The actuator 72 may be any device known in the art that can be able to move the valve shaft back and forth in a horizontal motion, such as an electric, pneumatic or hydraulic motor, pneumatic valve actuator, or hydraulic piston or any other type actuator known in the art and/or provided herein. The actuator, in turn, can be within or attached to an electronic pressure regulator 73 that receives a pressure signal from the reaction chamber. For example, an E/P pressure regulator, series ED05 (Bosch Rexroth AG) can be used. When the valve shaft is in its farthest leftward position, the outer edge of the inside cone seats against the inner edge of the metal or ceramic outside cylinder to seal the discharge end of the reactor. During pretreatment, the valve shaft can be moved to the right to provide the size of opening that is desired for the flash venturi. This design can provide a flash zone of some length which expands smoothly in the direction of flow. In this design, biomass solids can be accelerated down the axis of the gradually-opening annular cone until the pressure in the chamber can be released to the point where an electronic signal from the reaction chamber results in pressure delivered to the end valve that causes the end valve to move towards the chamber, closing the gap between the flash venturi and the metal or ceramic seat.

The treated biomass can be flashed through the discharge valve moving into a pipe that leads into the flash tank. Vapors can then be released and the biomass can be cooled in preparation for pH adjustment, solids separation and/or enzymatic hydrolysis. Any typical flash tank may be used. The flash tank can be The flashing can result in a drop in pressure from the pressure maintained inside the reaction zone (e.g., the reaction zone depicted in FIGS. 1 and 2) to a pressure near atmospheric and can typically cool the biomass material to about 100° C. The temperature can then be reduced to about 50° C. which can be desired for enzymatic saccharification. The biomass can be removed from the flash tank and saccharified in batches. Generally, at this point, the C5 polymers have been hydrolyzed into oligomers or monosaccharides, depending on the amount of acid or alkali used and the temperature and pressure maintained during the treatment in the reaction zones of the barrel chamber (see FIGS. 1 and 2), as well as hydrolysis of a certain fraction or percentage of amorphous regions and C6 polymers, leaving fragmented C6 crystalline lattices opened for saccharification (e.g., enzymatic saccharification).

In some cases, the pH of a feedstock pretreated by the methods provided herein in a device as provided herein is adjusted prior to further treatment (e.g., enzymatic saccharification). Alteration of the pH of a pretreated feedstock can be accomplished by washing the feedstock (e.g., with water) one or more times to remove an alkaline or acidic substance, or other substance used or produced during pretreatment. Washing can comprise exposing the pretreated feedstock to an equal volume of water 2, 3, 4, 5, 6, 7, 8, 9, 10, 11, 12, 13, 14, 15, 16, 17, 18, 19, 20, 21, 22, 23, 24, 25 or more times. In another embodiment, a pH modifier can be added. For example, an acid, a buffer, or a material that reacts with other materials present can be added to modulate the pH of the feedstock. In one embodiment, more than one pH modifier can be used, such as one or more bases, one or more bases with one or more buffers, one or more acids, one or more acids with one or more buffers, or one or more buffers. When more than one pH modifiers are utilized, they can be added at the same time or at different times. Other non-limiting exemplary methods for neutralizing feedstocks treated with alkaline substances have been described, for example in U.S. Pat. Nos. 4,048,341; 4,182,780; and 5,693,296.

In some cases, a system can be designed to hydrolyze and remove the C5 polymers in a first reaction chamber or zone prior to subjecting them to a strong acid treatment and/or high temperatures or pressures in a second reaction chamber zone. Dilute acid and hot water treatment methods can be used to solubilize all or a portion of the hemicellulose. Methods employing alkaline reagents can be used to remove all, most, or a portion of the lignin during the pretreatment step. The remaining C6 polymers and lignin residues can be treated at high acid concentrations and high temperatures and pressures without the formation of C5 byproducts, such as furfurals and acetic acid. This would result in a mixture of C6 polymers essentially without C5 sugars and inhibitors from hydrolysis of C5 polymers. A pure C6 stream of this type is desirable to produce particular end-products such as bioplastics and to supplement starch fermentation to ethanol and other biofuels.

In some cases, a biomass or feedstock as provided herein is subject to pretreatment using a device as provided herein such that the sugars (saccharides) produced from the pretreatment are separated and recovered for an end product as provided herein. The sugars separated and recovered can be used without a hydrolysis step. The sugars separated and recovered can be monosaccharides or saccharide oligomers or a combination thereof. The sugars (e.g., monosaccharides and/or oligomers) can be C5 and/or C6 saccharides or a combination thereof. In some cases, the biomass subjected to pretreatment for the production of saccharide oligomers in corn fiber. The saccharide oligomers produced from the corn fiber can be C5 oligomers. In one embodiment, pretreatment of biomass or feedstock as provided herein produces a pretreated feedstock concentration of soluble oligomers in the pretreated feedstock that is 1%, 10%, 15%, 20%, 25%, 30%, 35%, 40%, 45%, 50%, 55%, 60%, 65%, 70%, 75%, 80%, 85%, 90%, 95%, or 99%. Examples of soluble oligomers include, but are not limited to, cellobiose and xylobiose. In one embodiment, the parameters of the pretreatment produce a concentration of soluble oligomers in the pretreated feedstock that is 30% to 90%. In one embodiment, the parameters of the pretreatment are such that the concentration of soluble oligomers in the pretreated feedstock is 45% to 80%.

Enzymatic Hydrolysis

In one embodiment, the enzyme treatment is used to hydrolyze various higher saccharides (higher molecular weight) present in biomass to lower saccharides (lower molecular weight), such as in preparation for fermentation by biocatalysts such as yeasts to produce ethanol, hydrogen, or other chemicals such as organic acids including succinic acid, formic acid, acetic acid, and lactic acid. These enzymes and/or the hydrolysate can be used in fermentations to produce various products including fuels, and other chemicals.

In one example, the process for converting biomass material into ethanol includes pretreating the biomass material (e.g., "feedstock"), hydrolyzing the pretreated biomass to convert polysaccharides to oligosaccharides, further hydrolyzing the oligosaccharides to monosaccharides, and converting the monosaccharides to biofuels and chemical products. Enzymes such as cellulases, polysaccharases, lipases, proteases, ligninases, and hemicellulases, help produce the monosaccharides can be used in the biosynthesis of fermentation end-products. Biomass material that can be utilized includes woody plant matter, non-woody plant matter, cellulosic material, lignocellulosic material, hemicellulosic material, carbohydrates, pectin, starch, inulin, fructans, glucans, corn, algae, sugarcane, other grasses, switchgrass, bagasse, wheat straw, barley straw, rice straw, corncobs, bamboo, citrus peels, sorghum, high biomass sorghum, seed hulls, and material derived from these. The final product can then be separated and/or purified, as indicated by the properties for the desired final product. In some instances, compounds related to sugars such as sugar alcohols or sugar acids can be utilized as well.

Chemicals used in the methods of the present invention are readily available and can be purchased from a commercial supplier, such as Sigma-Aldrich. Additionally, commercial enzyme cocktails (e.g. Accellerase™ 1000, CelluSeb-TL, CelluSeb-TS, Cellic™ CTec, STARGEN™, Maxalig™, Spezyme.R™, Distillase.R™, G-Zyme.R™, Fermenzyme.R™, Fermgen™, GC 212, or Optimash™) or any other commercial enzyme cocktail can be purchased from vendors such as Specialty Enzymes & Biochemicals Co., Genencor, or Novozymes. Alternatively, enzyme cocktails can be prepared by growing one or more organisms such as for example a fungi (e.g. a *Trichoderma*, a *Saccharomyces*, a *Pichia*, a White Rot Fungus etc.), a bacteria (e.g. a *Clostridium*, or a coliform bacterium, a *Zymomonas* bacterium, *Sacharophagus degradans* etc.) in a suitable medium and harvesting enzymes produced therefrom. In some embodiments, the harvesting can include one or more steps of purification of enzymes.

In one embodiment, treatment of biomass following pretreatment of the biomass using methods and devices provided herein comprises enzyme hydrolysis. In one embodiment a biomass following pretreatment as provided herein is treated with an enzyme or a mixture of enzymes, e.g., endonucleases, exonucleases, cellobiohydrolases, cellulase, beta-glucosidases, glycoside hydrolases, glycosyltransferases, lyases, esterases and proteins containing carbohydrate-binding modules. In one embodiment, the enzyme or mixture of enzymes is one or more individual enzymes with distinct activities. In another embodiment, the enzyme or mixture of enzymes can be enzyme domains with a particular catalytic activity. For example, an enzyme with multiple activities can have multiple enzyme domains, including for example glycoside hydrolases, glycosyltransferases, lyases and/or esterases catalytic domains.

In one embodiment, enzymes that degrade polysaccharides are used for the hydrolysis of biomass and can include enzymes that degrade cellulose, namely, cellulases. Examples of some cellulases include endocellulases and exo-cellulases that hydrolyze beta-1,4-glucosidic bonds.

In one embodiment, enzymes that degrade polysaccharides are used for the hydrolysis of biomass and can include enzymes that have the ability to degrade hemicellulose, namely, hemicellulases. Hemicellulose can be a major component of plant biomass and can contain a mixture of pentoses and hexoses, for example, D-xylopyranose, L-arabinofuranose, D-mannopyranose, Dglucopyranose, D-galactopyranose, D-glucopyranosyluronic acid and other sugars. In one embodiment, enzymes that degrade polysaccharides are used for the hydrolysis of biomass and can include enzymes that have the ability to degrade pectin, namely, pectinases. In plant cell walls, the cross-linked cellulose network can be embedded in a matrix of pectins that can be covalently cross-linked to xyloglucans and certain structural proteins. Pectin can comprise homogalacturonan (HG) or rhamnogalacturonan (RH).

In one embodiment, hydrolysis of biomass includes enzymes that can hydrolyze starch. Enzymes that hydrolyze starch include alpha-amylase, glucoamylase, beta-amylase, exo-alpha-1,4-glucanase, and pullulanase.

In one embodiment, hydrolysis of biomass comprises hydrolases that can include enzymes that hydrolyze chitin, namely, chitinase. In another embodiment, hydrolases can include enzymes that hydrolyze lichen, namely, lichenase.

In one embodiment, more than one of these steps can occur at any given time. For example, hydrolysis of the pretreated feedstock and hydrolysis of the oligosaccharides can occur simultaneously, and one or more of these can occur simultaneously to the conversion of monosaccharides to a fuel or chemical.

In another embodiment, an enzyme can directly convert the polysaccharide to monosaccharides. In some instances, an enzyme can hydrolyze the polysaccharide to oligosaccharides and the enzyme or another enzyme can hydrolyze the oligosaccharides to monosaccharides.

In another embodiment, the enzymes can be added to the fermentation or they can be produced by microorganisms present in the fermentation. In one embodiment, the microorganism present in the fermentation produces some enzymes. In another embodiment, enzymes are produced separately and added to the fermentation.

For the overall conversion of pretreated biomass to final product to occur at high rates, it is generally necessary for each of the necessary enzymes for each conversion step to be present with sufficiently high activity. If one of these enzymes is missing or is present in insufficient quantities, the production rate of an end product can be reduced. The production rate can also be reduced if the microorganisms responsible for the conversion of monosaccharides to product only slowly take up monosaccharides and/or have only limited capability for translocation of the monosaccharides and intermediates produced during the conversion to end product. Additions of fractions obtained from pretreatment and/or pretreatment and hydrolysis can increase initial or overall growth rates. In another embodiment, oligomers are taken up slowly by a biocatalyst, necessitating an almost complete conversion of polysaccharides and oligomers to monomeric sugars.

In another embodiment, the enzymes of the method are produced by a biocatalyst, including a range of hydrolytic enzymes suitable for the biomass materials used in the fermentation methods. In one embodiment, a biocatalyst is grown under conditions appropriate to induce and/or promote production of the enzymes needed for the saccharification of the polysaccharide present. The production of these enzymes can occur in a separate vessel, such as a seed fermentation vessel or other fermentation vessel, or in the production fermentation vessel where ethanol production occurs. When the enzymes are produced in a separate vessel, they can, for example, be transferred to the production fermentation vessel along with the cells, or as a relatively cell free solution liquid containing the intercellular medium with the enzymes. When the enzymes are produced in a separate vessel, they can also be dried and/or purified prior to adding them to the hydrolysis or the production fermentation vessel. The conditions appropriate for production of the enzymes are frequently managed by growing the cells in a medium that includes the biomass that the cells will be expected to hydrolyze in subsequent fermentation steps. Additional medium components, such as salt supplements, growth factors, and cofactors including, but not limited to phytate, amino acids, and peptides can also assist in the production of the enzymes utilized by the microorganism in the production of the desired products.

Fermentation

The present disclosure also provides a fermentative mixture comprising: a cellulosic feedstock pre-treated with an alkaline or acid substance and at a temperature of from about 160° C. to about 210° C.; subsequently hydrolyzed with an enzyme mixture, and a microorganism capable of fermenting a five-carbon sugar and/or a six-carbon sugar. In one embodiment, the five-carbon sugar is xylose, arabinose, or a combination thereof. In one embodiment, the six-carbon sugar is glucose, galactose, mannose, or a combination thereof. In one embodiment, the alkaline substance is NaOH. In some embodiments, NaOH is added at a concentration of about 0.5% to about 2% by weight of the feedstock. In one embodiment, the acid is equal to or less than 2% HCl or $H_2SO_4$. In one embodiment, the microorganism is a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises fermentation of the biomass using a microorganism that is *Clostridium phytofermentans, Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Rhodococcus opacus, Rumino-* coccus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans, or Thermoanaerobacterium saccharolyticum. In still another embodiment, the microorganism is genetically modified to enhance activity of one or more hydrolytic enzymes, such as a genetically-modified *Saccharomyces cerevisiae*.

In one embodiment a wild type or a genetically-improved microorganism can be used for chemical production by fermentation. Methods to produce a genetically-improved strain can include genetic modification, protoplast fusion, mutagenesis, and adaptive processes, such as directed evolution. For example, yeasts can be genetically-modified to ferment C5 sugars. Other useful yeasts are species of *Candida, Cryptococcus, Debaryomyces, Deddera, Hanseniaspora, Kluyveromyces, Pichia, Schizosaccharomyces*, and *Zygosaccharomyces*. *Rhodococcus* strains, such as *Rhodococcus opacus* variants are a source of triacylglycerols and other storage lipids. (See, e.g., Waltermann, et al., Microbiology 146:1143-1149 (2000)). Other useful organisms for fermentation include, but are not limited to, yeasts, especially *Saccaromyces* strains and bacteria such as *Clostridium phytofermentans, Thermoanaerobacter ethanolicus, Clostridium thermocellum, Clostridium beijerinickii, Clostridium acetobutylicum, Clostridium tyrobutyricum, Clostridium thermobutyricum, Thermoanaerobacterium saccharolyticum, Thermoanaerobacter thermohydrosulfuricus, Clostridium acetobutylicum, Moorella* ssp., *Carboxydocella* ssp., *Zymomonas mobilis*, recombinant *E. Coli, Klebsiella oxytoca, Rhodococcus opacus* and *Clostridium beijerinckii*.

An advantage of yeasts are their ability to grow under conditions that include elevated ethanol concentration, high sugar concentration, low sugar concentration, and/or operate under anaerobic conditions. These characteristics, in various combinations, can be used to achieve operation with long or short fermentation cycles and can be used in combination with batch fermentations, fed batch fermentations, self-seeding/partial harvest fermentations, and recycle of cells from the final fermentation as inoculum.

In one embodiment, fed-batch fermentation is performed on the pre-treated and subsequently treated biomass to produce a fermentation end-product, such as alcohol, ethanol, organic acid, succinic acid, TAG, or hydrogen. In one embodiment, the fermentation process comprises simultaneous hydrolysis and fermentation (SSF) of the biomass using one or more microorganisms such as a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises simultaneous hydrolysis and fermentation of the biomass using a microorganism that is *Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Clostridium phytofermentans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans,* or *Thermoanaerobacterium saccharolyticum*.

In one embodiment, the fermentation process can include separate hydrolysis and fermentation (SHF) of a biomass with one or more enzymes, such as a xylanases, endo-1,4-beta-xylanases, xylosidases, beta-D-xylosidases, cellulases, hemicellulases, carbohydrases, glucanases, endoglucanases, endo-1,4-beta-glucanases, exoglucanases, glucosidases, beta-D-glucosidases, amylases, cellobiohydrolases, exocellobiohydrolases, phytases, proteases, peroxidase, pectate lyases, galacturonases, or laccases. In one embodiment one or more enzymes used to treat a biomass is thermostable. In another embodiment a biomass is treated with one or more enzymes, such as those provided herein, prior to fermentation. In another embodiment a biomass is treated with one or more enzymes, such as those provided herein, during fermentation. In another embodiment a biomass is treated with one or more enzymes, such as those provided herein, prior to fermentation and during fermentation. In another embodiment an enzyme used for hydrolysis of a biomass is the same as those added during fermentation. In another embodiment an enzyme used for hydrolysis of biomass is different from those added during fermentation.

In some embodiments, fermentation can be performed in an apparatus such as bioreactor, a fermentation vessel, a stirred tank reactor, or a fluidized bed reactor. In one embodiment the treated biomass can be supplemented with suitable chemicals to facilitate robust growth of the one or more fermenting organisms. In one embodiment a useful supplement includes but is not limited to, a source of nitrogen and/or amino acids such as yeast extract, cysteine, or ammonium salts (e.g. nitrate, sulfate, phosphate etc.); a source of simple carbohydrates such as corn steep liquor, and malt syrup; a source of vitamins such as yeast extract; buffering agents such as salts (including but not limited to citrate salts, phosphate salts, or carbonate salts); or mineral nutrients such as salts of magnesium, calcium, or iron. In some embodiments redox modifiers are added to the fermentation mixture including but not limited to cysteine or mercaptoethanol.

In one embodiment the titer and/or productivity of fermentation end-product production by a microorganism is improved by culturing the microorganism in a medium comprising one or more compounds comprising hexose and/or pentose sugars. In one embodiment, a process comprises conversion of a starting material (such as a biomass) to a biofuel, such as one or more alcohols. In one embodiment, methods of the invention comprise contacting substrate comprising both hexose (e.g. glucose, cellobiose) and pentose (e.g. xylose, arabinose) saccharides with a microorganism that can hydrolyze C5 and C6 saccharides to produce ethanol. In another embodiment, methods of the invention comprise contacting substrate comprising both hexose (e.g. glucose, cellobiose) and pentose (e.g. xylose, arabinose) saccharides with *R. opacus* to produce TAG.

In some embodiments of the present invention, batch fermentation with a microorganism of a mixture of hexose and pentose saccharides using the methods of the present invention provides uptake rates of about 0.1-8 g/L/h or more of hexose and about 0.1-8 g/L/h or more of pentose (xylose, arabinose, etc.). In some embodiments of the present invention, batch fermentation with a microorganism of a mixture of hexose and pentose saccharides using the methods of the present invention provides uptake rates of about 0.1, 0.2, 0.4, 0.5, 0.6 0.7, 0.8, 1, 2, 3, 4, 5, or 6 g/L/h or more of hexose and about 0.1, 0.2, 0.4, 0.5, 0.6 0.7, 0.8, 1, 2, 3, 4, 5, or 6 g/L/h or more of pentose.

In one embodiment, a method for production of ethanol or another alcohol produces about 10 g/l to 120 gain 40 hours or less. In another embodiment a method for production of ethanol produces about 10 g/1, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 110 g/l, 120 g/l, or more alcohol in 40 hours by the fermentation of biomass. In another embodiment, alcohol is produced by a method comprising simultaneous fermentation of hexose and pentose saccharides. In another embodiment, alcohol is produced by a microorganism comprising simultaneous fermentation of hexose and pentose saccharides.

In another embodiment, the level of a medium component is maintained at a desired level by adding additional medium component as the component is consumed or taken up by the organism. Examples of medium components included, but are not limited to, carbon substrate, nitrogen substrate, vitamins, minerals, growth factors, cofactors, and biocatalysts. The medium component can be added continuously or at regular or irregular intervals. In one embodiment, additional medium component is added prior to the complete depletion of the medium component in the medium. In one embodiment, complete depletion can effectively be used, for example to initiate different metabolic pathways, to simplify downstream operations, or for other reasons as well. In one embodiment, the medium component level is allowed to vary by about 10% around a midpoint, in one embodiment, it is allowed to vary by about 30% around a midpoint, and in one embodiment, it is allowed to vary by 60% or more around a midpoint. In one embodiment, the medium component level is maintained by allowing the medium component to be depleted to an appropriate level, followed by increasing the medium component level to another appropriate level. In one embodiment, a medium component, such as vitamin, is added at two different time points during fermentation process. For example, one-half of a total amount of vitamin is added at the beginning of fermentation and the other half is added at midpoint of fermentation.

In another embodiment, the nitrogen level is maintained at a desired level by adding additional nitrogen-containing material as nitrogen is consumed or taken up by the organism. The nitrogen-containing material can be added continuously or at regular or irregular intervals. Useful nitrogen levels include levels of about 5 to about 10 g/L. In one embodiment levels of about 1 to about 12 g/L can also be usefully employed. In another embodiment levels, such as about 0.5, 0.1 g/L or even lower, and higher levels, such as about 20, 30 g/L or even higher are used. In another embodiment a useful nitrogen level is about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22 23, 24, 25, 26, 27, 28, 29 or 30 g/L. Nitrogen can be supplied as a simple nitrogen-containing material, such as an ammonium compounds (e.g. ammonium sulfate, ammonium hydroxide, ammonia, ammonium nitrate, or any other compound or mixture containing an ammonium moiety), nitrate or nitrite compounds (e.g. potassium, sodium, ammonium, calcium, or other compound or mixture containing a nitrate or nitrite moiety), or as a more complex nitrogen-containing material, such as amino acids, proteins, hydrolyzed protein, hydrolyzed yeast, yeast extract, dried brewer's yeast, yeast hydrolysates, distillers' grains, soy protein, hydrolyzed soy protein, fermentation products, and processed or corn steep powder or unprocessed protein-rich vegetable or animal matter, including those derived from bean, seeds, soy, legumes, nuts, milk, pig, cattle, mammal, fish, as well as other parts of plants and other types of animals. Nitrogen-containing materials useful in various embodiments also include materials that contain a nitrogen-containing material, including, but not limited to mixtures of a simple or more complex nitrogen-containing material mixed with a carbon source, another nitrogen-containing material, or other nutrients or non-nutrients, and AFEX treated plant matter.

In another embodiment, the carbon level is maintained at a desired level by adding sugar compounds or material containing sugar compounds ("Sugar-Containing Material") as sugar is consumed or taken up by the organism. The sugar-containing material can be added continuously or at regular or irregular intervals. In one embodiment, additional sugar-containing material is added prior to the complete depletion of the sugar compounds available in the medium. In one embodiment, complete depletion can effectively be used, for example to initiate different metabolic pathways, to simplify downstream operations, or for other reasons as well. In one embodiment, the carbon level (as measured by the grams of sugar present in the sugar-containing material per liter of broth) is allowed to vary by about 10% around a midpoint, in one embodiment, it is allowed to vary by about 30% around a midpoint, and in one embodiment, it is allowed to vary by 60% or more around a midpoint. In one embodiment, the carbon level is maintained by allowing the carbon to be depleted to an appropriate level, followed by increasing the carbon level to another appropriate level. In some embodiments, the carbon level can be maintained at a level of about 5 to about 120 g/L. However, levels of about 30 to about 100 g/L can also be usefully employed as well as levels of about 60 to about 80 g/L. In one embodiment, the carbon level is maintained at greater than 25 g/L for a portion of the culturing. In another embodiment, the carbon level is maintained at about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 101 g/L, 102 g/L, 103 g/L, 104 g/L, 105 g/L, 106 g/L, 107 g/L, 108 g/L, 109 g/L, 110 g/L, 111 g/L, 112 g/L, 113 g/L, 114 g/L, 115 g/L, 116 g/L, 117 g/L, 118 g/L, 119 g/L, 120 g/L, 121 g/L, 122 g/L, 123 g/L, 124 g/L, 125 g/L, 126 g/L, 127 g/L, 128 g/L, 129 g/L, 130 g/L, 131 g/L, 132 g/L, 133 g/L, 134 g/L, 135 g/L, 136 g/L, 137 g/L, 138 g/L, 139 g/L, 140 g/L, 141 g/L, 142 g/L, 143 g/L, 144 g/L, 145 g/L, 146 g/L, 147 g/L, 148 g/L, 149 g/L, or 150 g/L.

The carbon substrate, like the nitrogen substrate, is necessary for cell production and enzyme production, but unlike the nitrogen substrate, it serves as the raw material for production of end products. Frequently, more carbon substrate can lead to greater production of end products. In another embodiment, it can be advantageous to operate with the carbon level and nitrogen level related to each other for at least a portion of the fermentation time. In one embodiment, the ratio of carbon to nitrogen is maintained within a range of about 30:1 to about 10:1. In another embodiment, the ratio of carbon nitrogen is maintained from about 20:1 to about 10:1 or more preferably from about 15:1 to about 10:1. In another embodiment the ratio of carbon nitrogen is about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

Maintaining the ratio of carbon and nitrogen ratio within particular ranges can result in benefits to the operation such as the rate of metabolism of carbon substrate, which depends on the amount of carbon substrate and the amount and activity of enzymes present, being balanced to the rate of end product production. Balancing the carbon to nitrogen ratio can, for example, facilitate the sustained production of these enzymes such as to replace those which have lost activity.

In another embodiment, the amount and/or timing of carbon, nitrogen, or other medium component addition can be related to measurements taken during the fermentation. For example, the amount of monosaccharides present, the amount of insoluble polysaccharide present, the polysaccharase activity, the amount of product present, the amount of cellular material (for example, packed cell volume, dry cell weight, etc.) and/or the amount of nitrogen (for example, nitrate, nitrite, ammonia, urea, proteins, amino acids, etc.) present can be measured. The concentration of the particular species, the total amount of the species present in the fermentor, the number of hours the fermentation has been running, and the volume of the fermentor can be considered. In various embodiments, these measurements can be compared to each other and/or they can be compared to previous measurements of the same parameter previously taken from the same fermentation or another fermentation. Adjustments to the amount of a medium component can be accomplished such as by changing the flow rate of a stream containing that component or by changing the frequency of the additions for that component. For example, the amount of saccharide can be increased when the cell production increases faster than the end product production. In another embodiment the amount of nitrogen can be increased when the enzyme activity level decreases.

In another embodiment, a fed batch operation can be employed, wherein medium components and/or fresh cells are added during the fermentation without removal of a portion of the broth for harvest prior to the end of the fermentation. In one embodiment a fed-batch process is based on feeding a growth limiting nutrient medium to a culture of microorganisms. In one embodiment the feed medium is highly concentrated to avoid dilution of the bioreactor. In another embodiment the controlled addition of the nutrient directly affects the growth rate of the culture and avoids overflow metabolism such as the formation of side metabolites. In one embodiment the growth limiting nutrient is a nitrogen source or a saccharide source.

In various embodiments, particular medium components can have beneficial effects on the performance of the fermentation, such as increasing the titer of desired products, or increasing the rate that the desired products are produced. Specific compounds can be supplied as a specific, pure ingredient, such as a particular amino acid, or it can be supplied as a component of a more complex ingredient, such as using a microbial, plant or animal product as a medium ingredient to provide a particular amino acid, promoter, cofactor, or other beneficial compound. In some cases, the particular compound supplied in the medium ingredient can be combined with other compounds by the organism resulting in a fermentation-beneficial compound. One example of this situation would be where a medium ingredient provides a specific amino acid which the organism uses to make an enzyme beneficial to the fermentation. Other examples can include medium components that are used to generate growth or product promoters, etc. In such cases, it can be possible to obtain a fermentation-beneficial result by supplementing the enzyme, promoter, growth factor, etc. or by adding the precursor. In some situations, the specific mechanism whereby the medium component benefits the fermentation is not known, only that a beneficial result is achieved.

In one embodiment, a fermentation to produce a fuel is performed by culturing a strain of *R. opacus* biocatalyst in a medium having a supplement of lignin component and a concentration of one or more carbon sources. The resulting production of end product such as TAG can be up to 1-fold, 2-fold, 3-fold, 4-fold, 5-fold, 6-fold, 7-fold, 8-fold, 9-fold, and in some cases up to 10-fold and higher in volumetric productivity than a process using only the addition of a relatively pure saccharide source, and can achieve a carbon conversion efficiency approaching the theoretical maximum. The theoretical maximum can vary with the substrate and product. For example, the generally accepted maximum efficiency for conversion of glucose to ethanol is 0.51 g ethanol/g glucose. In one embodiment a biocatalyst can produce about 40-100% of a theoretical maximum yield of ethanol. In another embodiment, a biocatalyst can produce up to about 40%, 50%, 60%, 70%, 80%, 90%, 95% and even 100% of the theoretical maximum yield of ethanol. In one embodiment a biocatalyst can produce up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of a fuel. It can be possible to obtain a fermentation-beneficial result by supplementing the medium with a pretreatment or hydrolysis component. In some situations, the specific mechanism whereby the medium component benefits the fermentation is not known, only that a beneficial result is achieved.

Various embodiments offer benefits relating to improving the titer and/or productivity of fermentation end-product production by a biocatalyst by culturing the organism in a medium comprising one or more compounds comprising particular fatty acid moieties and/or culturing the organism under conditions of controlled pH.

In one embodiment, the pH of the medium is controlled at less than about pH 7.2 for at least a portion of the fermentation. In one embodiment, the pH is controlled within a range of about pH 3.0 to about 7.1 or about pH 4.5 to about 7.1, or about pH 5.0 to about 6.3, or about pH 5.5 to about 6.3, or about pH 6.0 to about 6.5, or about pH 5.5 to about 6.9 or about pH 6.2 to about 6.7. The pH can be controlled by the addition of a pH modifier. In one embodiment, a pH modifier is an acid, a base, a buffer, or a material that reacts with other materials present to serve to raise of lower the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. When more than one pH modifiers are utilized, they can be added at the same time or at different times. In one embodiment, one or more acids and one or more bases can be combined, resulting in a buffer. In one embodiment, media components, such as a carbon source or a nitrogen source can also serve as a pH modifier; suitable media components include those with high or low pH or those with buffering capacity. Exemplary media components include acid- or base-hydrolyzed plant polysaccharides having with residual acid or base, AFEX treated plant material with residual ammonia, lactic acid, corn steep solids or liquor.

In one embodiment, a constant pH can be utilized throughout the fermentation. In one embodiment, the timing and/or amount of pH reduction can be related to the growth conditions of the cells, such as in relation to the cell count, the end product produced, the end product present, or the rate of end product production. In one embodiment, the pH reduction can be made in relation to physical or chemical properties of the fermentation, such as viscosity, medium composition, gas production, off gas composition, etc.

Recovery of Fermentive End Products

In another aspect, methods are provided for the recovery of the fermentive end products, such as an alcohol (e.g. ethanol, propanol, methanol, butanol, etc.) another biofuel or chemical product. In one embodiment, broth will be harvested at some point during of the fermentation, and fermentive end product or products will be recovered. The broth with end product to be recovered will include both end product and impurities. The impurities include materials such as water, cell bodies, cellular debris, excess carbon substrate, excess nitrogen substrate, other remaining nutrients, other metabolites, and other medium components or digested medium components. During the course of processing the broth, the broth can be heated and/or reacted with various reagents, resulting in additional impurities in the broth.

In one embodiment, the processing steps to recover end product frequently includes several separation steps, including, for example, distillation of a high concentration alcohol material from a less pure alcohol-containing material. In one embodiment, the high concentration ethanol material can be further concentrated to achieve very high concentration alcohol, such as 98% or 99% or 99.5% (wt.) or even higher. Other separation steps, such as filtration, centrifugation, extraction, adsorption, etc. can also be a part of some recovery processes for alcohol as a product or biofuel, or other biofuels or chemical products.

In one embodiment a process can be scaled to produce commercially useful biofuels. In another embodiment biocatalyst is used to produce an alcohol, e.g., ethanol, butanol, propanol, methanol, or a fuel such as hydrocarbons hydrogen, TAG, and hydroxy compounds. In another embodiment biocatalyst is used to produce a carbonyl compound such as an aldehyde or ketone (e.g. acetone, formaldehyde, 1-propanal, etc.), an organic acid, a derivative of an organic acid such as an ester (e.g. wax ester, glyceride, etc.), 1,2-propanediol, 1,3-propanediol, lactic acid, formic acid, acetic acid, succinic acid, pyruvic acid, or an enzyme such as a cellulase, polysaccharase, lipases, protease, ligninase, and hemicellulase.

TAG biosynthesis is widely distributed in nature and the occurrence of TAG as reserve compounds is widespread among plants, animals, yeast and fungi. In contrast, however, TAGS have not been regarded as common storage compounds in bacteria. Biosynthesis and accumulation of TAGs have been described only for a few bacteria belonging to the actinomycetes group, such as genera of *Streptomyces, Nocardia, Rhodococcus, Mycobacterium, Dietzia* and *Gordonia*, and, to a minor extent, also in a few other bacteria, such as *Acinetobacter baylyi* and *Alcanivorax borkumensis*. Since the mid-1990's, TAG production in hydrocarbon-degrading strains of those genera has been frequently reported. TAGs are stored in spherical lipid bodies as intracellular inclusions, with the amounts depending on the respective species, cultural conditions and growth phase. Commonly, the important factor for the production of TAGS is the amount of nitrogen that is supplied to the culture medium. The excess carbon, which is available to the culture after nitrogen exhaustion, continues to be assimilated by the cells and, by virtue of oleaginous bacteria possessing the requisite enzymes, is converted directly into lipid. The compositions and structures of bacterial TAG molecules vary considerably depending on the bacterium and on the cultural conditions, especially the carbon sources. See, Brigham C J, et al. (2011) J Microbial Biochem Technol S3:002.

In one embodiment, useful biochemicals can be produced from non-food plant biomass, with a steam or hot-water extraction technique that is carried out by contacting a charge of non-food plant pretreated biomass material such as corn stover or sorghum with water and/or acid (with or without additional process enhancing compounds or materials), in a pressurized vessel at an elevated temperature up to about 160-220° C. and at a pH below about 7.0, to yield an aqueous (extract solution) mixture of useful sugars including long-chain saccharides (sugars), acetic acid, and lignin, while leaving the structural (cellulose and lignin) portion of the lignocellulosic material largely intact. In combination, these potential inhibitory chemicals especially sugar degradation products are low, and the plant derived nutrients that are naturally occurring lignocellulosic-based components are also recovered that are beneficial to a C5 and C6 fermenting organism. Toward this objective, the aqueous extract is concentrated (by centrifugation, filtration, solvent extraction, flocculation, evaporation), by producing a concentrated sugar stream, apart from the other hemicellulose (C5 rich) and cellulosic derived sugars (C6 rich) that are channeled into a fermentable stream.

In another embodiment, following enzyme/acid hydrolysis, additional chemical compounds that are released are recovered with the sugar stream resulting in a short-chain sugar solution containing xylose, mannose, arabinose, rhamnose, galactose, and glucose (5 and 6-carbon sugars). The sugar stream, now significantly rich in C5 and C6 substances can be converted by microbial fermentation or chemical catalysis into such products as triacylglycerol or TAG and further refined to produce stream rich in JP8 or jet fuels. If C5 sugar percentage correction has not been performed, it can be performed before fermentation to satisfy desired combination of C5 and C6 sugars for the fermentation organism and corresponding end product.

Specific Embodiments

A number of methods and systems are disclosed herein. Specific exemplary embodiments of these methods and systems are disclosed below.

Embodiment 1. An industrial scale method for pretreating at least one dry ton of biomass per day, the method comprising: (a) feeding the biomass at a rate of at least one dry metric ton (MT) of biomass per day into an extrusion system comprising a barrel defining an inner chamber comprising a feeder zone and a reaction zone; and (b) treating the biomass at an elevated temperature and pressure within the reaction zone for less than about 20 seconds to produce a pretreated biomass composition comprising a liquid fraction comprising monosaccharides and solid particles comprising cellulose.

Embodiment 2. The method of embodiment 1, wherein the extrusion system further comprises one or more rotatable screws configured to move the biomass through the extrusion system from the feeder zone and through the reaction zone.

Embodiment 3. The method of embodiment 2, wherein the one or more rotatable screws comprise one or more sections that are configured to form one or more plugs from the biomass to separate the inner chamber into two or more zones, including the feeder zone and the reaction zone.

Embodiment 4. The method of any one of embodiments 2-3, comprising one, two, or three rotatable screws.

Embodiment 5. The method of embodiment 4, comprising two rotatable screws.

Embodiment 6. The method of any one of embodiments 1-5, wherein the rate of biomass feeding is at least about 2 dry MT/day, 3 dry MT/day, 4 dry MT/day, 5 dry MT/day, 7.5 dry MT/day, 10 dry MT/day, 15 dry MT/day, 20 dry MT/day, 25 dry MT/day, 50 dry MT/day, 75 dry MT/day, dry 100 MT/day, 150 dry MT/day, or 200 dry MT/day.

Embodiment 7. The method of any one of embodiments 1-5, wherein the extrusion system further comprises a hopper connected to an inlet port at a first end of the barrel for feeding the biomass into the feeder zone.

Embodiment 8. The method of embodiment 7, wherein the hopper further comprises a feeder configured to move the biomass from the hopper through the inlet port.

Embodiment 9. The method of embodiment 8, wherein the feeder is a delivery auger configured to distribute the biomass evenly into the feeder zone.

Embodiment 10. The method of any one of embodiments 1-9, further comprising adding a liquid to the biomass prior to the reaction zone.

Embodiment 11. The method of embodiment 10, wherein the liquid is water.

Embodiment 12. The method of embodiment 10 or 11, wherein the liquid is added through a sealable port located on the hopper.

Embodiment 13. The method of any one of embodiments 10-12, wherein the liquid is added in the feeder zone through one or more sealable ports on the barrel.

Embodiment 14. The method of any one of embodiments 10-13, wherein the liquid is added to increase the moisture content of the biomass to from about: 10-90%, 15-85%, 20-80%, 30-70%, or about 40-60% w/v.

Embodiment 15. The method of any one of embodiments 1-14, wherein the biomass is treated for less than 19, 18, 17, 16, 15, 14, 13, 12, 10, 9, 8, 7, 6, 5, 4, 3, 2, or 1 seconds in the reaction zone.

Embodiment 16. The method of any one of embodiments 1-14, wherein the biomass is treated for about: 20, 19, 18, 17, 16, 15, 14, 13, 12, 10, 9, 8, 7, 6, 5, 4, 3, 2, or 1 seconds in the reaction zone.

Embodiment 17. The method of any one of embodiments 1-14, wherein the biomass is treated for about 5 to 15 seconds in the reaction zone.

Embodiment 18. The method of any one of embodiments 1-14, wherein the biomass is treated for about 10 seconds in the reaction zone.

Embodiment 19. The method of any one of embodiments 1-18, wherein the elevated temperature is about: 50-500° C., 75-400° C., 100-350° C., 150-300° C., or 200-250° C.

Embodiment 20. The method of any one of embodiments 1-18, wherein the elevated temperature is about 150-300° C.

Embodiment 21. The method of any one of embodiments 1-18, wherein the elevated temperature is about 200-250° C.

Embodiment 22. The method of any one of embodiments 1-21, wherein the elevated pressure is about: 50-1000 PSI, 100-750 PSI, 200-600 PSI, 300-500 PSI or 350-450 PSI.

Embodiment 23. The method of any one of embodiments 1-21, wherein the elevated pressure is about 300-500 PSI.

Embodiment 24. The method of any one of embodiments 1-21, wherein the elevated pressure is about 350-450 PSI.

Embodiment 25. The method of any one of embodiments 1-24, further comprising injecting steam into the biomass to increase temperature and pressure.

Embodiment 26. The method of embodiment 25, wherein the steam is injected in the reaction zone.

Embodiment 27. The method of embodiment 25 or 26, wherein the steam is injected through one or more sealable ports in the barrel.

Embodiment 28. The method of any one of embodiments 1-27, wherein the extrusion system further comprises a heated jacket.

Embodiment 29. The method of any one of embodiments 1-28, further comprising adding a chemical agent to the biomass in the reaction zone.

Embodiment 30. The method of embodiment 29, wherein the chemical agent comprises an acid, a base, or a combination thereof.

Embodiment 31. The method of embodiment 30, wherein the chemical agent comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

Embodiment 32. The method of embodiment 30, wherein the chemical agent comprises the acid that is sulfuric acid.

Embodiment 33. The method of embodiment 30, wherein the chemical agent comprises the base that is sodium hydroxide, calcium hydroxide, potassium hydroxide, ammonia, ammonia hydroxide, hydrogen peroxide or a combination thereof.

Embodiment 34. The method of any one of embodiments 29-33, wherein the chemical agent is added to a level of about: 0.1-20% w/v, 1-15% w/v, 1.5-10% w/v, 1-10% w/v, 1-5% w/v, or 2-4% w/v.

Embodiment 35. The method of any one of embodiments 29-33, wherein the chemical agent is added to a level of about 2-4% w/v.

Embodiment 36. The method of any one of embodiments 29-33, wherein the chemical agent is added to a level of about 2% w/v.

Embodiment 37. The method of any one of embodiments 29-33, wherein the chemical agent is added to a level of about 4% w/v.

Embodiment 38. The method of any one of embodiments 1-37, wherein the liquid fraction comprises C5 monosaccharides in at least a 50%, 55%, 60%, 65%, 70%, 75%, 80%, 85%, 90%, 95%, 96%, 97%, 98%, or 99% yield compared to the theoretical maximum based on the biomass.

Embodiment 39. The method of any one of embodiments 1-37, wherein the liquid fraction comprises C5 monosaccharides in at least a 50% yield compared to the theoretical maximum based on the biomass.

Embodiment 40. The method of any one of embodiments 1-37, wherein the liquid fraction comprises C5 monosaccharides in at least a 70% yield compared to the theoretical maximum based on the biomass.

Embodiment 41. The method of any one of embodiments 1-37, wherein the liquid fraction comprises C5 monosaccharides in at least an 85% yield compared to the theoretical maximum based on the biomass.

Embodiment 42. The method of any one of embodiments 1-41, wherein the liquid fraction comprises C6 monosaccharides less than a 50%, 45%, 40%, 35%, 30%, 25%, 20%, 15%, 10%, or 5% yield compared to the theoretical maximum based on the biomass.

Embodiment 43. The method of any one of embodiments 1-41, wherein the liquid fraction comprises C6 monosaccharides less than a 45% yield compared to the theoretical maximum based on the biomass.

Embodiment 44. The method of any one of embodiments 1-41, wherein the liquid fraction comprises C6 monosaccharides less than a 35% yield compared to the theoretical maximum based on the biomass.

Embodiment 45. The method of any one of embodiments 1-42, wherein the solid particles have a size range of about: 1-500 µm, 1-250 µm, 1-200 µm, or 1-150 µm.

Embodiment 46. The method of any one of embodiments 1-42, wherein the solid particles have a size range of about 1-150 µm.

Embodiment 47. The method of any one of embodiments 1-46, wherein the solid particles have an average size of about: 1-50 µm, 5-40 µm, 10-30 µm, or 15-25 µm.

Embodiment 48. The method of any one of embodiments 1-46, wherein the solid particles have an average size of about 15-25 µm.

Embodiment 49. The method of any one of embodiments 1-48, wherein the method produces low levels of one or more inhibitor compounds.

Embodiment 50. The method of embodiment 49, wherein the one or more inhibitor compounds comprise formic acid, acetic acid, hydroxymethyl furfural (HMF), furfural, or a combination thereof.

Embodiment 51. The method of any one of embodiments 1-50, wherein less than 30, 25, 20, 15, 10, or 5 kg of formic acid is produced per MT of dry biomass.

Embodiment 52. The method of any one of embodiments 1-50, wherein less than 30 kg of formic acid is produced per MT of dry biomass.

Embodiment 53. The method of any one of embodiments 1-50, wherein less than 15 kg of formic acid is produced per MT of dry biomass.

Embodiment 54. The method of any one of embodiments 1-50, wherein less than 10 kg of formic acid is produced per MT of dry biomass.

Embodiment 55. The method of any one of embodiments 1-54, wherein less than 100, 80, 60, 50, 40, 30, 25, 20, 15, 10, or 5 kg of acetic acid is produced per MT of dry biomass.

Embodiment 56. The method of any one of embodiments 1-54, wherein less than 60 kg of acetic acid is produced per MT of dry biomass.

Embodiment 57. The method of any one of embodiments 1-54, wherein less than 40 kg of acetic acid is produced per MT of dry biomass.

Embodiment 58. The method of any one of embodiments 1-54, wherein less than 15 kg of acetic acid is produced per MT of dry biomass.

Embodiment 59. The method of any one of embodiments 1-58, wherein less than 20, 15, 10, 7.5, 5, 4, 3, 2, or 1 kg of hydroxymethyl furfural (HMF) is produced per MT of dry biomass.

Embodiment 60. The method of any one of embodiments 1-58, wherein less than 5 kg of hydroxymethyl furfural (HMF) is produced per MT of dry biomass.

Embodiment 61. The method of any one of embodiments 1-58, wherein less than 3 kg of hydroxymethyl furfural (HMF) is produced per MT of dry biomass.

Embodiment 62. The method of any one of embodiments 1-58, wherein less than 2 kg of hydroxymethyl furfural (HMF) is produced per MT of dry biomass.

Embodiment 63. The method of any one of embodiments 1-62, wherein less than 20, 15, 10, 7.5, 5, 4, 3, 2, or 1 kg of furfural is produced per MT of dry biomass.

Embodiment 64. The method of any one of embodiments 1-62, wherein less than 7.5 kg of furfural is produced per MT of dry biomass.

Embodiment 65. The method of any one of embodiments 1-62, wherein less than 5 kg of furfural is produced per MT of dry biomass.

Embodiment 66. The method of any one of embodiments 1-65, wherein the extrusion system further comprises a pressure actuated discharge valve.

Embodiment 67. The method of embodiment 66, wherein the pressure actuated discharge valve is configured to open and close in response to pressure within the extrusion system.

Embodiment 68. The method of embodiment 66 or 67, wherein the pressure actuated discharge valve is connected to an end flange plate at a second end of the barrel.

Embodiment 69. The method of any one of embodiments 66-68, wherein the pressure actuated discharge valve comprises a poppet valve, a ball valve, a check valve, or a rotating knife-gate valve.

Embodiment 70. The method of any one of embodiments 66-68, wherein the pressure actuated discharge valve comprises a poppet valve.

Embodiment 71. The method of any one of embodiments 66-70, wherein the pressure actuated discharge valve is connected to an actuator.

Embodiment 72. The method of embodiment 71, wherein the actuator uses pneumatic force, hydraulic force, electro-mechanical force, or a combination thereof.

Embodiment 73. The method of embodiment 71 or 72, wherein the actuator is operably coupled to a back pressure control unit.

Embodiment 74. The method of embodiment 73, wherein the back pressure control unit is operably coupled to one or more pressure gauges.

Embodiment 75. The method of embodiment 74, wherein at least one of the one or more pressure gauges monitors pressure within the reaction zone.

Embodiment 76. The method of any one of embodiments 1-75, wherein the extrusion system further comprises a flash tank.

Embodiment 77. The method of embodiment 76, wherein the flash tank collects the pretreated biomass composition as it exits the pressure actuated discharge valve.

Embodiment 78. The method of any one of embodiments 1-77, wherein the biomass comprises algae, corn, grass, straw, grain hulls, wood, bark, sawdust, paper, poplars, willows, switchgrass, alfalfa, prairie bluestem, sugar palms, nypa palm, cassava, milo, sorghum, sweet potatoes, molasses, tubers, roots, stems, sago, cassaya, tapioca, rice peas, beans, potatoes, beets, fruits, pits, sorghum, sugar cane, rice, wheat, whole grains, rye, barley, bamboo, seeds, oats, or a combination thereof, or a derivative or byproduct thereof.

Embodiment 79. The method of embodiment 78, wherein the derivative or byproduct thereof comprises corn stover, corn cobs, corn mash, corn fiber, silage, bagasse, distiller's grains, distiller's dried solubles, distiller's dried grains, condensed distiller's solubles, distiller's wet grains, distiller's dried grains with solubles, fiber, fruit peels, rice straw, rice hulls, wheat straw, barley straw, seed hulls, oat hulls, food waste, municipal sewage waste, or a combination thereof.

Embodiment 80. The method of any one of embodiments 1-77, wherein the biomass comprises a woody biomass.

Embodiment 81. The method of embodiment 80, wherein the woody biomass comprises hard wood, soft wood, or a combination thereof.

Embodiment 82. The method of any one of embodiments 1-77, wherein the biomass comprises a hard wood.

Embodiment 83. The method of any one of embodiments 1-82, further comprising hydrolyzing the solid particles comprising cellulose with one or more enzymes to produce monosaccharides.

Embodiment 84. The pretreated biomass composition produced by the method of any one of embodiments 1-83.

Embodiment 85. A sugar stream comprising C6 monosaccharides produced by the method of embodiment 83.

Embodiment 86. A system for industrial scale pretreatment of at least one dry ton of biomass per day, the system comprising: (a) a barrel defining an inner chamber and comprising an inlet port near of first end of the barrel and an end flange plate at a second end of the barrel; (b) one or more rotatable screws configured to move the biomass through the inner chamber of the barrel and containing one or more sections configured to form one or more plugs from the biomass to separate the inner chamber of the barrel into two or more zones, including a feeder zone and a reaction zone; and (c) a pressure actuated discharge valve connected to the end flange plate and configured to open and close in response to pressure within the barrel, thereby allowing for continuous production of a pretreated biomass composition comprising a liquid fraction comprising monosaccharides and solid particles comprising cellulose.

Embodiment 87. The system of embodiment 86, comprising one, two, or three rotatable screws.

Embodiment 88. The system of embodiment 86, comprising two rotatable screws.

Embodiment 89. The system of any one of embodiments 86-88, further comprising a motor configured to rotate the one or more rotatable screws.

Embodiment 90. The system of embodiment 89, wherein the motor is configured to rotate the one or more rotatable screws at about: 100, 250, 400, 500, 750, 1000, 1100, 1250, 1500, or 2000 RPMs.

Embodiment 91. The system of embodiment 89, wherein the motor is configured to rotate the one or more rotatable screws at about 100-2000 RPMs, 250-1500 RMPMs, 400-1100 RPMs, or 500-1000 RPMs.

Embodiment 92. The system of any one of embodiments 86-91, wherein the system is capable of processing biomass at a rate at least about 2 dry MT/day, 3 dry MT/day, 4 dry MT/day, 5 dry MT/day, 7.5 dry MT/day, 10 dry MT/day, 15 dry MT/day, 20 dry MT/day, 25 dry MT/day, 50 dry MT/day, 75 dry MT/day, 100 dry MT/day, 150 dry MT/day, or 200 dry MT/day.

Embodiment 93. The system of any one of embodiments 86-92, wherein the system further comprises a hopper connected to the inlet port for feeding the biomass into the feeder zone.

Embodiment 94. The system of embodiment 93, wherein the hopper further comprises a feeder configured to move the biomass from the hopper through the inlet port.

Embodiment 95. The system of embodiment 94, wherein the feeder is a delivery auger configured to distribute the biomass evenly into the feeder zone.

Embodiment 96. The system of any one of embodiments 93-95, wherein the hopper comprises one or more sealable ports configured to add a liquid to biomass in the hopper.

Embodiment 97. The system of embodiment 96, wherein the liquid is water.

Embodiment 98. The system of any one of embodiments 86-97, wherein the barrel further comprises one or more sealable ports configured to add liquid to biomass in the feeder zone.

Embodiment 99. The system of embodiment 98, wherein the liquid is water.

Embodiment 100. The system of any one of embodiments 86-99, wherein the rotatable screws are capable of conveying biomass through the reaction zone in less than about: 20, 19, 18, 17, 16, 15, 14, 13, 12, 10, 9, 8, 7, 6, 5, 4, 3, 2, or 1 seconds.

Embodiment 101. The system of any one of embodiments 86-99, wherein the rotatable screws are capable of conveying biomass through the reaction zone in about: 20, 19, 18, 17, 16, 15, 14, 13, 12, 10, 9, 8, 7, 6, 5, 4, 3, 2, or 1 seconds.

Embodiment 102. The system of any one of embodiments 86-99, wherein the rotatable screws are capable of conveying biomass through the reaction zone in about 5 to 15 seconds.

Embodiment 103. The system of any one of embodiments 86-102, wherein the barrel further comprises one or more sealable ports configured to add steam to the reaction zone.

Embodiment 104. The system of any one of embodiments 86-103, wherein the barrel further comprises a heat jacket.

Embodiment 105. The system of any one of embodiments 86-104, wherein the system is configured to maintain an elevated temperature in the reaction zone.

Embodiment 106. The system of embodiment 105, wherein the elevated temperature is provided by steam, a heat jacket, or a combination thereof.

Embodiment 107. The system of embodiment 105 or 106, wherein the elevated temperature is about: 50-500° C., 75-400° C., 100-350° C., 150-300° C., or 200-250° C.

Embodiment 108. The system of embodiment 105 or 106, wherein the elevated temperature is about 150-300° C.

Embodiment 109. The system of embodiment 105 or 106, wherein the elevated temperature is about 200-250° C.

Embodiment 110. The system of any one of embodiments 86-109, wherein the system is configured to maintain an elevated pressure in the reaction zone.

Embodiment 111. The system of embodiment 110, wherein the elevated pressure is maintained by addition of steam, liquid, biomass, or a combination thereof.

Embodiment 112. The system of embodiment 110 or 111, wherein the elevated pressure is about: 50-1000 PSI, 100-750 PSI, 200-600 PSI, 300-500 PSI or 350-450 PSI.

Embodiment 113. The system of embodiment 110 or 111, wherein the elevated pressure is about 300-500 PSI.

Embodiment 114. The system of embodiment 110 or 111, wherein the elevated pressure is about 350-450 PSI.

Embodiment 115. The system of any one of embodiments 86-114, wherein the barrel further comprises one or more sealable ports configured to add one or more chemical agents to the reaction zone.

Embodiment 116. The system of embodiment 115, wherein the chemical agent comprises an acid, a base, or a combination thereof.

Embodiment 117. The system of embodiment 116, wherein the chemical agent comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

Embodiment 118. The system of embodiment 116, wherein the chemical agent comprises the acid that is sulfuric acid.

Embodiment 119. The system of embodiment 116, wherein the chemical agent comprises the base that is sodium hydroxide, calcium hydroxide, potassium hydroxide, ammonia, ammonia hydroxide, hydrogen peroxide or a combination thereof.

Embodiment 120. The system of any one of embodiments 115-119, wherein the system is configured to add the chemical agent to a level of about: 0.1-20% w/v, 1-15% w/v, 1.5-10% w/v, 1-10% w/v, 1-5% w/v, or 2-4% w/v.

Embodiment 121. The system of any one of embodiments 115-119, wherein the system is configured to add the chemical agent to a level of about 2-4% w/v.

Embodiment 122. The system of any one of embodiments 115-119, wherein the system is configured to add the chemical agent to a level of about 2% w/v.

Embodiment 123. The system of any one of embodiments 115-119, wherein the system is configured to add the chemical agent to a level of about 4% w/v.

Embodiment 124. The system of any one of embodiments 86-123, wherein the pressure actuated discharge valve comprises a poppet valve, a ball valve, a check valve, or a rotating knife-gate valve.

Embodiment 125. The system of any one of embodiments 86-123, wherein the pressure actuated discharge valve comprises a poppet valve.

Embodiment 126. The system of any one of embodiments 86-125, wherein the pressure actuated discharge valve is connected to an actuator.

Embodiment 127. The system of embodiment 126, wherein the actuator is a pneumatic actuator, a hydraulic actuator, an electro-mechanical actuator, or a combination thereof.

Embodiment 128. The system of embodiment 126 or 127, wherein the actuator is operably coupled to a back pressure control unit.

Embodiment 129. The system of any one of embodiments 86-128, wherein the back pressure control unit is operably coupled to one or more pressure gauges.

Embodiment 130. The system of embodiment 129, wherein the one or more pressure gauges monitor pressure in the barrel via one or more sealable ports in the barrel.

Embodiment 131. The system of embodiment 130, at least one of the one or more pressure gauges is configured to monitor pressure within the reaction zone.

Embodiment 132. The system of any one of embodiments 86-131, wherein the barrel further comprises one or more ports comprising a temperature gauge, a pressure gauge, or a combination thereof.

Embodiment 133. The system of any one of embodiments 86-132, wherein the extrusion system further comprises a flash tank.

Embodiment 134. The system of embodiment 133, wherein the flash tank collects the pretreated biomass composition as it exits the pressure actuated discharge valve.

Embodiment 135. The system of any one of embodiments 86-134, wherein the system is configured to produce the liquid fraction comprising C5 monosaccharides in at least a 50%, 55%, 60%, 65%, 70%, 75%, 80%, 85%, 90%, 95%, 96%, 97%, 98%, or 99% yield compared to the theoretical maximum based on the biomass.

Embodiment 136. The system of any one of embodiments 86-134, wherein the system is configured to produce the liquid fraction comprising C5 monosaccharides in at least a 50% yield compared to the theoretical maximum based on the biomass.

Embodiment 137. The system of any one of embodiments 86-134, wherein the system is configured to produce the liquid fraction comprising C5 monosaccharides in at least a 70% yield compared to the theoretical maximum based on the biomass.

Embodiment 138. The system of any one of embodiments 86-134, wherein the system is configured to produce the liquid fraction comprising C5 monosaccharides in at least an 85% yield compared to the theoretical maximum based on the biomass.

Embodiment 139. The system of any one of embodiments 86-138, wherein the system is configured to produce the liquid fraction comprising C6 monosaccharides in less than a 50%, 45%, 40%, 35%, 30%, 25%, 20%, 15%, 10%, or 5% yield compared to the theoretical maximum based on the biomass.

Embodiment 140. The system of any one of embodiments 86-138, wherein the system is configured to produce the liquid fraction comprising C6 monosaccharides in less than a 45% yield compared to the theoretical maximum based on the biomass.

Embodiment 141. The system of any one of embodiments 86-138, wherein the system is configured to produce the liquid fraction comprising C6 monosaccharides in less than a 35% yield compared to the theoretical maximum based on the biomass.

Embodiment 142. The system of any one of embodiments 86-141, wherein the system is configured to produce the solid particles in a size range of about: 1-500 µm, 1-250 µm, 1-200 µm, or 1-150 µm.

Embodiment 143. The system of any one of embodiments 86-141, wherein the system is configured to produce the solid particles in a size range of about 1-150 µm.

Embodiment 144. The system of any one of embodiments 86-141, wherein the system is configured to produce the solid particles in an average size of about: 1-50 µm, 5-40 µm, 10-30 µm, or 15-25 µm.

Embodiment 145. The system of any one of embodiments 86-141, wherein the system is configured to produce the solid particles in an average size of about 15-25 µm.

Embodiment 146. The system of any one of embodiments 86-145, wherein the biomass comprises algae, corn, grass, straw, grain hulls, wood, bark, sawdust, paper, poplars, willows, switchgrass, alfalfa, prairie bluestem, sugar palms, nypa palm, cassava, milo, sorghum, sweet potatoes, molasses, tubers, roots, stems, sago, cassaya, tapioca, rice peas, beans, potatoes, beets, fruits, pits, sorghum, sugar cane, rice, wheat, whole grains, rye, barley, bamboo, seeds, oats, or a combination thereof, or a derivative or byproduct thereof.

Embodiment 147. The system of embodiment 146, wherein the derivative or byproduct thereof comprises corn stover, corn cobs, corn mash, corn fiber, silage, bagasse, distiller's grains, distiller's dried solubles, distiller's dried grains, condensed distiller's solubles, distiller's wet grains, distiller's dried grains with solubles, fiber, fruit peels, rice straw, rice hulls, wheat straw, barley straw, seed hulls, oat hulls, food waste, municipal sewage waste, or a combination thereof.

Embodiment 148. The system of any one of embodiments 86-145, wherein the biomass comprises a woody biomass.

Embodiment 149. The system of embodiment 148, wherein the woody biomass comprises hard wood, soft wood, or a combination thereof.

Embodiment 150. The system of any one of embodiments 86-145, wherein the biomass comprises a hard wood.

Embodiment 151. A system suitable for the pretreatment of biomass comprising: a barrel defining a reaction compartment; a means for pretreating the biomass retained within the reaction compartment; a screw assembly operably coupled to a first moving means at a first end of the barrel, wherein the screw assembly is configured for inducing the biomass to form one or more plugs within the reaction compartment and for moving the biomass along the reaction compartment to a second end of the barrel as the biomass is pretreated; and a pressure modulator module operably coupled to a second moving means at a second end of the barrel for providing a constant pressure within the reaction compartment.

Embodiment 152. The system of embodiment 151, wherein the reaction compartment is further divided into a feeder zone, a reaction zone, and a pressure modulator zone.

Embodiment 153. The system of embodiment 152, wherein the feeder zone is located at the first end.

Embodiment 154. The system of embodiment 152 or 153, wherein a hopper is attached to the first end for delivering the biomass into the feeder zone.

Embodiment 155. The system of any one of the embodiments 152-154, wherein the hopper further comprises an auger for evenly distributing the biomass into the feeder zone.

Embodiment 156. The system of any one of the embodiments 152-155, wherein a first sealable port is attached to the barrel for delivering an aqueous solution into the feeder zone.

Embodiment 157. The system of any one of the embodiments 152-156, wherein the reaction zone is located between the feeder zone and the second end of the barrel.

Embodiment 158. The system of any one of the embodiments 152-157, wherein the reaction zone is separated from the feeder zone by a first plug.

Embodiment 159. The system of any one of the embodiments 152-158, wherein the reaction zone is further subdivided into a first zone, a second zone, and a third zone.

Embodiment 160. The system of embodiment 159, wherein the first zone and the second zone is separated by a second plug.

Embodiment 161. The system of embodiment 159, wherein the second and the third zone is separated by a third plug.

Embodiment 162. The system of any one of the embodiments 159-161, wherein a second sealable port is attached to the barrel for delivering steam into the first zone and/or the second zone.

Embodiment 163. The system of any one of the embodiments 159-162, wherein a third sealable port is attached to the barrel for delivering a chemical reactant into the second zone.

Embodiment 164. The system of embodiment 163, wherein the chemical reactant is an acid, an alkali, or an additional chemical reactant.

Embodiment 165. The system of any one of the embodiments 151-164, wherein a temperature gauge and a pressure gauge are attached to the barrel for monitoring the temperature and the pressure inside the reaction zone.

Embodiment 166. The system of embodiment 152, wherein the pressure modulator zone is located at the second end of the barrel.

Embodiment 167. The system of embodiment 152 or 166, wherein the pressure modulator zone and the reaction zone are separated by an end plate.

Embodiment 168. The system of embodiment 167, wherein the end plate is constructed to contain a hole for allowing the biomass to move from the reaction zone into the pressure modulator zone.

Embodiment 169. The system of embodiment 168, wherein the biomass moved into the pressure modulator zone is a pretreated biomass.

Embodiment 170. The system of embodiment 168 or 169, wherein a pipe connects the pressure modulator zone to a flash tank for storing the pretreated biomass.

Embodiment 171. The system of embodiment 151, wherein the pressure modulator module comprises an end valve.

Embodiment 172. The system of embodiment 171, wherein the end valve is operably coupled to the second moving means at the second end of the barrel for providing a constant pressure within the reaction zone.

Embodiment 173. The system of embodiment 172, wherein the end valve comprises a poppet valve, a ball valve, a check valve, or a rotating knife-gate valve.

Embodiment 174. The system of embodiment 173, wherein the end valve is a poppet valve.

Embodiment 175. The system of embodiment 151 or 172, wherein the second moving means is an external second moving means.

Embodiment 176. The system of any one of the embodiments 151, 172 or 175, wherein the second moving means comprises an actuator.

Embodiment 177. The system of embodiment 176, wherein the actuator is configured to use pneumatic force.

Embodiment 178. The system of embodiment 176, wherein the actuator is configured to use hydraulic force.

Embodiment 179. The system of embodiment 176, wherein the actuator is configured to use electro-mechanical force.

Embodiment 180. The system of any one of the embodiments 151, 172 or 175-179, wherein the second moving means is further connected to a pressure regulator.

Embodiment 181. The system of embodiment 180, wherein the pressure regulator is configured to receive feedbacks from the pressure gauges.

Embodiment 182. The system of embodiment 151, wherein the first moving means is an external first moving means.

Embodiment 183. The system of embodiment 151 or 182, wherein the first moving means comprises a motor and gearbox combination.

Embodiment 184. The system of embodiment 151, wherein the length of the screw assembly spans through the feeder zone and the reaction zone.

Embodiment 185. The system of embodiment 151 or 184, wherein the screw assembly comprises two or more screws.

Embodiment 186. The system of embodiment 180, wherein the pressure regulator comprises a back-pressure regulator.

Embodiment 187. The system of embodiment 186, wherein the back-pressure regulator comprises a pneumatic regulator.

Embodiment 188. A method for pretreating a biomass comprising: (a) loading a biomass into a barrel comprising a reaction compartment wherein the reaction compartment comprises a means to produce one or more plugs for generating a reaction zone; and (b) pretreating the biomass within the reaction zone with an elevated temperature and a constant pressure for a period of up to 20 seconds; wherein the biomass is reduced in size within the reaction zone.

Embodiment 189. The method of embodiment 188, wherein the reaction compartment further comprises a feeder zone and a pressure modulator zone.

Embodiment 190. The method of embodiment 188 or 189, wherein the feeder zone and the reaction zone are separated by a first plug.

Embodiment 191. The method of any one of the embodiments 188-190, wherein an aqueous solution is added to the biomass in the feeder zone to generate an aqueous composition comprising from about 1% to about 90% w/v suspended solid.

Embodiment 192. The method of any one of the embodiments 188-190, wherein an aqueous solution is added to the biomass in the feeder zone to generate an aqueous composition comprising from about 1% to about 60% w/v suspended solid.

Embodiment 193. The method of embodiment 191 or 192, wherein the suspended solid comprises cellulose, hemicellulose, and/or lignin.

Embodiment 194. The method of embodiment 191 or 192, wherein the aqueous solution is water.

Embodiment 195. The method of any one of the embodiments 188-194, wherein a chemical reactant is further added to the biomass in the reaction zone.

Embodiment 196. The method of embodiment 195, wherein the chemical reactant is an acid, an alkali, or an additional chemical reactant.

Embodiment 197. The method of any one of the embodiments 188-196, wherein steam is further added to the biomass in the reaction zone to further increase the temperature within the reaction zone.

Embodiment 198. The method of any one of the embodiments 188-197, wherein the temperature of the biomass within the reaction zone is between about 80° C. and about 300° C.

Embodiment 199. The method of any one of the embodiments 188-197, wherein the temperature of the biomass within the reaction zone is between about 160° C. and about 210° C.

Embodiment 200. The method of any one of the embodiments 188-199, wherein the pressure of the biomass within the reaction zone is between about 300 psi and about 1000 psi.

Embodiment 201. The method of any one of the embodiments 188-199, wherein the pressure of the biomass within the reaction zone is between about 400 psi and about 800 psi.

Embodiment 202. The method of any one of the embodiments 188-199, wherein the pressure of the biomass within the reaction zone is between about 400 psi and about 600 psi.

Embodiment 203. The method of any one of the embodiments 188-202, wherein the pressure of the biomass within the reaction zone is further maintained by a pressure modulator module within the pressure modulator zone.

Embodiment 204. The method of embodiment 203, wherein the pressure modulator module comprises an end valve.

Embodiment 205. The method of embodiment 204, wherein the end valve is operably coupled to a moving means at a second end of the barrel for providing a constant pressure within the reaction zone.

Embodiment 206. The method of embodiment 204 or 205, wherein the end valve comprises a poppet valve, a ball valve, a check valve, or a rotating knife-gate valve.

Embodiment 207. The method of embodiment 206, wherein the end valve is a poppet valve.

Embodiment 208. The method of embodiment 205, wherein the moving means is an external moving means.

Embodiment 209. The method of embodiment 205 or 208, wherein the moving means comprises an actuator.

Embodiment 210. The method of embodiment 209, wherein the actuator uses pneumatic force.

Embodiment 211. The method of embodiment 209, wherein the actuator uses hydraulic force.

Embodiment 212. The method of embodiment 209, wherein the actuator uses electro-mechanical force.

Embodiment 213. The method of any one of the embodiments 205 or 208-212, wherein the moving means is further connected to a pressure regulator.

Embodiment 214. The method of embodiment 213, wherein the pressure regulator is configured to receive feedbacks from a pressure gauge.

Embodiment 215. The method of embodiment 214, wherein the pressure gauge is attached to the barrel for monitoring the pressure within the reaction zone.

Embodiment 216. The method of any one of embodiments 214 or 215, wherein the pressure regulator is back-pressure regulator.

Embodiment 217. The method of embodiment 216, wherein the back-pressure regulator comprises a pneumatic pressure regulator.

Embodiment 218. The method of any one of the embodiments 188-217, wherein the biomass is further discharged into a flash tank as pretreated biomass.

Embodiment 219. The method of embodiment 218, wherein the pretreated biomass comprises a total saccharide concentration of from about 5% and about 55% w/v.

Embodiment 220. The method of embodiment 218, wherein the pretreated biomass comprises a total saccharide concentration of from about 15% and about 45% w/v.

Embodiment 221. The method of embodiment 216, wherein the pretreated biomass comprises a total saccharide concentration of from about 25% and about 35% w/v.

Embodiment 222. The method of embodiment 218, wherein the one or more plugs is produced by a screw assembly.

Embodiment 223. The method of embodiment 222, wherein the screw assembly comprises two or more screws.

Embodiment 224. The method of any one of the embodiments 188-223, wherein the biomass comprises algae, corn stover, corn cobs, corn mash, corn fiber, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, sugar palms, nypa palm, fiber, cassava, milo, sorghum, sweet potatoes, molasses, tubers, roots, stems, sago, cassaya, tapioca, rice peas, beans, potatoes, beets, fruits, fruit peels, pits, sorghum, sugar cane, rice, rice straw, rice hulls, wheat, wheat straw, whole grains, rye, barley, barley straw, bamboo, seeds, seed hulls, oats, oat hulls, food waste, municipal sewage waste, or a combination thereof.

Embodiment 225. The method of any one of the embodiments 218-221, wherein the pretreated biomass further undergoes a fermentation step.

Embodiment 226. The method of embodiment 225, wherein one or more fermenting microorganisms are added into the pretreated biomass.

Embodiment 227. The method of embodiment 226, wherein the one or more fermenting microorganisms comprise a bacterial species, a yeast species, an algae, a non-yeast fungus, or a combination thereof.

Embodiment 228. The method of embodiment 226, wherein the one or more fermenting microorganisms comprise a strain of *Saccharomyces cerevisiae*.

Embodiment 229. The method of embodiment 226, wherein the one or more fermenting microorganisms comprise a genetically modified microorganism.

Embodiment 230. The method of any of embodiment 188-229, wherein pretreating comprises hydrating the biomass in a non-neutral pH aqueous medium.

Embodiment 231. The method of embodiment 230, wherein the non-neutral pH aqueous medium is at from about 30° C. to about 70° C.

Embodiment 232. The method of embodiments 230 or 231, wherein the non-neutral aqueous medium comprises an acid or a base at from about 0.1% to about 5% v/w by dry biomass weight.

Embodiment 233. A fermentation end-product produced by the method of embodiments 188-229.

Embodiment 234. The fermentation end-product of embodiment 233, wherein the fermentation end-product is an alcohol.

Embodiment 235. The fermentation end-product of embodiment 234, wherein the fermentation end-product is ethanol.

Embodiment 236. A sugar stream produced by the method of embodiments 188-229.

Embodiment 237. A valve assembly comprising: a reaction compartment comprising a first end and a second end; an end plate, wherein the end plate is located between the first end and the second end of the reaction chamber thereby separating the reaction compartment into a reaction zone and a pressure modulator zone, and wherein the end plate is constructed to contain a hole; and an end valve, wherein the end valve is located in the pressure modulator zone, and wherein the end valve is operably coupled to a moving means at the second end of the reaction compartment for providing a constant pressure within the reaction zone.

Embodiment 238. The valve assembly of embodiment 237, wherein the end valve comprises a poppet valve, a ball valve, a check valve, or a rotating knife-gate valve.

Embodiment 239. The valve assembly of embodiment 237, wherein the end valve is a poppet valve.

Embodiment 240. The valve assembly of embodiment 237, wherein the moving means is an external moving means.

Embodiment 241. The valve assembly of embodiment 237 or 240, wherein the moving means comprises an actuator.

Embodiment 242. The valve assembly of embodiment 241, wherein the actuator is configured to use pneumatic force.

Embodiment 243. The valve assembly of embodiment 241, wherein the actuator is configured to use hydraulic force.

Embodiment 244. The valve assembly of embodiment 241, wherein the actuator is configured to use electro-mechanical force.

Embodiment 245. The valve assembly of any one of embodiments 237-244, wherein the moving means is further connected to a pressure regulator.

Embodiment 246. The valve assembly of embodiment 245, wherein the pressure regulator comprises a back-pressure regulator.

Embodiment 247. The valve assembly of embodiment 246, wherein the back-pressure regulator comprises a pneumatic regulator.

Embodiment 248. The valve assembly of any one of embodiments 237-247, further comprising a valve flange, wherein the valve flange comprises a seat configured to seat the end valve.

Embodiment 249. The valve assembly of embodiment 248, wherein the seat comprises a ceramic seat.

EXAMPLES

The following examples serve to illustrate certain embodiments and aspects and are not to be construed as limiting the scope thereof.

Example 1. Pretreatment of Biomass Using a Twin Screw Extruder

A twin screw extruder as diagrammed in FIG. 2 was used to perform four continuous runs of 224, 695, 1100, and 977 hours each. The extruder was run with indirect heating through the reactor walls until the end of the experiment. A flow rate of up to 136 kg/hr was reached through the extruder with direct steam injection to supply process heat. The materials selected were acid resistant. The feed was metered through a weight belt feeder and fell into a crammer feeder supplying the barrel of the extruder. Two screws intermeshed and provided rapid heat and mass transfer when steam and acid were injected through steam and acid ports connected to the cylindrical barrel of the extruder as shown in FIG. 2. The steam and acid supplying ports were sealed by reverse-flow sections in the screws. A hydraulically operated pressure control valve was seated in a ceramic seal and pressure was controlled to maintain as constant a pressure as possible in the reaction section of the extruder.

The solids were exposed to high temperature and pressure and low pH for a maximum of about 10 seconds in the reaction zone as shown in the extruder depicted in FIG. 2 before being exploded into the flash tank. Residence time in the reaction zone was controlled by the rotational time of the screws. The surge chamber above the screws in the pump feeder acted as a flash vessel, where hot water is vaporized, cooling the product and removing some of the low-boiling inhibitors, such as furfural. Under these conditions, extrusion did not appear to produce enough furfural or HMF to inhibit yeast growth or fermentation, as long as overcooking was avoided with short reaction periods. HMF and furfural, reversion inhibitors, were formed in small amounts during this pretreatment (e.g., a total of 0.3 to 0.5 wt. % of the dry pretreated product).

Example 2. Particle Size Following Pretreatment with a Twin Screw Extruder

This run was conducted to evaluate the particle size reduction that takes place during biomass pretreatment in a modified twin screw extruder. Cherry sawdust, with an average particle size of about 3 mm×3 mm×1 mm and an average moisture content of 31% was used as the raw biomass feedstock. The cherry biomass was fed into a ZSK-30 twin screw extruder, manufactured by Coperion, essentially as described in Example 1. The processing parameters used for the experiment are presented in Table 2.

TABLE 2

| Feedstock | Mass Throughput Dry g/min | Pressure psig | Temp. ° C. | Acid Addition g/min | Water Addition g/min | Residence Time seconds |
|---|---|---|---|---|---|---|
| Cherry Sawdust | 398.4 | 400 | 231 | 7.6 | 1134 | 10 |

The cherry sawdust was processed on a continuous basis. The final moisture content of the processed cherry sawdust was about 76.8%. Once steady state was achieved a sample of the pretreated material was collected for particle size analysis. The sample was analyzed through a Mie Scattering theory using a Horiba LA-920, capable of measuring particle diameters from 0.02 μm to 2000 μm. The results indicated a significant particle size reduction occurring throughout the pretreatment process. The average particle size was reduced from 3 mm in the raw material to 20.75 μm in the pretreated effluent. A summary of the particle size distribution is presented in FIG. 13.

Example 3

Analysis of Biomass Slurry after Pretreatment

Table 3 is a summary of various types of biomass pretreated at an optimized set of conditions, with the analysis of the resulting sugar and organic acid composition of the liquid fraction coming off of pretreatment as slurry of biomass. Water or steam was added to adjust to the desired solids content for pretreatment.

Wet distillers grain at 68.10% moisture was fed into a twin screw extruder crammer. Conditions in the extruder were set at a steam valve pressure of 39.0 kg/hr, 232° C., and an end valve pressure of 400 psi, with 4.0% $H_2SO_4$. Biomass exited the extruder as 21.8% total solids slurry. For analysis post pretreatment, the moisture content of the biomass slurry was determined using a moisture analyzer-balance. A sample of the homogenous slurry was centrifuged for 5 minutes at 6000 rpm, and the supernatant used for standard HPLC sample preparation. All sugar and organic acid analysis was performed on a Shimadzu HPLC system with a RID-10A detector and a BIORAD Aminex HPX-87H column (300× 7.8 mm). The mobile phase was 0.01N $H_2SO_4$ and the HPLC had an 8 point calibration from 0.1 g/L to 50.0 g/L.

Cherry sawdust was resifted at 34.4% moisture. Conditions in the extruder system were set at a steam valve pressure of 27.2 kg/hr, 232° C., and an end valve pressure of 400 psi, with 2.0% $H_2SO_4$. Biomass exited the system as 25.9% total solids homogeneous slurry. Biomass slurry was cooled and then analyzed as described above.

Red Maple measuring 22.50% moisture was fed to the extruder system at a steam valve pressure of 30.4 kg/hr, 232° C., and an end valve pressure of 400 psi, with 2.0% $H_2SO_4$. Biomass exited the extruder system as 29.1% total solids homogeneous slurry. The biomass slurry was cooled and then analyzed as described above.

Yellow Poplar at 37.58% moisture was fed to the extruder system at a steam valve pressure of 30.4 kg/hr, 232° C., and an end valve pressure of 400 psi, with 2.0% $H_2SO_4$. Biomass exited the extruder system as 26.8% total solids homogeneous slurry. The biomass slurry was cooled and then analyzed as described above.

The analyses of the liquid fraction of pretreated slurries produced a hemicellulose-rich extraction from the lignocellulose biomass, and a low concentration of organic acids and inhibitors.

TABLE 3

Pretreatment conditions and composition of liquid fraction of pretreated material; kg/MT indicates kilograms per dry metric ton of biomass.

| ID | Raw Feedstock | Temp. (° C.) | End Valve Pressure (PSI) | Acid Dosing (%) | Steam Valve (lbs/hr) | Solids (%) | Glucose (kg/MT) |
|---|---|---|---|---|---|---|---|
| WDG150123-S11 | Wet Distillers Grains | 232 | 400 | 4.0 | 95 | 21.8 | 70.4 |
| HW150730-R10B6 | Cherry | 232 | 400 | 2.0 | 67 | 25.9 | 70.3 |
| HW150728-R10B3 | Red Maple | 232 | 400 | 2.0 | 67 | 29.1 | 101.2 |
| HW150618-R9B1 | Yellow Poplar | 232 | 400 | 2.0 | 67 | 26.8 | 131.1 |

| ID | Raw Feedstock | Xylose (kg/MT) | Arabinose (kg/MT) | Formic Acid (kg/MT) | Acetic Acid (kg/MT) | HMF (kg/MT) | Furfural (kg/MT) |
|---|---|---|---|---|---|---|---|
| WDG150123-S11 | Wet Distillers Grains | 127.4 | 77.9 | 27.6* | 12.1 | 0.0 | 0.6 |
| HW150730-R10B6 | Cherry | 212.1 | 14.2 | 10.4 | 29.4 | 0.6 | 1.8 |

TABLE 3-continued

Pretreatment conditions and composition of liquid fraction of pretreated material; kg/MT indicates kilograms per dry metric ton of biomass.

| | | | | | | | |
|---|---|---|---|---|---|---|---|
| HW150728-R10B3 | Red Maple | 204.4 | 15.3 | 11.7 | 37.2 | 1.9 | 3.0 |
| HW150618-R9B1 | Yellow Poplar | 247.6 | 0.0 | 8.3 | 56.1 | 2.8 | 5.8 |

*Indicates amount of glycerol (kg/MT) in liquid fraction of processed Wet Distillers Grains.

Table 4 provides a summary of the sugar compositional analysis of the various feedstocks outlined in Table 3 and Table 5.

Compositional Analysis

Wet distillers grain: corn grain sugar composition was analyzed using a bone dried sample of feedstock. The NREL LAP for "Determination of Structural Carbohydrates and Lignin in Biomass" (NREL/TP-510-42618: A. Sluiter, B. Hames, R. Ruiz, C. Scarlata, J. Sluiter, D. Templeton, and D. Crocker) was followed to quantify the total theoretical available sugars within the raw feedstock by using a 72% sulfuric acid hydrolysis for 1 hour at 35° C. followed by a 4% sulfuric acid hydrolysis for 1 hour at 249° C. in an autoclave. Sugar analysis was performed on a Shimadzu HPLC system with a RID-10A detector and a BIORAD Aminex HPX-87H column (300×7.8 mm). The mobile phase was 0.01N $H_2SO_4$ and the HPLC had an 8 point calibration from 0.1 g/L to 50.0 g/L.

Cherry, red maple, and yellow poplar were analyzed for sugar composition post pretreatment. The compositional analysis of theoretical monomeric sugars was determined via enzymatic hydrolysis with an overdosed amount of cellulase enzyme cocktail to hydrolyze all possible sugars present in the cellulose and hemicellulose fractions. Sugar analysis was performed on a Shimadzu HPLC system with a RID-10A detector and a BIORAD Aminex HPX-87H column (300×7.8 mm). The mobile phase was 0.01N $H_2SO_4$ and the HPLC had an 8 point calibration from 0.1 g/L to 50.0 g/L.

TABLE 4

Compositional analysis of raw feedstocks

| Feedstock | Average Cellulose (kg/MT) | Average Hemi-cellulose (kg/MT) | Average Lignin (kg/MT) | Average Glucose (kg/MT) | Average Xylose (kg/MT) | Average Arabinose (kg/MT) | Total Avail. Sugar (kg/MT) |
|---|---|---|---|---|---|---|---|
| Wet Distillers Grains | 154.1 | 228.1 | 209.2 | 169.6 | 171.9 | 79.0 | 420.5 |
| Cherry | 411.5 | 216.4 | 372.1 | 452.7 | 238.0 | 16.0 | 706.7 |
| Red Maple | 450.1 | 206.4 | 343.5 | 495.1 | 227.0 | 14.2 | 736.3 |
| Yellow Poplar | 446.8 | 226.1 | 327.1 | 491.5 | 248.7 | 0.0 | 740.2 |

Table 5 summarizes sugar conversions from pretreatment and subsequent enzymatic hydrolysis as described infra. Conversion efficiencies were calculated as a percentage of the compositional analysis of monomeric sugars, taken as a theoretical maximum sugar yield.

Enzymatic Hydrolysis

The moisture content of the pretreated biomass slurry was determined using a moisture analyzer-balance. Water was added to produce a slurry of 15% total solids and the slurry was mixed to homogeneity. The pH of the slurry was adjusted to 5.2 using 10M NaOH and then 100 g aliquots of slurry were transferred into individual 250 mL shake flasks. Commercially available cellulase enzyme was added at 8 kg of protein per metric ton of dry solids into each 250 mL shake flask. Hydrolysis was carried out in a Kuhner incubator shaker (Climo-Shaker ISF4-X) at 50° C. and 200 rpm for the duration of 72 hours.

Samples were taken at multiple time points throughout hydrolysis and after 72 hours, conversion efficiencies were calculated. The hydrolysate samples were collected for analysis and centrifuged. The supernatant was analyzed for monomeric sugars, and organic acids and inhibitors via HPLC as described supra.

TABLE 5

Sugar recovery from pretreatment and enzymatic hydrolysis, calculated as a percentage of the compositional analysis of monomeric sugars.

| Feedstock | Glucose Conversion (%) Pretreatment | Glucose Conversion (%) Enzyme Hydrolysis | Xylose Conversion (%) Pretreatment | Xylose Conversion (%) Enzyme Hydrolysis |
|---|---|---|---|---|
| Wet Distillers Grains | 41.5 | 97.0 | 74.1 | 87.1 |
| Cherry | 15.5 | 90.1 | 89.1 | 98.8 |
| Red Maple | 20.5 | 90.6 | 90.1 | 99.6 |
| Yellow Poplar | 30.6 | 85.8 | 96.3 | 97.0 |

| Feedstock | Arabinose Conversion (%) Pretreatment | Arabinose Conversion (%) Enzyme Hydrolysis | Total Sugar Conversion (%) Pretreatment | Total Sugar Conversion (%) Enzyme Hydrolysis |
|---|---|---|---|---|
| Wet Distillers Grains | 98.7 | 99.0 | 65.7 | 94.4 |
| Cherry | 88.8 | 98.1 | 42.0 | 93.2 |
| Red Maple | 100.0 | 100.0 | 43.6 | 92.9 |
| Yellow Poplar | — | — | 51.2 | 91.4 |

Example 4

In addition to the treatments described supra, numerous other types of feedstocks were processed through the herein defined apparatus. For example, waste paper from a waste management facility was ground in a Fitzmill to pass through a 2.36 mm screen and blended to 1.25 wt % in water prior to being processed. Other feedstocks included corn fiber at 25% solids, bagasse (16 runs), softwoods (33 runs), rice straw (12 runs), wheat straw (8 runs), mixed straws, barley straw (8 runs) and oat hulls (10 runs).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An industrial scale method for pretreating at least one dry ton of biomass per day in an extrusion system,
    wherein the extrusion system comprises
        (i) a barrel, wherein the barrel comprises a first inlet port near a first end of the barrel for receiving the biomass, an inner chamber comprising a feeder zone and a reaction zone, and a discharge valve opening at a second end of the barrel; and
        (ii) one or more rotatable screws within the inner chamber, wherein the one or more rotatable screws include sections configured to form one or more plugs,
    wherein the method comprises:
        (a) feeding the biomass at a rate of at least one dry metric ton (MT) of biomass per day into the feeder zone of the extrusion system through the first inlet port;
        (b) moving the biomass via the one or more rotatable screws through the barrel in a direction from the first end to the second end,
        (c) forming a plug from the biomass as the biomass is moved continuously through the extrusion system, wherein the plug separates the inner chamber comprising the biomass into the feeder zone and the reaction zone, wherein the feeder zone is upstream of the plug in the direction from the first end to the second end, and the reaction zone is downstream of the plug in the direction from the first end to the second end;
        (d) adding, through one or more sealable ports, to the biomass in the reaction zone pressurized steam and a chemical agent, and treating the biomass at a temperature of about 50-500° C. and a pressure of about 50-1000 PSI within the reaction zone for less than about 20 seconds, thereby producing a pretreated biomass composition comprising a liquid fraction comprising monosaccharides and solid particles comprising cellulose; and (e) continuously releasing the pretreated biomass composition from the extrusion system through the discharge valve opening.

2. The method of claim 1, wherein the extrusion system comprises two rotatable screws.

3. The method of claim 1, wherein the rate of biomass feeding is at least 75 dry MT/day.

4. The method of claim 1, further comprising adding a liquid to the biomass prior to the reaction zone through a second inlet port on the barrel.

5. The method of claim 1, wherein the biomass is treated for about 5 to 15 seconds in the reaction zone.

6. The method of claim 1, wherein the elevated temperature is about 150-300° C.

7. The method of claim 1, wherein the elevated pressure is about 300-500 PSI.

8. The method of claim 1, wherein the chemical agent comprises an acid, a base, or a combination thereof.

9. The method of claim 1, wherein the chemical agent comprises sulfuric acid.

10. The method of claim 1, wherein less than 15 kg of formic acid is produced per MT of dry biomass.

11. The method of claim 1, wherein less than 60 kg of acetic acid is produced per MT of dry biomass.

12. The method of claim 1, wherein less than 5 kg of hydroxymethyl furfural (HMF) is produced per MT of dry biomass.

13. The method of claim 1, wherein less than 7.5 kg of furfural is produced per MT of dry biomass.

* * * * *